United States Patent [19]
Randolph et al.

[11] Patent Number: 6,020,521
[45] Date of Patent: Feb. 1, 2000

[54] MACROLIDE LHRH ANTAGONISTS

[75] Inventors: John T. Randolph, Mundelein; Fortuna Haviv, Deerfield, both of Ill.; Daryl Sauer, Trevor, Wis.; Philip Waid, Indianapolis, Ind.; Charles J. Nichols, Greendale, Wis.; Nicholas A. Mort, Waukegan, Ill.; Christopher R. Dalton, Mundelein, Ill.; Jonathan Greer, Chicago, Ill.

[73] Assignee: Abbott Laboratories, Abbott Park, Ill.

[21] Appl. No.: 09/140,805

[22] Filed: Aug. 26, 1998

[51] Int. Cl.[7] ..................................................... C07C 69/52
[52] U.S. Cl. .............................................................. 560/205
[58] Field of Search ............................................... 560/205

[56] References Cited

U.S. PATENT DOCUMENTS 4,677,097  6/1987  Omura et al. .............................. 514/29

FOREIGN PATENT DOCUMENTS 0215355  3/1987  European Pat. Off. .
0248279  12/1987  European Pat. Off. .
0349100  1/1990  European Pat. Off. .
0559896  9/1993  European Pat. Off. .

OTHER PUBLICATIONS

Chem. Pharm. Bull. vol. 37. No. 10 (1989) pp. 2701–2709 T. Sunazuka et al. month not available.

*Primary Examiner*—Kathleen K. Fonda
*Attorney, Agent, or Firm*—Mona Anand

[57] ABSTRACT

Disclosed are 3'-N-desmethyl-3'-N-susbstituted-6-O-methyl-11-deoxy-11,12-cyclic carbamate erythrolide A derivatives which are antagonists of luteinizing hormone-releasing hormone (LHRH). Also disclosed are pharmaceutical compositions comprising the compounds, to methods of using the compounds and to the process of making the same.

12 Claims, No Drawings

MACROLIDE LHRH ANTAGONISTS

TECHNICAL FIELD

The present invention relates to a class of macrolide compounds which are antagonists of luteinizing hormone-releasing hormone (LHRH), to pharmaceutical compositions comprising the compounds, to methods of using the compounds and to the process of making the same. More particularly, the present invention relates to 3'-bis-N-desmethyl-3'-N-substituted-desosaminyl-6-O-methyl-11-deoxy-11,12-cyclic carbamate-erythronolide A derivatives which are antagonists of LHRH.

BACKGROUND OF THE INVENTION

The gonadotropins, follicle stimulating hormone (FSH), luteinizing hormone (LH), and chorionic gonadotropin (CG) are required for ovulation, spermatogenesis, and the biosynthesis of sex steroids. A single hypothalamic hormone, gonadotropin-releasing hormone (GnRH) also known as LHRH is responsible for regulating the secretion of both FSH and LH in mammals.

LHRH is a decapeptide having the structure:

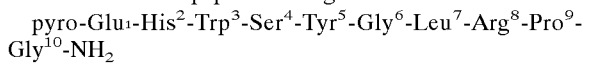

where the superscripts designate the position of each aminoacyl residue in the decapeptide chain.

LHRH is released from the hypothalamus and binds to a receptor on the pituitary gland, causing the release of LH and FSH which subsequently act on the gonads to stimulate the synthesis of steroid sex hormones. The pulsatile release of LHRH, and thereby the release of LH and FSH, controls the reproductive cycle in animals and humans. Acute doses of LHRH agonists increase the levels of LH and steroidal sex hormones in both animals and humans. Paradoxically, chronic doses of LHRH agonists suppress the level of LH and steroidal sex hormones. Consequently, the effect of multiple doses of LHRH agonists is to suppress estrogen formation in females and testosterone production in males. The same effect is observed in both animals and humans after administration of either acute or chronic doses of LHRH antagonists.

In recent years, considerable research effort has been expended on finding antagonists of LHRH. These efforts have produced a number of peptide LHRH antagonists, which suppress LH and reproductive hormones in mammals upon acute or chronic administrations. See for example, M. J. Karten in "Modes of Action of GnRH and GnRH analogs", edited by W. F. Crowley and P. M. Conn, p. 277 (1992). The literature has reported that LHRH antagonists are useful in the treatment of a variety of conditions in which the suppression of sex steroids plays a key role including contraception, delay of puberty, treatment of benign prostatic hyperplasia, palliative treatment or remission of hormonal-dependent tumors of the prostate, the treatment of cryptorchidism, hirsutism in women, gastric motility disorders, dysmenorrhea, and endometriosis.

Current LHRH antagonists are decapeptides which, because of their low oral bioavailability, are administered either intravenously or subcutaneously. Non-peptide heterocyclic antagonists have been reported in the literature, see for example, WO 95/29900, WO 97/22707, and WO 97/21704. Non-peptide LHRH antagonists have the possible advantage of improved oral bioavailability and are smaller molecules.

However, there are no known reports of macrolide compounds as LHRH antagonists in the literature. Macrolide antibiotics and macrolide prokinetic agents are known. For example, macrolide antibiotics derived from erythromycin which contain 11,12-cyclic carbamate moieties are disclosed in EP 248 279 A2. The 3'-N substituted erythromycin derivatives, which are effective antibacterial agents, are described in EP 0 559 896 A1. Macrocyclic lactone (macrolide) prokinetic agents are known. See J. S. Gidda et al., in European Patent Application No. 0349100, published Jan. 3, 1990, which discloses 12-membered macrolides for use as gastrointestinal motility enhancers. S. Omura and Z. Itoh, in U.S. Pat. No. 4,677,097, issued Jun. 30, 1987; European Application No. 215,355, published Mar. 25, 1987; and European Application No. 213,617, published Mar. 11, 1987; disclose derivatives of erythromycins A, B, C and D which are useful as stimulants of digestive tract contractile motion. Additionally, T. Sunazuka, et al., Chem. Pharm. Bull. 37(10): 2701–2709 (1989) discloses quaternary derivatives of 8,9-anhydroerythromycin A 6,9-hemiacetal and 9,9-dihydro-erythromycin A 6,9-epoxide with gastrointestinal motor stimulating activity.

U.S. application Ser. Nos. 09/049,458, and 09/049,963, now U.S. Pat. No. 5,955,440, filed Mar. 27, 1998, disclose 3'-N-desmethyl-3'-N-substituted-6-O-methyl-11-deoxy-11, 12-cyclic carbamate erythromycin A derivatives, which are effective as LHRH antagonists.

However, there is a continuing need to develop new compounds that are effective as LHRH antagonists.

SUMMARY OF THE INVENTION

In one aspect, the present invention relates to a compound having the formula:

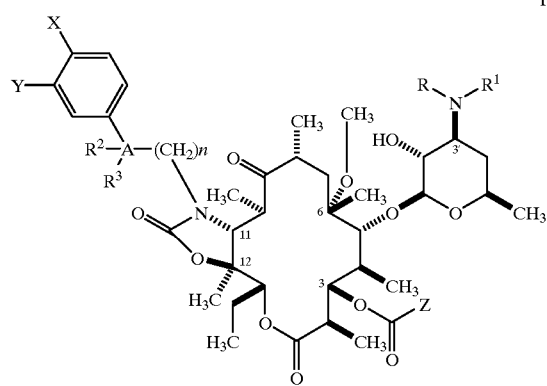

or a pharmaceutically acceptable salt or ester thereof, wherein

A is selected from the group consisting of:
(a) —C,
(b) —N, and
(c) —O, and
(d) cycloalkyl;

X and Y are independently selected at each occurrence from the group consisting of:
(a) hydrogen,
(b) halide,
(c) alkoxy,
(d) alkyl,
(e) aryl, and
(f) substituted aryl;

R and $R^1$ are independently at each occurrence
a) hydrogen,
b) alkyl, c) cycloakyl, d) 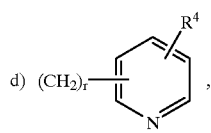, wherein $R^4$ is independently at each occurrence a hydrogen or an alkyl, and r is 0, 1, 2, 3, or 4; or e) taken together with the nitrogen to which they are attached R and $R^1$ form

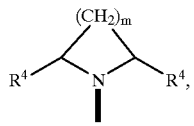

wherein $R^4$ is as defined above, and m is 2, 3, or 4;
$R_2$ and $R_3$ are independently at each occurrence
(a) hydrogen,
(b) methyl, or
$R_2$ and $R_3$ together form a cyclic moiety, when A is C;
R3 is absent when A is N, and
n=1, 2 or 3; and
Z is

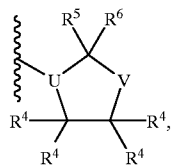

wherein
U is —CH, —CCH$_3$, or —N;
V is CH$_2$, O, or S;
$R^4$ is as defined above; and
$R^5$ and $R^6$ are independently at each occurrence hydrogen or alkyl, or together they form —C=O or —C=S.

In another aspect, the present invention relates to a process for preparing the compound formula I. The process comprises the steps of:

(a) demethylating 3'-amino of a compound of formula:

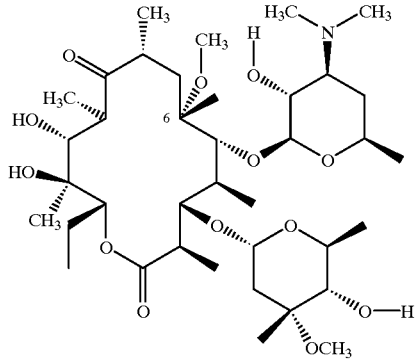

with iodine in presence of a base, followed by alkylation to afford a compound of the formula:

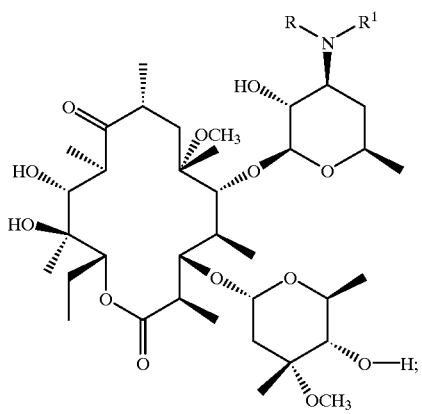

(b) protecting 2'- and 4"-hydroxy groups;

(c) reacting the compound obtained in steps (a) and (b) with sodium bis(trimethylsilyl)amide and carbonyldiimidazole, followed by reaction with an amino compound of the formula:

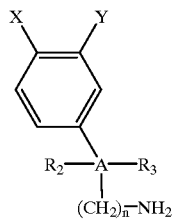

to afford a compound of the formula:

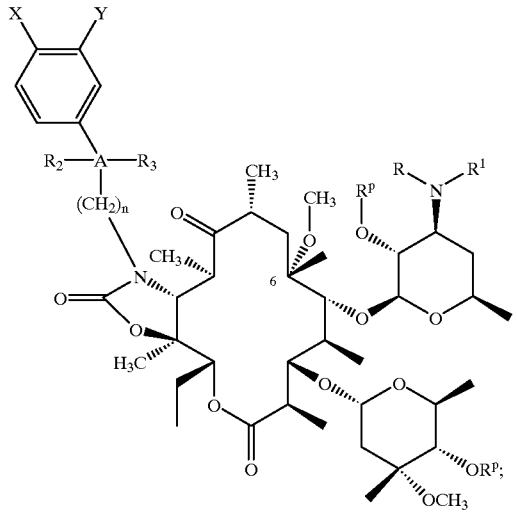

(d) hydrolyzing the compound obtained in step (c) with an acid to afford a compound of the formula:

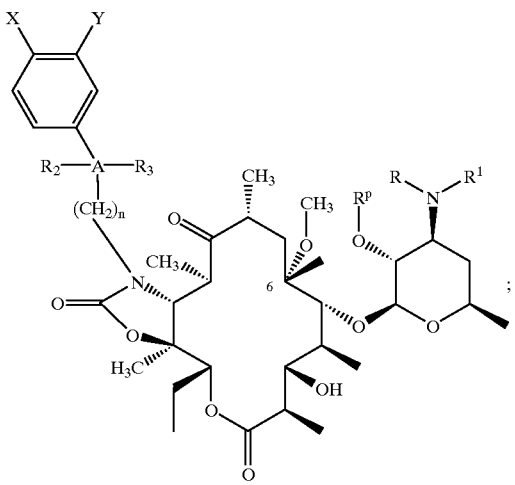

and (e) derivatizating the 3-hydroxy followed by deprotection of the 2'-hydroxy group.

The compounds of the invention exhibit little or no antibacterial activity, but they bind to the LHRH receptors and are effective LHRH antagonists. Thus, these compounds are effective in the treatment of prostate cancer, endometriosis, precocious puberty and other types of diseases which are related to sex hormones.

Accordingly, in another aspect of the invention, the present invention relates to pharmaceutical compositions which are useful as LHRH antagonists and suppress LH, testosterone, estradiol and estrogen in mammals.

In still another aspect, the present invention relates to a method of suppressing levels of sex hormones in male or female mammals comprising administering to a host in need of such treatment a therapeutically effective amount of a LHRH compound in combination with a therapeutically effective amount of an antiandrogenic agent.

DETAILED DESCRIPTION OF THE INVENTION

The terms "loweralkyl" or "alkyl" as used herein refer to straight or branched chain alkyl radicals containing from 1 to 20 carbon atoms, sometimes represented as Cx-Cy-alkyl where x and y respectively represent the minimum and maximum number of carbon atoms in the alkyl radical. Examples of loweralkyl include, but are not limited to, methyl, ethyl, n-propyl, isopropyl, n-butyl, isobutyl, sec-butyl, t-butyl, n-pentyl, 1-methylbutyl, 2,2-dimethylbutyl, 2-methylpentyl, 2,2-dimethylpropyl, n-hexyl and the like.

The term "alkoxy" or "lower alkoxy" as used herein refers to a loweralkyl group, as defined above, which is bonded to an oxygen atom in an ether linkage. Examples of alkoxy include, but are not limited to, methoxy, ethoxy, isopropoxy, n-pentyloxy, t-butoxy, n-octyloxy and the like. This alkoxy radical can also contain a ring which includes, but is not limited to, a five or six atom ring composed of carbons, which may contain one or two heteroatoms such as nitrogen, oxygen.

The term "alkenyl" as used herein refers to a branched or straight hydrocarbon chain comprising two to twenty carbon atoms, preferably four to twelve carbon atoms, especially about eight to ten carbon atoms, which also comprises one or more carbon-carbon double bonds, preferably about one to three double bonds. Compounds of the invention may either have a known configuration or may exist as a mixture of isomers.

The term "alkynyl" as used herein refers to a branched or straight hydrocarbon chain comprising two to twenty carbon atoms, preferably four to twelve carbon atoms, especially about eight to ten carbon atoms, which also comprises one or more carbon-carbon triple bonds, preferably about one triple bond. Compounds of the invention may either have a known configuration or may exist as a mixture of isomers.

The term "cycloalkyl" as used herein refers to a saturated monocyclic hydrocarbon group having from three to seven carbon atoms in the ring, including, but not limited to, cyclopropyl, cyclobutyl, cyclopentyl, cyclohexyl, cycloheptyl and the like. The cyclic group may be optionally substituted with, for example, lower alkyl, hydroxy, halogen or an amino group.

The term "alkylcycloalkyl" as used herein refers to a cycloalkyl group as defined above, appended to a loweralkyl radical. The alkylcycloalkyl group is attached to the parent moiety through the alkyl radical wherein the alkyl radical is of one to six carbon atoms. Examples include, but are not limited to, cyclopropylmethyl, cyclopropylethyl, cyclobutylmethyl and the like.

The term "aryl" as used herein refers to a mono-, fused bicyclic or fused tricyclic carbocyclic ring system having one or more aromatic rings including, but not limited to, phenyl, naphthyl, tetrahydronaphthyl, phenanthrenyl, biphenylenyl, indanyl, indenyl and the like.

The term "substituted aryl" as used herein refers to an aryl group as defined herein substituted by independent replacement of one, two or three of the hydrogen atoms thereon with Cl, Br, F, I, OH, cyano, mercapto, nitro, $C_1$-$C_3$-alkyl, halo-$C_1$-$C_3$-alkyl, $C_1$-$C_6$-alkoxy, thio-$C_1$-$C_6$-alkoxy, methoxymethoxy, amino, $C_1$-$C_3$-alkyl-amino, di($C_1$-$C_3$-alkyl-) amino, formyl, carboxy, alkoxycarbonyl, $C_1$-$C_3$-alkyl-CO—O—, $C_1$-$C_3$-alkyl-CO—NH—, or carboxamide; except that tetrafluorophenyl and pentafluorophenyl are also included within the definition of "substituted aryl".

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above. Examples include, but are not limited to, [3-(4-hydroxy)phenyl]propyl, [3-(1-methyl)(4-hydroxy)phenyl]propyl, (4-hydroxybenzyl)methyl, and the like.

The terms "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three nitrogen atoms; one nitrogen and one sulfur atom; or one nitrogen and one oxygen atom. The 5-membered ring has 0–2 double bonds and the 6- and 7-membered ring have 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring (for example, indolyl, quinolyl, isoquinolyl, tetrahydroquinolyl, and the like). Heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, piperazinyl, piperidinyl, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, thiazolidinyl, thiazolyl, and thienyl.

Heterocyclics can be unsubstituted or monosubstituted or disubstituted with substituents independently selected from hydroxy, halo, oxo (=O), alkylimino (R*N= wherein R* is a loweralkyl group), cycloalkyl, aryl, arylalkyl, and loweralkyl. In addition, nitrogen containing heterocycles can be N-protected.

The term "(heterocyclic)alkyl" as used herein refers to a heterocyclic group as defined above appended to a loweralkyl radical as defined above. The (heterocylic)alkyl group is attached to the parent moiety through an alkyl group wherein the alkyl group is of one to six carbon atoms. Examples include, but are not limited to, 2-pyridylmethyl, 4-pyridylmethyl, 2-(2-pyridyl)ethyl, 3-(3-pyridyl)propyl, 3-(2-pyridyl)propyl, 3-(4-pyridyl)propyl, 2-furylmethyl and the like.

The term "substituted (heterocyclic)alkyl" as used herein, refers to a heterocycloalkyl group, as defined above, wherein the heterocyclic group or the alkylgroup is substituted by independent replacement of one, two or three of the hydrogen atoms thereon with Cl, Br, F, I, OH, cyano, mercapto, nitro, $C_1$-$C_3$-alkyl, halo-$C_1$-$C_3$-alkyl, $C_1$-$C_6$-alkoxy, thio-$C_1$-$C_6$-alkoxy, hydroxyalkyl, methoxymethoxy, amino, $C_1$-$C_3$-alkyl-amino, di($C_1$-$C_3$-alkyl)amino, carboxaldehydo, carboxy, alkoxycarbonyl, $C_1$-$C_3$-alkyl-CO—O—, $C_1$-$C_3$-alkyl-CO—NH—, or carboxamide. Example include, but are not limited to, 3-[(5-methyl)-2-pyridyl]propyl, 3-[(6-methyl)-2-pyridyl]propyl, 4[(6-methyl)-2-pyridyl]butyl, (5-nitro)-2-thienylmethyl and the like.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isoxazolyl, thiadiazolyl, oxadiazolyl, thienyl, furanyl, quinolinyl, isoquinolinyl, and the like.

The term "substituted heteroaryl" as used herein refers to a heteroaryl group as defined herein substituted by independent replacement of one, two or three of the hydrogen atoms thereon with Cl, Br, F, I, OH, $C_1$-$C_3$-alkyl, $C_1$-$C_6$-alkoxy, methoxymethoxy, amino, or $C_1$-$C_3$-alkyl-amino, or may also refer to a mono-oxo substituted heteroaryl compound, such as 4oxo-1H-quinoline, for example.

The term "aprotic solvent" as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methyl-pyrrolidinone, ethers such as diethyl ether and bis-methoxymethyl ether, as well as various other compounds like dimethyl formamide, acetonitrile, acetone and ethyl acetate. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick, et al., Vol. II, in the Techniques of Chemistry Series, John Wiley & Sons, NY, 1986.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic or inorganic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refer to esters which hydrolyze in vivo and include those that break down readily in the human body to leave the parent compound or a salt therof. Suitable ester groups include, for example, those derived from pharmaceutically acceptable aliphatic carboxylic acid, particularly alkonoic, alkenoic, cycoalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present.

Preferred Embodiments

Preferred compounds of the invention of formula I are those wherein R and $R^1$ are a hydrogen, alkyl or cycloalkyl; X and Y are halogens, A is —C, and $R^2$ and $R^3$ are both hydrogen.

Representative compounds of the invention are selected from the group consisting of:

11-Deoxy-11-[carboxy-(4-chlorophenethyl)amino]-3-O-[4-(R)-methyl-oxazolidin-2-one] carbamoyl-5-O-(3'-N-desmethyl-3'-N-isopropyl)desosaminyl-6-O-methyl-erythronolide A 11,12-(cyclic carbamate);

11-Deoxy-11-[carboxy-(4-chlorophenethyl)amino]-3-O-[oxazolidin-2-one]carbamoyl-5-O-(3'-N-desmethyl-3'-N-isopropyl)desosaminyl-6-O-methyl-erythronolide A 11,12-(cyclic carbamate);

11-Deoxy-11-[carboxy-(4-chlorophenethyl)amino]-3-O-[4-(S)-ethyl-oxazolidin-2-one] carbamoyl-5-O-(3'-N-desmethyl-3'-N-isopropyl)desosaminyl-6-O-methyl-erythronolide A 11,12-(cyclic carbamate);

11-Deoxy-11-[carboxy-(4-chlorophenethyl)amino]-3-O-[4,5-(S,R)-dimethyl-oxazolidin-2-one]carbamoyl-5-O-(3'-N-desmethyl-3'-N-isopropyl)desosaminyl-6-O-methyl-erythronolide A 11,12-(cyclic carbamate);

11-Deoxy-11-[carboxy-(4-chlorophenethyl)amino]-3-O-[4,4-dimethyl-oxazolidin-2-one]carbamoyl-5-O-(3'-N-desmethyl-3'-N-isopropyl)desosaminyl-6-O-methyl-erythronolide A 11,12-(cyclic carbamate);

11-Deoxy-11-[carboxy(4-chlorophenethyl)amino]-5-O-(3'-N-desmethyl-3'-N-isopropyl)desosaminyl-3-O-[4-(s)-methyl-oxazolidin-2-one]carbamoyl-6-O-methyl-erythronolide A 11,12-(cyclic carbamate);

11-Deoxy-11-[carboxy(4-chlorophenethyl)amino]-5-O-(3'-bis-N-desmethyl-3'-N-isopropyl)desosaminyl-3-O-[4-(s)-methyl-oxazolidin-2-one]carbamoyl-6-O-methyl-erythronolide A 11,12-(cyclic carbamate);

11-Deoxy-11-[carboxy(4-chlorophenethyl)amino]-5-O-(3'-N-desmethyl-3'-N-isopropyl)desosaminyl-3-O-[4-(R)-methyl-oxazolidine]carbamoyl-6-O-methyl-erythronolide A 11,12-(cyclic carbamate);

11-Deoxy-11-[carboxy(4-chlorophenethyl)amino]-5-O-(3'-N-desmethyl-3'-N-isopropyl)desosaminyl-3-O-(tetrahydro-2-furoyl)-6-O-methyl-erythronolide A 11,12-(cyclic carbamate);

11-Deoxy-11-[carboxy(4-chlorophenethyl)amino]-5-O-(3'-bis-N-desmethyl-3'-N-isopropyl)desosaminyl-3-O-(tetrahydro-2-furoyl)-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-N-desmethyl-3'-N-cyclobutyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-N-desmethyl-3'-N-cyclopentyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-N-desmethyl-3'-N-cyclohexyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-N-desmethyl-3'-N-n-propyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-N-desmethyl-3'-N-isobutyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-N-desmethyl-3'-N-cyclobutylmethyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-N-desmethyl-3'-N-isopropyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-bis-N-desmethyl-3'-N-ethyl-3'-N-isopropyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-bis-N-desmethyl-3'-N-n-propyl-3'-N-isopropyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-bis-N-desmethyl-3'-N-cyclopropylmethyl-3'-N-isopropyl)desosaminyl-6-O-methyl-erythronolide A 11,12-(cyclic carbamate);

11-Deoxy-11-[carboxy(4-chlorophenethyl)amino]-3-O-[4-(s)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate);

11-Deoxy-11-[carboxy(4-chlorophenethyl)amino]-3-O-[4-(s)-methyl-oxazolidin-2-one]carbamoyl-5-O-(3'-N-desmethyl-3'-N-cyclobutyl)desosaminyl-6-O-methyl-erythronolide A 11,12-(cyclic carbamate);

11-Deoxy-11-[carboxy(4-chlorophenethyl)amino]-3-O-[4-(s)-methyl-oxazolidin-2-one]carbamoyl-5-O-(3'-N-desmethyl-3'-N-cyclopentyl)desosaminyl-6-O-methyl-erythronolide A 11,12-(cyclic carbamate);

11-Deoxy-11-[carboxy(4-chlorophenethyl)amino]-3-O-[4-(s)-methyl-oxazolidin-2-one]carbamoyl-5-O-(3'-N-desmethyl-3'-N-cyclohexyl)desosaminyl-6-O-methyl-erythronolide A 11,12-(cyclic carbamate);

11-Deoxy-11-[carboxy(4-chlorophenethyl)amino]-3-O-[4-(s)-methyl-oxazolidin-2-one]carbamoyl-5-O-(3'-N-desmethyl-3'-N-n-propyl)desosaminyl-6-O-methyl-erythronolide A 11,12-(cyclic carbamate);

11-Deoxy-11-[carboxy(4-fluorophenethyl)amino]-3-O-[4-(s)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate);

11-Deoxy-11-[carboxy(4-fluorophenethyl)amino]-3-O-[4-(s)-methyl-oxazolidin-2-one]carbamoyl-5-O-(3'-N-desmethyl-3'-N-cyclobutyl)desosaminyl-6-O-methyl-erythronolide A 11,12-(cyclic carbamate);

11-Deoxy-11-[carboxy(4-fluorophenethyl)amino]-3-O-[4-(s)-methyl-oxazolidin-2-one]carbamoyl-5-O-(3'-N-desmethyl-3'-N-cyclopentyl)desosaminyl-6-O-methyl-erythronolide A 11,12-(cyclic carbamate);

11-Deoxy-11-[carboxy(4-fluorophenethyl)amino]-3-O-[4-(s)-methyl-oxazolidin-2-one]carbamoyl-5-O-(3'-N-desmethyl-3'-N-n-propyl)desosaminyl-6-O-methyl-erythronolide A 11,12-(cyclic carbamate);

11-Deoxy-11-[carboxy(4-fluorophenethyl)amino]-3-O-[4-(s)-methyl-oxazolidin-2-one]carbamoyl-5-O-(3'-N-desmethyl-3'-N-isopropyl)desosaminyl-6-O-methyl-erythronolide A 11,12-(cyclic carbamate);

11-Deoxy-11-[carboxy(3-chloro-4-fluorophenethyl)amino]-3-O-[4-(s)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate);

11-Deoxy-11-[carboxy(3-chloro-4-fluorophenethyl)amino]-3-O-[4-(S)-methyl-oxazolidin-2-one]carbamoyl-5-O-(3'-N-desmethyl-3'-N-cyclobutyl)desosaminyl-6-O-methyl-erythronolide A 11,12-(cyclic carbamate);

11-Deoxy-11-[carboxy(3-chloro-4-fluorophenethyl)amino]-3-O-[4-(S)-methyl-oxazolidin-2-one]carbamoyl-5-O-(3'-N-desmethyl-3'-N-cyclopentyl)desosaminyl-6-O-methyl-erythronolide A 11,12-(cyclic carbamate);

11-Deoxy-11-[carboxy(4-chloro-3-fluorophenethyl)amino]-3-O-[4-(S)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate);

11-Deoxy-11-[carboxy(3,4-dichlorophenethyl)amino]-3-O-[4-(R)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate);

11-Deoxy-11-[carboxy(3,4-dichlorophenethyl)amino]-3-O-[4-(S)-ethyl-oxazolidin-2-one]carbamoyl-5-O-(3'-N-desmethyl-3'-N-cyclopropylmethyl)desosaminyl-6-O-methyl-erythronolide A 11,12-(cyclic carbamate);

11-Deoxy-11-[carboxy(3,4-dichlorophenethyl)amino]-3-O-[5-(R)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate);

11-Deoxy-11-[carboxy(3,4-dichlorophenethyl)amino]-3-O-[4-(S)-methyl-thiazolidin-2-one]carbamoyl-5-O-(3'-N-desmethyl-3'-N-cyclopropylmethyl)desosaminyl-6-O-methyl-erythronolide A 11,12-(cyclic carbamate);

11-Deoxy-11-[carboxy(3,4-dichlorophenethyl)amino]-3-O-[4-(S)-methyl-oxazolidin-2-thione]carbamoyl-5-O-(3'-N-desmethyl-3'-N-cyclopropylmethyl)desosaminyl-6-O-methyl-erythronolide A 11,12-(cyclic carbamate);

11-Deoxy-11-[carboxy(3,4-dichlorophenethyl)amino]-3-O-[4-(S)-methyl-oxazolidin-2-one]carbamoyl-5-O-(3'-bis-N-desmethyl-3'-bis-N-cyclopropylmethyl)desosaminyl-6-O-methyl-erythronolide A 11,12-(cyclic carbamate);

11-Deoxy-11-[carboxy(3-chloro-4-fluorophenethyl)amino]-3-O-[4-(S)-methyl-oxazolidin-2-one]carbamoyl-5-O-(3'-bis-N-desmethyl-3'-bis-N-cyclopropylmethyl)desosaminyl-6-O-methyl-erythronolide A 11,12-(cyclic carbamate);

11-Deoxy-11-[carboxy(4-chloro-3-fluorophenethyl)amino]-3-O-[4-(S)-methyl-oxazolidin-2-one]carbamoyl-5-O-(3'-bis-N-desmethyl-3'-bis-N-cyclopropylmethyl)desosaminyl-6-O-methyl-erythronolide A 11,12-(cyclic carbamate);

11-Deoxy-11-[carboxy(3,4-dichlorophenethyl)amino]-3-O-[4-(S)-methyl-oxazolidin-2-one]carbamoyl-5-O-(3'-bis-N-desmethyl-3'-N-cyclopropylmethyl)desosaminyl-6-O-methyl-erythronolide A 11,12-(cyclic carbamate);

11-Deoxy-11-[carboxy(3,4-dichlorophenethyl)amino]-3-O-[4-(S)-methyl-oxazolidin-2-one]carbamoyl-5-O-[3'-N-desmethyl-3'-N-[3-(2-pyridyl)propyl]desosaminyl-6-O-methyl-erythronolide A 11,12-(cyclic carbamate);

11-Deoxy-11-[carboxy(3,4-dichlorophenethyl)amino]-3-O-[4-(S)-methyl-oxazolidin-2-one]carbamoyl-5-O-[3'-N-desmethyl-3'-N-[(6-methyl-2-pyridyl)methyl]]desosaminyl-6-O-methyl-erythronolide A 11,12-(cyclic carbamate);

11-Deoxy-11-[carboxy(3,4-dichlorophenethyl)amino]-3-O-[4-(S)-methyl-oxazolidin-2-one]carbamoyl-5-O-[3'-bis-N-desmethyl-3'-[1-(2,5-dimethyl)pyrrolidinyl]]desosaminyl-6-O-methyl-erythronolide A 11,12-(cyclic carbamate);

11-Deoxy-11-[carboxy(3,4-dichlorophenethyl)amino]-3-O-[4-(S)-methyl-oxazolidin-2-one]carbamoyl-5-O-[3'-bis-N-desmethyl-3'-(1-piperidinyl)]desosaminyl-6-O-methyl-erythronolide A 11,12-(cyclic carbamate);

11-Deoxy-11-[carboxy[2-(N-methyl-4-chloroanilino)ethyl]amino]-3-O-[4-(R)-methyl-oxazolidin-2-one]carbamoyl-5-O-(3'-N-desmethyl-3'-N-isopropyl)desosaminyl-6-O-methyl-erythronolide A 11,12-(cyclic carbamate);

11-Deoxy-11-[carboxy(3-chlorophenoxyethyl)amino]-3-O-[4-(R)-methyl-oxazolidin-2-one]carbamoyl-5-O-(3'-N-desmethyl-3'-N-isopropyl)desosaminyl-6-O-methyl-erythronolide A 11,12-(cyclic carbamate); and 11-Deoxy-11-[carboxy(4-methoxyphenethyl)amino]-3-O-[4-(S)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate).

Effect and Utilities of LHRH Agonists and Antagonists

The LHRH agonist and antagonist compounds of the invention are useful for treatment of precocious puberty, prostate cancer, benign prostatic hyperplasia (BPH), endometriosis, uterine fibroids, breast cancer, acne, premenstrual syndrome, polycystic ovary syndrome and diseases which result from excesses or deficiencies in gonadal hormone production in either sex of humans and animals. The LHRH antagonists of the invention are also useful for controlling reproduction in both female and males. Compounds of the invention are useful for suppressing levels of testosterone and dihydrotestosterone (DHT) in male and estrogen and estradiol in female.

In the practice of the method of this invention an effective amount of a compound of the invention or a pharmaceutical composition containing the same is administered to the human or animal in need of, or desiring, such treatment. These compounds or compositions may be administered by any variety of routes depending upon the specific end use, including orally, parenterally (including subcutaneous, intramuscular and intravenous administration), vaginally (particularly for contraception), rectally, buccally (including sublingually), transdermally or intranasally. The most suitable route in any given case will depend upon the use, particular active ingredient, the subject involved, and the judgment of the medical practitioner. The compound or composition may also be administered by means of slow-release, depot or implant formulations as described more fully herein below.

In general, to modulate levels of sex hormones in male or female mammals for the uses herein above described, it is expedient to administer the active ingredient in amounts between about 1 and 200 mg/kg body weight per day, preferably between 1 and 30 mg/kg body weight per day. This administration may be accomplished by a single daily administration, by distribution over several applications or by slow release in order to achieve the most effective results.

The exact dose and regimen for administration of these compounds and compositions will necessarily be dependent upon the needs of the individual subject being treated, the type of treatment, the degree of afflication or need and the judgment of the medical practitioner. In general, parenteral administration requires lower dosage than other methods of administration which are more dependent upon absorption.

A further aspect of the present invention relates to pharmaceutical compositions containing as active ingredient a compound of the present invention which compositions comprise such compound in admixture with a pharmaceutically acceptable, non-toxic carrier. As mentioned above, such compositions may be prepared for use for parenteral (subcutaneous, intramuscular or intravenous) administration, particularly in the form of liquid solutions or suspensions; for use in vaginal or rectal administration, particularly in semisolid forms such as creams and suppositories; for oral or buccal administration, particularly in the form of tablets or capsules, or intranasally, particularly in the form of powders, nasal drops or aerosols.

The compositions may conveniently be administered in unit dosage form and may be prepared by any of the methods well-known in the pharmaceutical art, for example as described in Remington's Pharmaceutical Sciences, Mack Publishing Company, Easton, Pa., 1970. Formulations for parenteral administration may contain as common excipients sterile water or saline, polyalkylene glycols such as polyethylene glycol, oils of vegetable origin, hydrogenated naphthalenes and the like. Formulations for inhalation administration may be solid and contain as excipients, for example, lactose, or may be aqueous or oily solutions for administration in the form of nasal drops. For buccal administration typical excipients include sugars, calcium stearate, magnesium stearate, pregelatinated starch, and the like.

It is particularly desirable to deliver the compounds of the present invention to the subject over prolonged periods of time, for example, for periods of one week to one year from a single administration. Various slow release, depot or implant dosage forms may be utilized. For example, a dosage form may contain a pharmaceutically acceptable non-toxic salt of a compound of the invention which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a poly valent metal cation such as zinc, calcium, bismuth, barium, magnesium, aluminum, copper, cobalt, nickel, cadmium and the like, or with an organic cation formed from e.g., N,N'-debenzylethylenediamine or ethylenediamine; or (c) combinations of (a) and (b) e.g., a zinc tannate salt. Additionally, the compounds of the present invention or preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed or encapsulated in a slow degrading, non-toxic, non-antigenic polymer such as polylactic acid/polyglycolic acid polymer for example as described in U.S. Pat. No. 3,773,919. The compounds of the invention or, preferably, relatively insoluble salts such as those described above may also be formulated in cholesterol matrix pellets, particularly for use in animals. Additional slow release, depot or implant formulations, e.g. liposomes, are well known in the literature. See, for example, Sustained and Controlled Release Drug Delivery Systems, J. R. Robinson ed., Marcel Dekker, Inc., New York, 1978. Particular reference with respect to LHRH type compounds may be found, for example, in U.S. Pat. No. 4,010,125.

LHRH Antagonist Activity

Representative compounds of the present invention were evaluated in in vitro tests for LHRH rat pituitary receptor binding ($pK_I$) and for LH inhibition from rat pituitary cells for antagonist potency ($pA_2$). The tests employed the methods detailed in F. Haviv, et al. *J. Med. Chem.*, 32: 2340–2344 (1989). The receptor binding affinity ($pK_I$) is the negative logarithm of the equilibrium dissociation constants. The results of the $pK_I$ for representative compounds of this invention are presented in Table 1.

TABLE 1

| Example | $pK_I$ | Example | $pK_I$ |
|---------|--------|---------|--------|
| 1 | 8.28 | 25 | 8.93 |
| 2 | 8.67 | 26 | 9.78 |
| 3 | 8.20 | 27 | 9.60 |
| 4 | 8.05 | 28 | 9.50 |
| 5 | 8.54 | 29 | 9.98 |
| 6 | 8.54 | 30 | 9.89 |
| 7 | 8.45 | 31 | 9.02 |
| 8 | 7.93 | 32 | 9.81 |
| 9 | 7.85 | 33 | 9.97 |
| 10 | 8.09 | 34 | 10.08 |
| 11 | 8.50 | 35 | 9.07 |
| 12 | 9.17 | 36 | 8.43 |
| 13 | 8.51 | 37 | 8.27 |
| 14 | 9.16 | 38 | 8.17 |
| 15 | 8.41 | 39 | 8.55 |
| 16 | 8.40 | 40 | 8.09 |
| 17 | 9.25 | 41 | 7.99 |
| 18 | 9.03 | 42 | 9.18 |
| 19 | 9.63 | 43 | 9.16 |
| 20 | 9.23 | 44 | 8.50 |
| 21 | 9.61 | 45 | 8.09 |
| 22 | 10.13 | 54 | 8.83 |
| 23 | 8.84 | 55 | 9.50 |
| 24 | 9.60 | 56 | 9.92 |

Synthetic Methods

The compounds and processes of the present invention will be better understood in connection with the following synthetic Schemes 1–4 which illustrate the methods by which the compounds of the invention may be prepared. The compounds are prepared by utilizing commercially available or synthesized reagents.

Abbreviations

Abbreviations which have been used in the descriptions of the scheme and the examples that follow are: Ac for acetyl; Bz for benzoyl; Cbz for benzyloxycarbonyl; CDI for carbonyldiimidazole; DMAP for 4-dimethylaminopyridine; DMF for dimethyl formamide; LiHMDS for lithium bis(trimethylsilyl)amide; NaHMDS for sodium bis(trimethylsilyl)amide; TBAF for tetrabutylammonium fluoride; TEA for triethylamine; THF for tetrahydrofuran; and TMS for trimethylsilyl.

Scheme 1

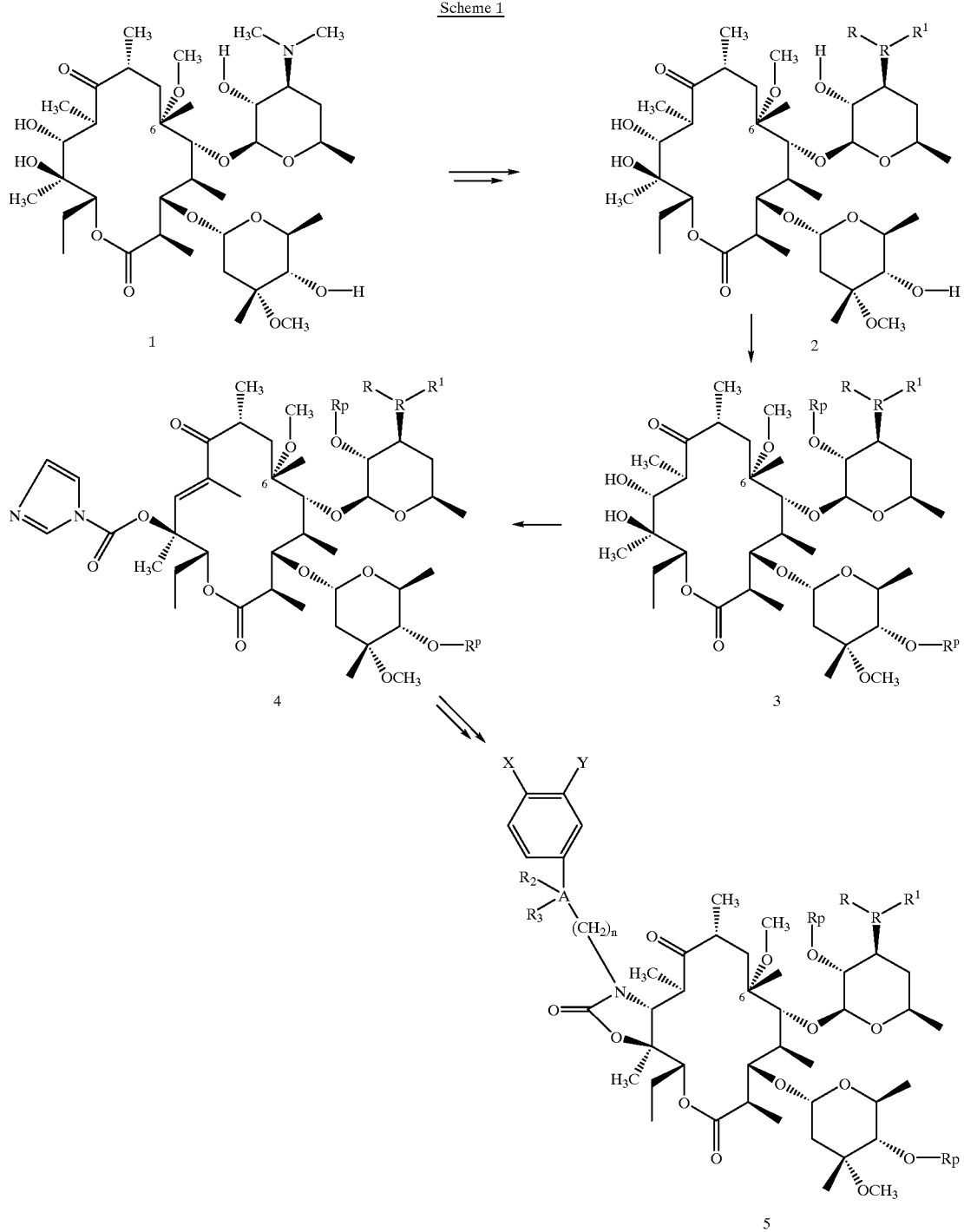

The starting material is 6-O-methyl-erythromycin A 1 (clarithromycin, commercially available as BIAXIN® from Abbott Laboratories).

Desmethylation of the 3'-N-dimethyl group of compound 1 is accomplished by treating compound 1 with iodine in the presence of a suitable base, such as sodium acetate and a light or a heat source, followed by quench with sodium thiosulfate and work up. N-dealkylation can also be accomplished utilizing chloroformate reagents such as benzyl chloroformate, allyl chloroformate, vinyl chloroformate and the like. One or both 3'-N-methyl groups can be removed in the process to afford either a secondary or a primary 3'-amino group.

Subsequent alkylation of the 3'-N-desmethyl derivative affords compound 2. This is achieved by reaction with an appropriate aldehyde or ketone in the presence of a borohydride reagent such as sodium cyanoborohydride or sodium triacetoxyborohydride or in the presence of Pd/C catalyst in a protic or non-protic solvent under hydrogen atmosphere. The aldehydes and ketones that may be used in preparing compound 2 include, for example, cyclopropyl carboxaldehyde, acetone, n-propanal, cyclohexanone, cyclopentanone, isovaleraldehyde, cyclobutanone, isopropylaldehyde, 2-pyridine-carboxyaldehyde, 4-thiazolecarboxaldehyde.

Alkylation of the 3'-N-desmethyl derivative can also be achieved by reaction with an appropriate alkylating agent in the presence of a base by the methods known in the art to afford compound 2. The alkylating agents which may be used in preparing compound 2 include loweralkyl halides such as ethyl bromide, halo-substituted loweralkyl halides, cyano-substituted loweralkyl halides, hydroxy-substituted loweralkyl halides, other loweralkenyl halides such as allyl chloride, loweralkynyl halides such as propargyl bromide, lower cycloalkyl halides, lower cycloalkylmethyl halides such as lower cyclopropylmethyl and benzyl halides.

Compound 2 is protected at the 2' and 4" positions by reaction with a suitable hydroxy protecting reagent, such as described by T. W. Greene and P. G. M. Wuts in *Protective Groups in Organic Synthesis*, 2nd. ed., John Wiley & Son, Inc. 1991. Hydroxy protecting reagents include, for example, acetic anhydride, benzoic anhydride, benzylchloroformate, hexamethyldisilazane, or trialkylsilyl chloride in an aprotic solvent.

Protection of 2'- and 4"-hydroxy groups of compound 2 as shown in Scheme 1 may be accomplished sequentially or simultaneously to provide compound 3 where RP is a hydroxy protecting group. A preferred protecting group RP is trimethylsilyl or acetyl.

Examples of aprotic solvents are dichloromethane, chloroform, DMF, tetrahydrofuran (THF), N-methyl pyrrolidinone, dimethylsulfoxide, diethylsulfoxide, N,N-dimethylformamide, N,N-dimethylacetamide, hexamethylphosphoric triamide, a mixture thereof or a mixture of one of these solvents with ether, tetrahydrofuran, 1,2-dimethoxyethane, acetonitrile, ethyl acetate, acetone and the like. Aprotic solvents do not adversely affect the reaction, and are preferably dichloromethane, chloroform, DMF, tetrahydrofuran (THF), N-methyl pyrrolidinone or a mixture thereof.

Compound 3 is then treated with sodium bis (trimethylsilyl)amide or sodium hydride in an aprotic solvent at 0–25° C. and carbonyldiimidazole to obtain compound 4. Treatment of compound 4 with an amino compound of the formula

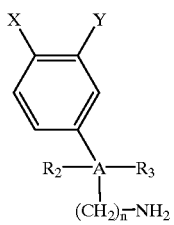

either without solvent or in acetonitrile at 25–80° C. yields compound 5.

Compound 5 is then acid hydrolyzed by methods known in the art to remove the cladinose sugar to afford compound 6. The hydroxyl group at position 3 is then acylated followed by removal of the 2'-hydroxy protecting group, to provide compound 7. The 3-position carbamates are prepared from compound 6 via the acylimidazole intermediate 8 obtained by reaction with CDI. Displacement of imidazole substituent with either a primary or secondary amine, or with an amide or carbamate in the presence of a strong base, followed by removal of the 2'-hydroxy protecting group affords compound 9. The deprotection is carried out using the methods described by T. W. Greene and P. G. M. Wuts in *Protective Groups in Organic Synthesis*, 2nd. ed., John Wiley & Son, Inc. 1991.

Scheme 1 contd.

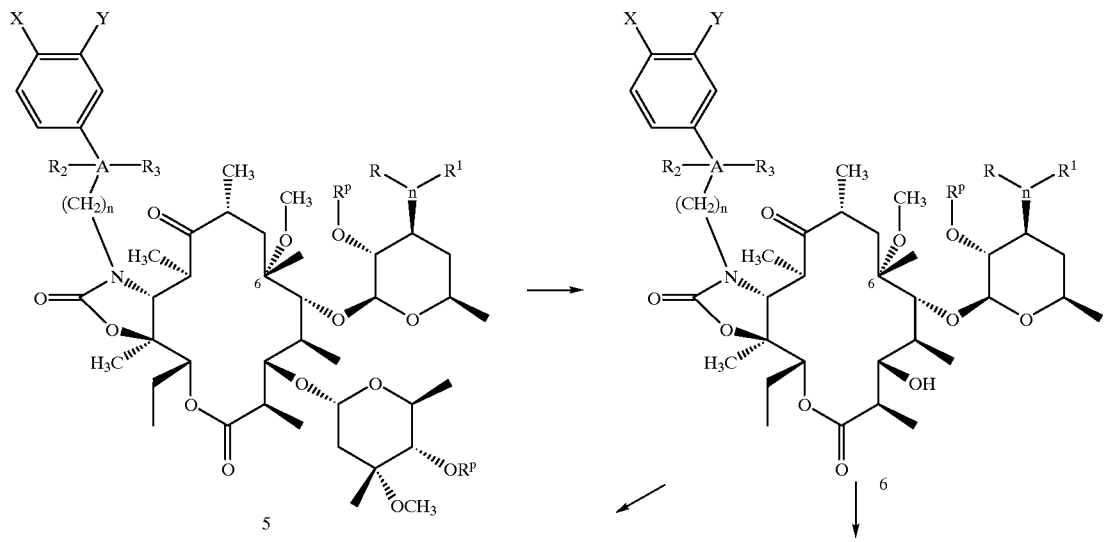

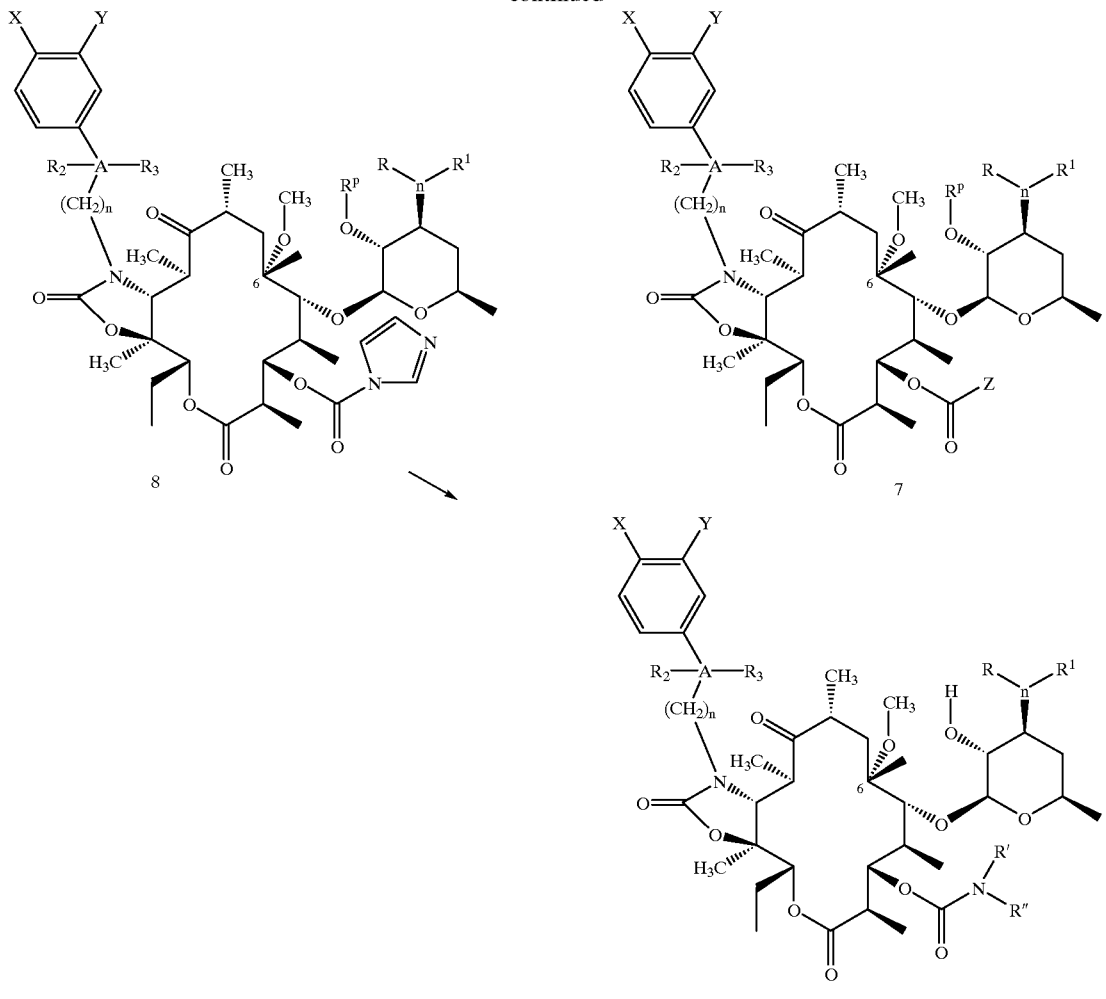

Alternatively, the protected compound 10 (Scheme 1A) may be first treated with sodium bis(trimethylsilyl)amide or sodium hydride in an aprotic solvent at 0–25° C. and carbonyldiimidazole to yield compound 3' as illustrated in Scheme 1A below. Treatment of compound 3' with an amino compound of the formula

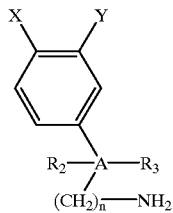

either without solvent or in acetonitrile at 25–80° C. affords compound 4'. Removal of the 2'- and 4"-hydroxy protecting groups of compound 4' yields compound 5'. Compound 5' is then demethylated by methods described above, followed by alkylation to obtain compound 6'. Compound 6' can then be further processed as previously described in Scheme 1.

Schemes 2, 3 and 4 that follow Scheme 1A illustrate the synthesis of specific embodiments of Examples 1, 11, 12 and 42, respectively, in accordance with the general method described above.

Scheme 1A
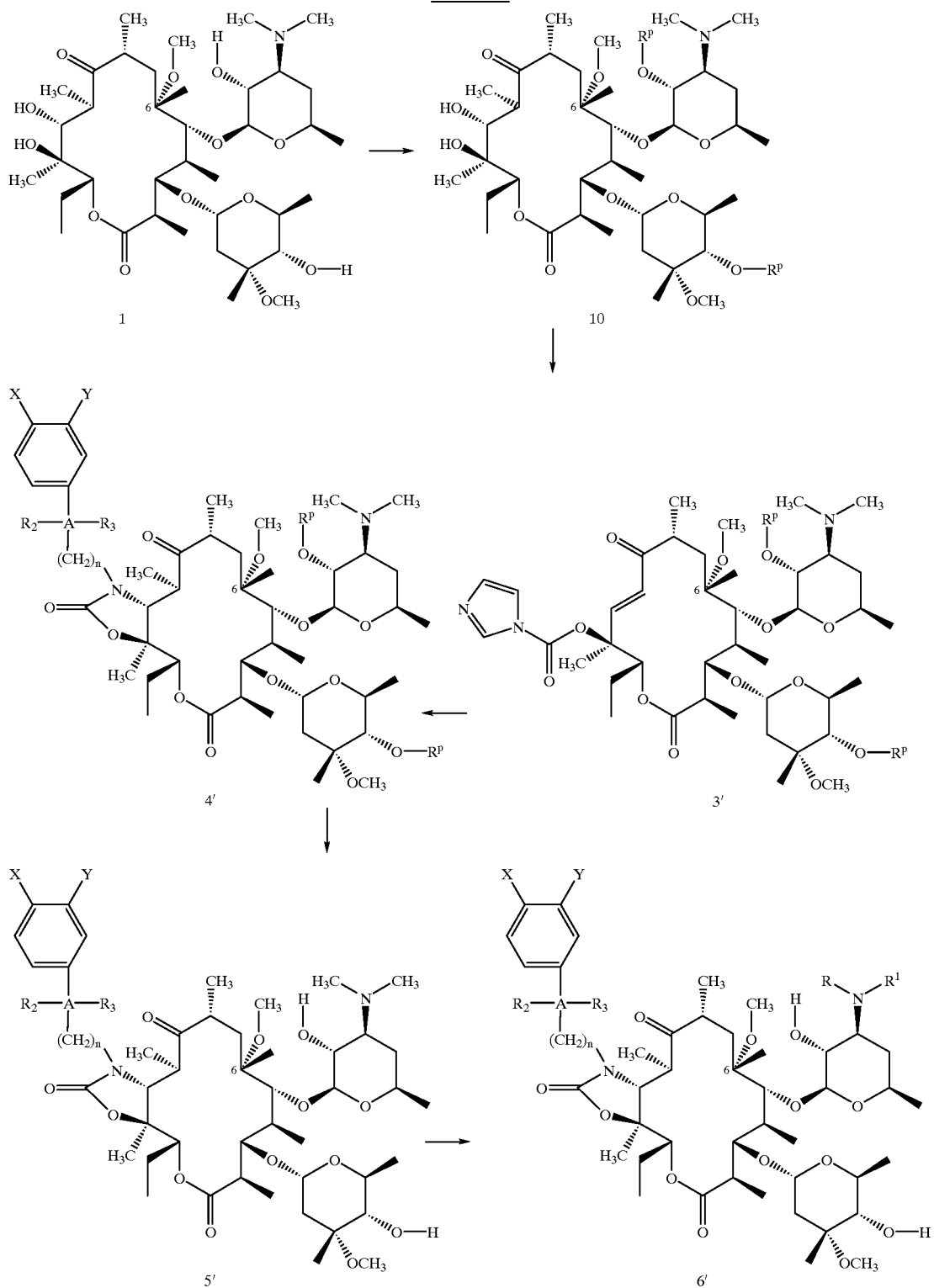

Scheme 2
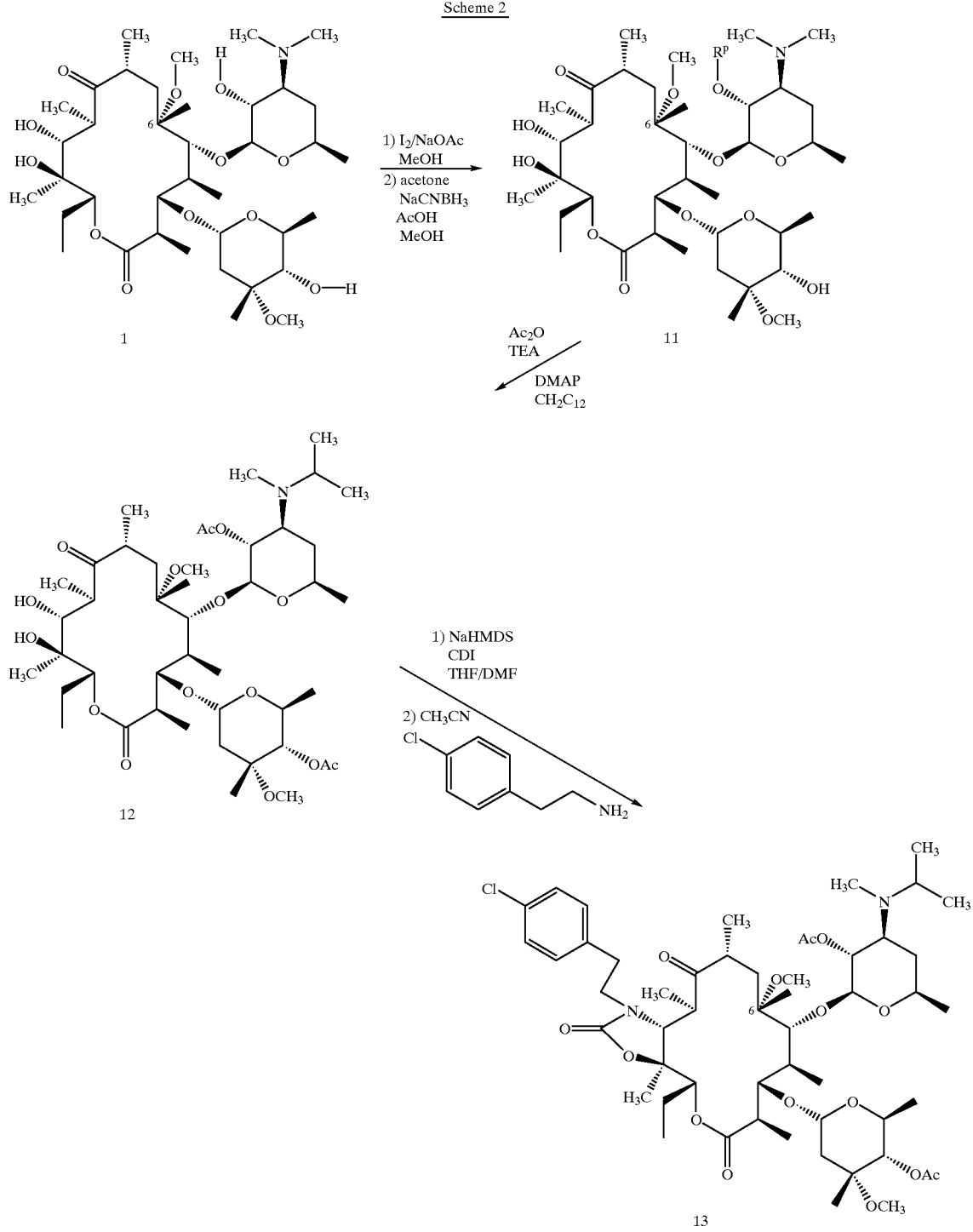

-continued
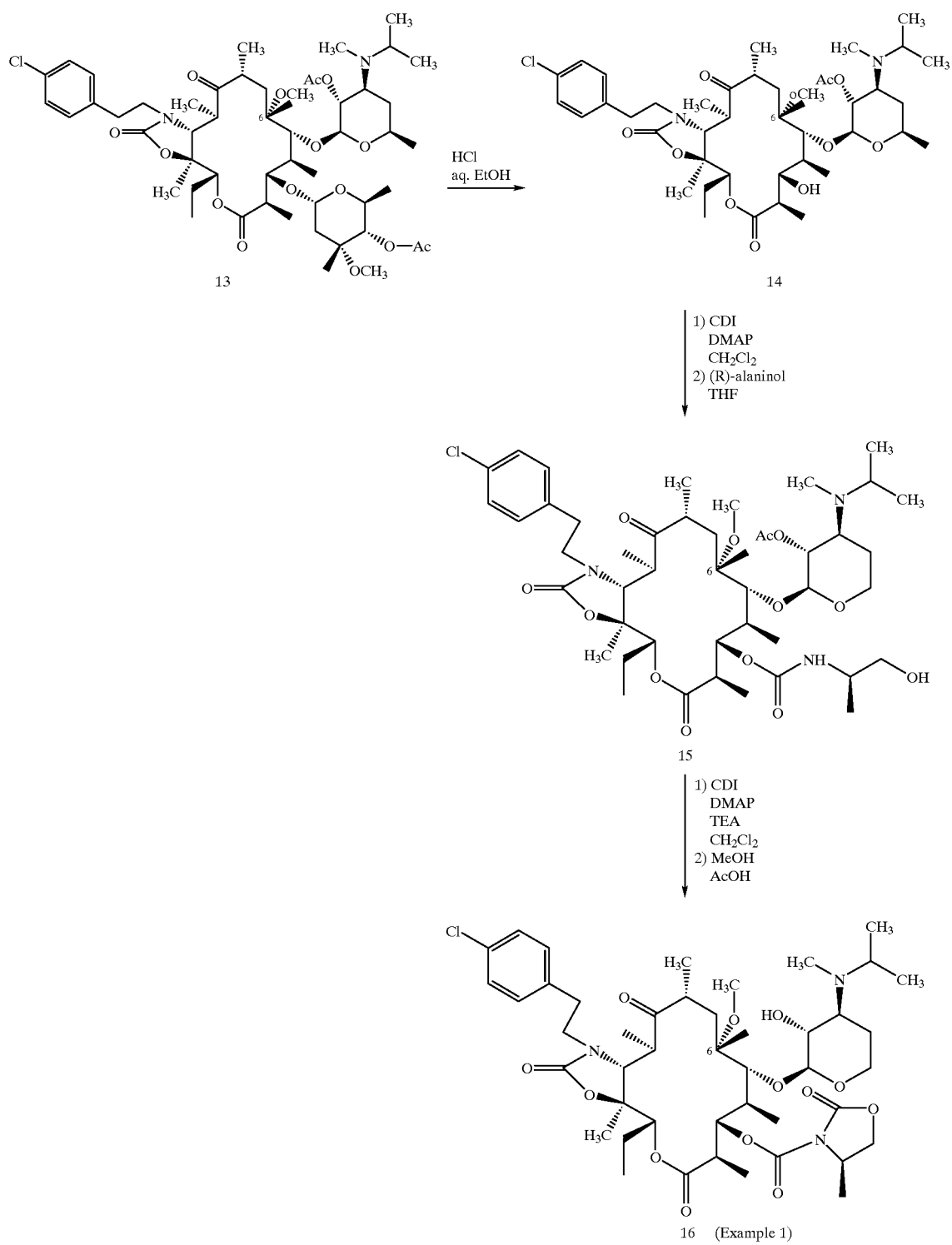

Scheme 3
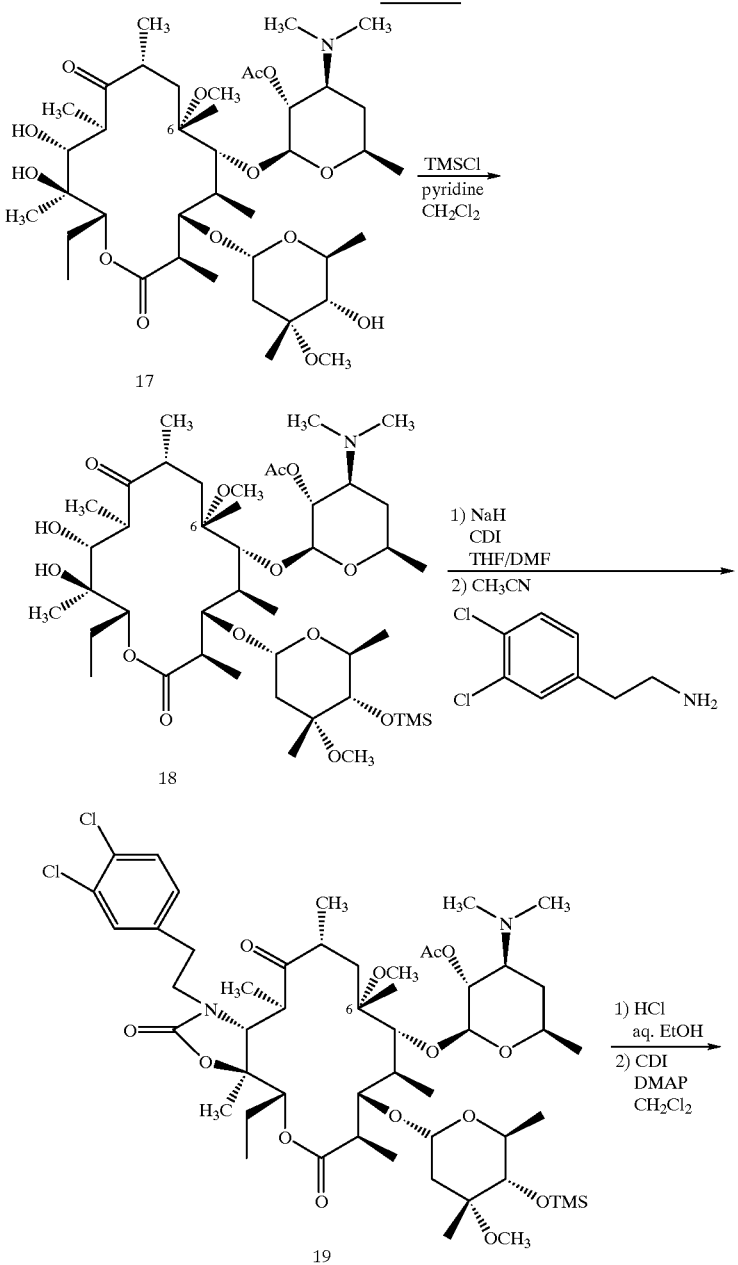

-continued
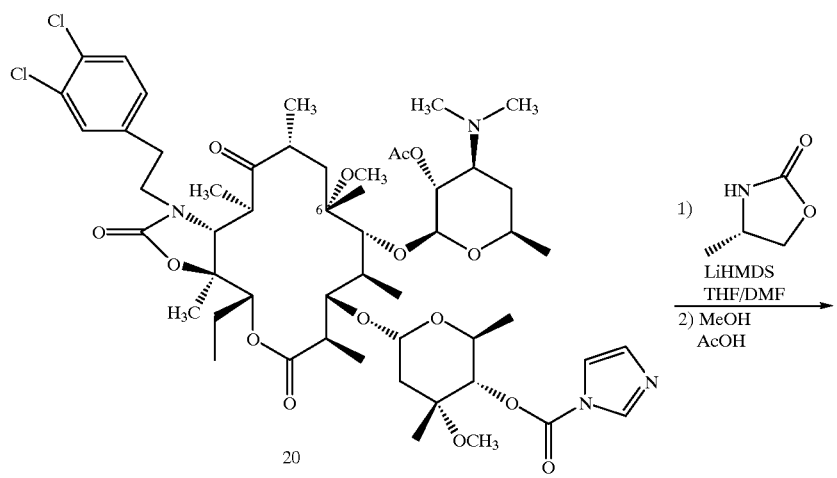
20
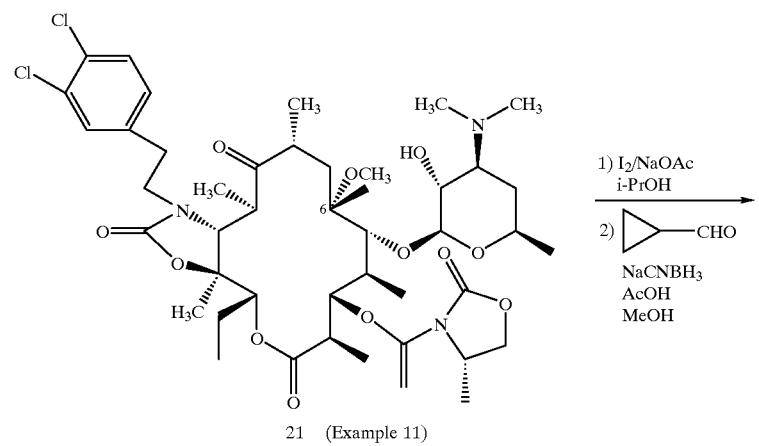
21 (Example 11)
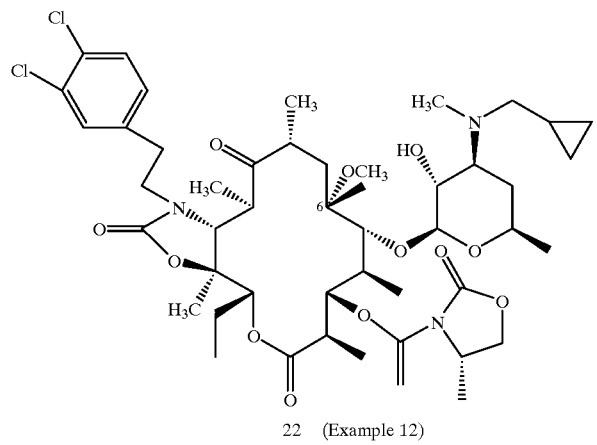
22 (Example 12)

Scheme 4
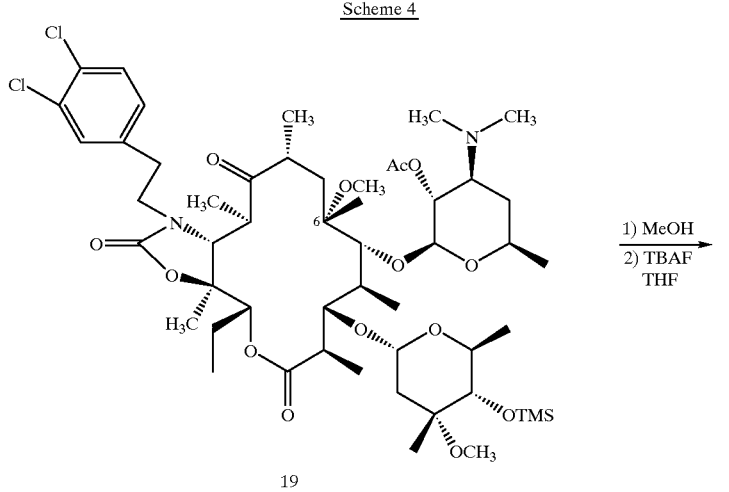
19
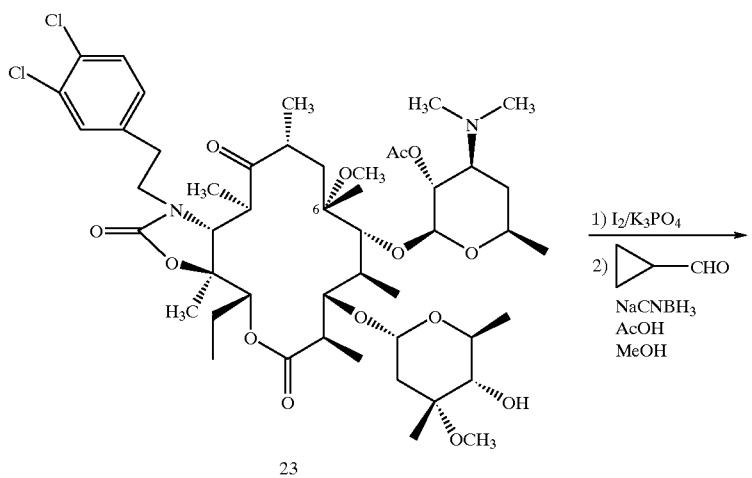
23
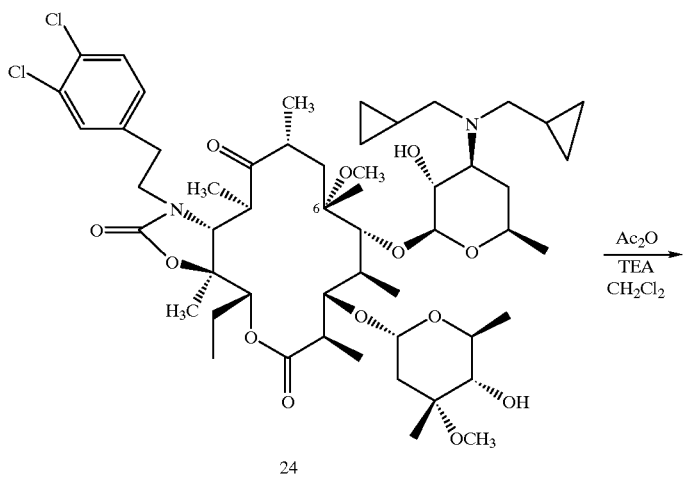
24

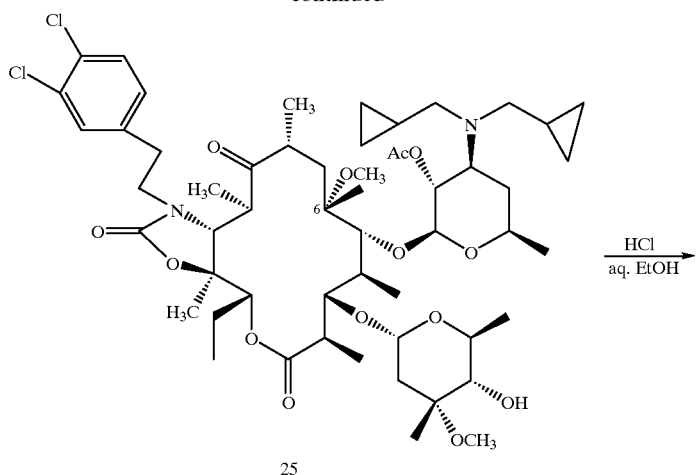

25

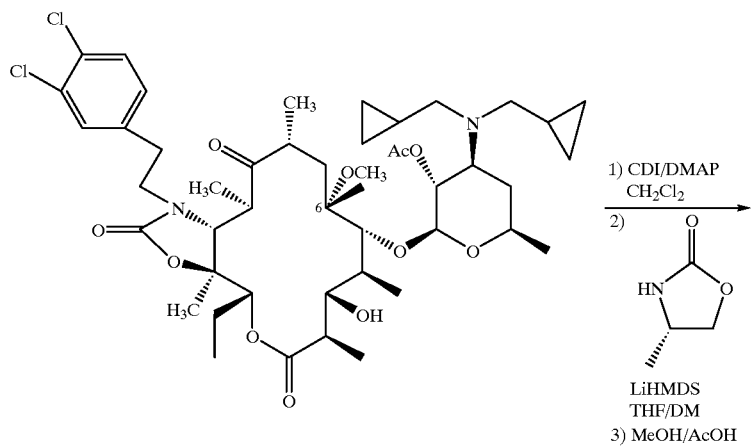

26

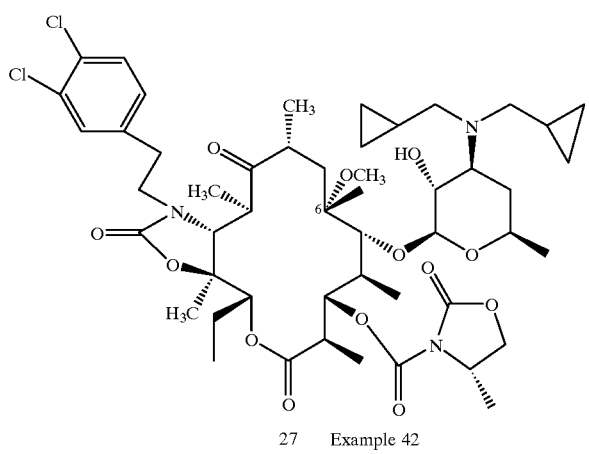

27  Example 42

The foregoing may be better understood by reference to the following examples which are presented for illustration and not to limit the scope of the inventive concept.

EXAMPLES

Example 1

11-Deoxy-11-[carboxy(4-chlorophenethyl)amino]-5-O-(3'-N-desmethyl-3'-N-isopropyl)desosaminyl-3-O-[4-(R)-methyl-oxazolidin-2-one]carbamoyl-6-O-methyl-erythronolide A 11,12-(cyclic carbamate) (Compound 16, Scheme 2)

Step 1: 3'-N-Desmethyl-3'-N-isopropyl-6-O-methyl-erythromycin A (Compound 11, Scheme 2)

To a solution of 6-O-methyl-erythromycin A (40.0 g, 53.5 mmol) in MeOH (120 mL) was added NaOAc.3H$_2$O (36.4 g, 267.5 mmol) and I$_2$ (13.7 g, 54.0 mmol). The dark colored reaction mixture was heated to reflux with stirring for 4 h, after which time the solution was colorless. More I$_2$ (2.7 g, 10.6 mmol) was added, and reflux was continued an additional 4 h until TLC (90:10:1 CHCl$_3$:MeOH:NH$_4$OH) indicated the reaction was complete. The mixture was concentrated to ca. 20 mL and diluted with CHCl$_3$ (500 mL), then washed with 0.2 M $Na_2S_2O_3$ (2×500 mL) and brine (500 mL) and dried over $Na_2SO_4$. The drying agent was filtered off, and solvent was removed in vacuo to give a crude product as an amorphous solid ($R_f$=0.25, 90:10:1 $CHCl_3$:MeOH:$NH_4OH$). To a solution of this compound in MeOH (500 mL) and acetone (100 mL) was added AcOH (3.1 mL, 54.2 mmol) and $NaCNBH_3$ (6.8 g, 108.2 mmol), and the reaction mixture was stirred at rt 2 days, after which time TLC (90:10:1 $CHCl_3$:MeOH:$NH_4OH$) indicated the reaction was complete. The mixture was concentrated and partitioned between $H_2O$ (500 mL) and $CHCl_3$ (3×400 mL), and the combined organics were dried over $Na_2SO_4$. The drying agent was filtered off, and solvent was removed in vacuo to give a crude product which crystallized from aq. $CH_3CN$ to give compound 11 as large colorless prisms (21.2 g). The filtrate was concentrated and purified by column chromatography on silica gel (97:3 $CHCl_3$:MeOH) to give additional compound 11 as a colorless, amorphous solid (14.5 g, total yield=35.7 g, 86%): mp=200–203° C.; $R_f$=0.70 (90:10:1 $CHCl_3$:MeOH:$NH_4OH$); $^{13}C$ NMR (75 MHz, $CDCl_3$) δ 220.9, 175.8, 102.9, 96.1, 80.8, 78.5, 78.0, 76.7, 74.3, 72.7, 70.5, 69.1, 68.8, 65.8, 62.9, 52.6, 50.6, 49.5, 45.3, 45.1, 39.4, 39.3, 37.3, 35.0, 33.2, 30.8, 21.5, 21.1, 20.5, 19.8, 18.7, 18.0, 16.0, 12.3, 10.6, 9.0; MS (CI) m/z 776 (M+H)$^+$.

Step 2: 2',4"-Di-O-acetyl-3'-N-desmethyl-3'-N-isopropyl-6-O-methyl-erythromycin A (Compound 12, Scheme 2)

To a solution of 3'-N-desmethyl-3'-N-isopropyl-6-O-methyl-erythromycin A (Compound 11) (32.12 g, 41.39 mmol) in anhydrous $CH_2Cl_2$ (200 mL) at 0° C. under dry $N_2$ was added triethylamine (14.0 mL, 100.44 mmol), acetic anhydride (9.00 mL, 95.39 mmol), and 4-dimethylaminopyridine (0.10 g, 0.82 mmol). The reaction mixture was allowed to warm to rt and stir for 20 h, after which time TLC (9:1 $CHCl_3$:MeOH) indicated the reaction was complete. The mixture was partitioned between 0.5 M $NaH_2PO_4$ (300 mL) and $CHCl_3$ (3×300 mL), and the combined organic layers were dried over $Na_2SO_4$. The drying agent was filtered off, and solvent was removed in vacuo to give a crude product which crystallized from $CH_3CN$ to give compound 12 as small colorless needles (24.9 g). The filtrate was concentrated and purified by column chromatography on silica gel (1:2 EtOAc:hexanes) to give additional compound 12 as a colorless, amorphous solid (5.7 g, total yield=30.6 g, 86%): mp=230–231° C.; $R_f$=0.65 (9:1 $CHCl_3$:MeOH); $^{13}C$ NMR (75 MHz, $CDCl_3$) δ 221.1, 175.5, 170.3, 169.8, 100.0, 95.8, 80.4, 78.6, 78.3, 77.8, 76.6, 74.2, 72.7, 71.8, 69.1, 67.3, 63.1, 59.1, 53.1, 50.5, 49.3, 45.3, 44.9, 38.7, 38.6, 37.2, 35.2, 34.9, 31.6, 21.6, 21.3, 21.2, 21.1, 20.8, 20.6, 19.7, 18.3, 18.0, 16.1, 16.0, 14.2, 12.3, 10.6, 9.0; MS (APCI) m/z 860 (M+H)$^+$.

Step 3: 2',4"-Di-O-acetyl-11-deoxy-11-[carboxy(4-chlorophenethyl)amino]-3'-N-desmethyl-3'-N-isopropyl-6-O-methyl-erythromycin A 11,12-(cyclic carbamate) (Compound 13, Scheme 2)

To a solution of 2',4"-di-O-acetyl-3'-N-desmethyl-3'-N-isopropyl-6-O-methyl-erythromycin A (Compound 12) (27.87 g, 32.40 mmol) in anhydrous THF (300 mL) at −40° C. under dry $N_2$ was added a solution of sodium bis(trimethylsilyl)amide (1.0 M in THF, 35.0 mL). The resulting solution was stirred at −40° C. 2 h, after which time a solution of 1,1'-carbonyldiimidazole (18.40 g, 113.5 mmol) in anhydrous 2:3 DMF:THF (200 mL) was added dropwise. The reaction mixture was allowed to warm to rt and stir 16 h, after which time TLC (9:1 $CHCl_3$:MeOH) indicated the reaction was complete. The mixture was poured into 0.5 M $NaH_2PO_4$ (500 mL) and extracted with EtOAc (3×400 mL), and the combined organic layers were dried over $Na_2SO_4$, filtered and concentrated to give an amorphous solid [$R_f$=0.55 (9:1 $CHCl_3$:MeOH), MS (APCI) m/z 936 (M+H)$^+$]. To a solution of this compound in $CH_3CN$ (30 mL) was added 4-chlorophenethylamine (14.0 mL, 100.0 mmol), and the reaction mixture was stirred at rt for 18 h, after which time TLC (9:1 $CHCl_3$:MeOH) indicated the reaction was complete. The mixture was poured into 0.5 M $NaH_2PO_4$ (500 mL) and extracted with EtOAc (3×300 mL), and the combined organic layers were dried over $Na_2SO_4$. The drying agent was filtered off, and solvent was removed in vacuo to give a crude product which crystallized from $CHCl_3$/hexanes to give compound 13 as large, colorless prisms (21.15 g). The filtrate was concentrated and purified by column chromatography on silica gel (1:1 EtOAc:hexanes) to give additional compound 13 as a colorless, amorphous solid (3.20 g, total yield=24.35 g, 73%): mp=135–142° C.; $R_f$=0.75 (9:1 $CHCl_3$:MeOH); $^{13}C$ NMR (75 MHz, $CDCl_3$) δ 216.2, 176.0, 170.3, 169.7, 157.2, 137.4, 131.9, 130.3, 128.5, 100.2, 95.9, 82.7, 79.8, 78.8, 78.6, 77.4, 76.3, 72.7, 71.9, 67.4, 63.2, 60.4, 59.1, 53.2, 50.6, 49.3, 45.6, 45.1, 45.0, 39.0, 38.5, 35.2, 34.9, 32.8, 31.5, 22.0, 21.6, 21.3, 21.2, 20.8, 20.6, 20.1, 18.9, 18.3, 16.0, 14.4, 14.2, 10.2, 8.9; MS (APCI) m/z 1023 (M+H)$^+$.

Step 4: 11-Deoxy-11-[carboxy(4-chlorophenethyl)amino]-5-O-(2'-O-acetyl-3'-N-desmethyl-3'-N-isopropyl)desosaminyl-6-O-methyl-erythronolide A 11,12-(cyclic carbamate) (Compound 14, Scheme 2)

A solution of 2',4"-di-O-acetyl-11-deoxy-11-[carboxy(4-chlorophenethyl)amino]-3'-N-desmethyl-3'-N-isopropyl-6-O-methyl-erythromycin A 11, 12-(cyclic carbamate) (Compound 13) (23.25 g, 22.7 mmol) in 1:1 N HCl:EtOH (800 mL) was stirred at rt 4 days, after which time TLC (9:1 $CHCl_3$:MeOH) indicated the reaction was complete. 2 N NaOH was carefully added to adjust to pH 4, and the resulting solution was extracted with $CHCl_3$ (3×400 mL). The combined organic layers were dried over $Na_2SO_4$, then filtered and concentrated to give a crude product which was purified by column chromatography on silica gel (1:1 EtOAc:hexanes) to give compound 14 as a colorless, amorphous solid (15.9 g, 85%): $R_f$=0.45 (9:1 $CHCl_3$:MeOH); $^{13}C$ NMR (75 MHz, $CDCl_3$) δ 215.8, 175.1, 169.8, 157.1, 137.3, 131.9, 130.3, 128.5, 100.2, 82.8, 80.9, 78.5, 77.6, 76.3, 71.5, 69.0, 60.7, 59.5, 53.1, 49.9, 45.8, 45.0, 44.2, 38.9, 38.4, 35.9, 34.9, 32.8, 31.3, 22.2, 21.3, 21.2, 21.0, 20.7, 19.4, 18.9, 15.2, 14.3, 10.1, 7.7; MS (FAB) m/z 823 (M+H)$^+$.

Step 5: 11-Deoxy-11-[carboxy(4-chlorophenethyl)amino]-3-O-[2-(R)-amino-1-propanol]carbamoyl-5-O-(2'-O-acetyl-3'-N-desmethyl-3'-N-isopropyl)desosaminyl-6-O-methyl-erythronolide A 11,12-(cyclic carbamate) (Compound 15, Scheme 2)

To a solution of 11-deoxy-11-[carboxy(4-chlorophenethyl)amino]-5-O-(2'-O-acetyl-3'-N-desmethyl-3'-N-isopropyl)desosaminyl-6-O-methyl-erythronolide A 11, 12-(cyclic carbamate) (Compound 14) (5.00 g, 6.07 mmol) in anhydrous $CH_2Cl_2$ (50 mL) at 0° C. under dry $N_2$ was added 1,1'-carbonyldiimidazole (2.00 g, 12.33 mmol) and 4-dimethylaminopyridine (0.75 g, 6.14 mmol). The reaction mixture was allowed to warm to rt and stir 3 days, after which time TLC (9:1 $CHCl_3$:MeOH) indicated the reaction was complete. The mixture was partitioned between 0.5 M $NaH_2PO_4$ (200 mL) and $CHCl_3$ (3×150 mL), and the combined organic layers were dried over $Na_2SO_4$. The drying agent was filtered off, and solvent was removed in vacuo to give a crude product which was purified by column chromatography on silica gel (3:1 EtOAc:hexanes) to give the 3-O-acylimidazole derivative of compound 14 as a colorless, amorphous solid [(4.64 g, 83%), $R_f$=0.65 (9:1

CHCl$_3$:MeOH), MS (APCI) m/z 917 (M+H)$^+$]. To a solution of this compound (1.00 g, 1.09 mmol) in anhydrous THF (2 mL) was added D-alaninol (0.2 mL, 25.7 mmol). The reaction mixture was stirred at rt for 2 days, after which time TLC (9:1 CHCl$_3$:MeOH) indicated the reaction was complete. The mixture was partitioned between saturated aq. NH$_4$Cl (100 mL) and CHCl$_3$ (3×50 mL), and the combined organic layers were dried over Na$_2$SO$_4$. The drying agent was filtered off, and solvent was removed in vacuo to give a crude product which was purified by column chromatography on silica gel (97:3 CHCl$_3$:MeOH) to give compound 15 as a colorless, amorphous solid (0.64 g, 63%): R$_f$=0.30 (9:1 CHCl$_3$:MeOH); $^{13}$C NMR (75 MHz, CDCl$_3$) δ 215.7, 174.2, 169.7, 157.1, 156.5, 137.3, 131.9, 130.3, 128.5, 100.7, 82.8, 79.6, 78.4, 78.1, 76.5, 71.5, 69.2, 66.7, 60.6, 59.8, 53.0, 50.2, 48.9, 45.7, 45.0, 43.3, 38.9, 38.3, 35.6, 34.8, 32.7, 31.4, 22.1, 21.3, 21.1, 20.6, 19.4, 19.0, 17.3, 14.8, 14.3 (2C), 10.1, 8.7; MS (APCI) m/z 924 (M+H)$^+$.

Step 6: 11-Deoxy-11-[carboxy(4-chlorophenethyl)amino]-5-O-(3'-N-desmethyl-3'-N-isopropyl)desosaminyl-3-O-[4-(R)-methyl-oxazolidin-2-one]carbamoyl-6-O-methyl-erythronolide A 11,12-(cyclic carbamate) (Compound 16, Scheme 2)

To a solution of 11-deoxy-11-[carboxy(4-chlorophenethyl)amino]-3-O-[2-(R)-amino-1-propanol] carbamoyl-5-O-(2'-O-acetyl-3'-N-desmethyl-3'-N-isopropyl)desosaminyl-6-O-methyl-erythronolide A 11,12-(cyclic carbamate) (Compound 15) (270 mg, 0.29 mmol) in anhydrous CH$_2$Cl$_2$ (3 mL) at 0° C. under dry N$_2$ was added 1,1'-carbonyldiimidazole (100 mg, 0.62 mmol) and 4-dimethylaminopyridine (36 mg, 0.29 mmol). The reaction mixture was allowed to warm to rt and stir 8 h, after which time TLC (9:1 CHCl$_3$:MeOH) indicated complete conversion to a less polar product (R$_f$=0.45). Triethylamine (0.20 mL, 1.43 mmol) was added, and the reaction flask was sealed and warmed to 40° C. with stirring for 2 days, after which time TLC (9:1 CHCl$_3$:MeOH) indicated the reaction was complete. The mixture was partitioned between saturated aq. NH$_4$Cl (40 mL) and CHCl$_3$ (3×30 mL), and the combined organic layers were dried over Na$_2$SO$_4$. The drying agent was filtered off, and solvent was removed in vacuo to give a crude product which was purified by column chromatography on silica gel (1:1 EtOAc:hexanes) to give the 2'-O-acetate of compound 16 as a colorless, amorphous solid [(205 mg, 74%), R$_f$=0.65 (9:1 CHCl$_3$:MeOH), MS (FAB) m/z 950 (M+H)$^+$]. A solution of this compound (180 mg, 0.19 mmol) in MeOH (5 mL) and AcOH (10 μL) was stirred at rt 16 h, after which time TLC (9:1 CHCl$_3$:MeOH) indicated the reaction was complete. The solvent was removed in vacuo and the crude product was purified by column chromatography on silica gel (97:3 CHCl$_3$:MeOH) to give compound 16 as a colorless, amorphous solid (165 mg, 96%): R$_f$=0.30 (9:1 CHCl$_3$:MeOH); IR (microscope) υ 3475, 2980, 1825, 1760, 1735, 1715, 1460, 1385, 1355, 1280, 1235, 1170, 1105, 1065 cm$^{-1}$; $^{13}$C NMR (75 MHz, CDCl$_3$) δ 215.7, 173.8, 157.0, 150.8, 137.1, 131.8, 130.3, 128.5, 104.3, 82.7, 82.4, 81.2, 78.5, 76.9, 70.0, 69.6, 68.5, 64.0, 60.7, 52.7, 51.1, 50.1, 45.6, 45.0, 43.1, 38.9, 38.7, 36.3, 32.8 (2C), 30.9, 22.1, 21.2, 20.8, 20.0, 19.6, 18.9, 15.3, 14.3 (2C), 10.1, 9.0; MS (FAB) m/z 908 (M+H)$^+$; Anal. Calcd for C$_{46}$H$_{70}$ClN$_3$O$_{13}$·H$_2$O (926.534): C, 59.63; H, 7.83; N, 4.54. Found: C, 59.37; H, 7.65; N, 4.37.

Example 2
11-Deoxy-11-[carboxy(4-chlorophenethyl)amino]-5-O-(3'-N-desmethyl-3'-N-isopropyl)desosaminyl-3-O-[oxazolidin-2-one]carbamoyl-6-O-methyl-erythronolide A 11,12-(cyclic carbamate)

The title compound was prepared following the procedure described in Scheme 2, substituting ethanolamine for D-alaninol. The crude product was purified by silica gel column chromatography (97:3 CHCl$_3$:MeOH) to give a colorless, amorphous solid: R$_f$0.30 (9:1 CHCl$_3$:MeOH); IR (KBr) μ 3440, 2975, 1825, 1760, 1740, 1460, 1385, 1325, 1310, 1235, 1170, 1070, 1040 cm$^{-1}$; $^{13}$C NMR (75 MHz, CDCl$_3$) δ 215.6, 173.8, 157.1, 150.8, 137.3, 132.0, 130.3, 128.5, 104.5, 82.7, 82.2, 81.4, 78.6, 77.0, 69.9, 69.6, 63.6, 61.6, 60.8, 53.0, 50.1, 50.3, 45.7, 45.0, 43.3, 43.0, 39.0, 38.7, 38.6, 36.4, 32.8, 30.6, 22.1, 21.2, 19.6, 19.5, 18.9, 15.2, 14.4, 14.3, 10.1, 8.9; MS (APCI) m/z 894 (M+H)$^+$; Anal. Calcd for C$_{45}$H$_{68}$ClN$_3$O$_{13}$ (894.493): C, 60.42; H, 7.66; N, 4.70. Found: C, 60.37; H, 7.83; N, 4.44.

Example 3
11-Deoxy-11-[carboxy(4-chlorophenethyl)amino]-5-O-(3'-N-desmethyl-3'-N-isopropyl)desosaminyl-3-O-[4-(S)-ethyl-oxazolidin-2-one]carbamoyl-6-O-methyl-erythronolide A 11,12-(cyclic carbamate)

The title compound was prepared following the procedure described in Scheme 2, substituting (S)-2-amino-1-butanol for D-alaninol. The crude product was purified by silica gel column chromatography (97:3 CHCl$_3$:MeOH) to give a colorless, amorphous solid: R$_f$0.35 (9:1 CHCl$_3$:MeOH); IR (KBr) υ 3440, 2965, 1825, 1795, 1760, 1740, 1460, 1380, 1365, 1310, 1170, 1110, 1065 cm$^{-1}$; $^{13}$C NMR (75 MHz, CDCl$_3$) δ 215.8, 174.0, 157.0, 151.4, 137.3, 131.8, 130.3, 128.5, 102.8, 82.7, 81.3, 79.6, 78.5, 76.8, 70.0, 69.7, 69.2, 66.3, 62.9, 60.6, 56.1, 50.3, 45.7, 45.0, 43.0, 38.9, 38.5, 36.4, 33.2, 32.8, 31.1, 22.0, 21.2, 19.6, 18.9, 15.1, 14.3, 10.1, 8.9, 8.1; MS (APCI) m/z 922 (M+H)$^+$; Anal. Calcd for C$_{47}$H$_{72}$ClN$_3$O$_{13}$·0.2CHCl$_3$ (946.421): C, 59.90; H, 7.69; N, 4.44. Found: C, 59.69; H, 7.59; N, 3.98.

Example 4
11-Deoxy-11-[carboxy(4-chlorophenethyl)amino]-5-O-(3'-N-desmethyl-3'-N-isopropyl)desosaminyl-3-O-[4,4-dimethyl-oxazolidin-2-one]carbamoyl-6-O-methyl-erythronolide A 11,12-(cyclic carbamate)

The title compound was prepared following the procedure described in Scheme 2, substituting 2-amino-2-methyl-1-propanol for D-alaninol. The crude product was purified by silica gel column chromatography (97:3 CHCl$_3$:MeOH), and the product crystallized upon concentration: mp=144–148° C.; R$_f$0.35 (9:1 CHCl$_3$:MeOH); IR (KBr) υ 3435, 2965, 1815, 1790, 1755, 1735, 1460, 1380, 1315, 1285, 1230, 1170, 1070, 1040 cm$^{-1}$; $^{13}$C NMR (75 MHz, CDCl$_3$) δ 215.9, 174.1, 157.1, 151.6, 137.3, 131.7, 130.3, 128.5, 102.5, 82.8, 80.8, 79.2, 78.5, 76.8, 74.8, 70.1, 69.4, 62.6, 60.5, 59.9, 52.6, 50.4, 45.7, 45.0, 43.0, 38.9, 38.6, 36.3, 33.2, 32.8, 30.9, 25.1, 24.8, 22.0, 21.3, 20.9, 20.4, 19.6, 19.0, 15.0, 14.3, 14.2, 10.1, 9.0; MS (APCI) m/z 922 (M+H)$^+$; Anal. Calcd for C$_{47}$H$_{72}$ClN$_3$O$_{13}$·2.0H$_2$O (958.575): C, 58.89; H, 7.99; N, 4.38. Found: C, 58.88; H, 7.66; N, 4.34.

Example 5
11-Deoxy-11-[carboxy(4-chlorophenethyl)amino]-5-O-(3'-N-desmethyl-3'-N-isopropyl)desosaminyl-3-O-[4,5-(S,R)-dimethyl-oxazolidin-2-one]carbamoyl-6-O-methyl-erythronolide A 11,12-(cyclic carbamate)

The title compound was prepared following the procedure described in Scheme 2, substituting 3-(S)-amino-2-(R)-butanol for D-alaninol. The crude product was purified by silica gel column chromatography (97:3 CHCl$_3$:MeOH) to give a colorless, amorphous solid: R$_f$0.40 (9:1 CHCl$_3$:MeOH); IR (KBr) υ 3440, 2970, 1820, 1795, 1760, 1740, 1460, 1365, 1170, 1105, 1070 cm$^{-1}$; $^{13}$C NMR (125

MHz, CDCl$_3$) δ 215.8, 174.0, 157.1, 151.2, 151.0, 137.2, 131.9, 130.3, 128.4, 103.1, 82.7, 81.3, 80.3, 78.5, 76.8, 74.0, 69.6, 69.2, 63.0, 60.6, 55.1, 50.1, 45.6, 45.0, 43.0, 38.9, 38.5, 36.4, 33.1, 32.7, 31.3, 22.0, 21.1, 20.3, 19.8, 19.5, 18.8, 15.1, 14.2 (2C), 13.6, 10.1, 8.9; MS (ESI) m/z 922 (M+H)$^+$; Anal. Calcd for C$_{47}$H$_{72}$ClN$_3$O$_{13}$.0.75H$_2$O (931.554): C, 60.30; H, 7.91; N, 4.48. Found: C, 60.26; H, 7.73; N, 4.48.

Example 6

11-Deoxy-11-[carboxy(4-chlorophenethyl)amino]-5-O-(3'-N-desmethyl-3'-N-isopropyl)desosaminyl-3-O-[4-(s)-methyl-oxazolidin-2-one]carbamoyl-6-O-methyl-erythronolide A 11,12-(cyclic carbamate)

The title compound was prepared following the procedure described in Scheme 2, substituting L-alaninol for D-alaninol. The crude product was purified by silica gel column chromatography (97:3 CHCl$_3$:MeOH) to give a colorless, amorphous solid: R$_f$0.35 (9:1 CHCl$_3$:MeOH); IR (KBr) υ 3430, 2965, 1820, 1795, 1750, 1730, 1455, 1380, 1350, 1305, 1165, 1100, 1060, 1045 cm$^{-1}$; $^{13}$C NMR (75 MHz, CDCl$_3$) δ 215.8, 174.0, 157.1, 151.3, 137.3, 131.9, 130.3, 128.5, 103.0, 82.7, 81.3, 79.6, 78.5, 76.8, 70.0, 69.7, 68.6, 62.9, 60.6, 52.6, 51.5, 50.3, 45.7, 45.0, 43.0, 38.9, 38.5, 36.4, 33.1, 32.8, 30.9, 22.0, 21.2, 19.8, 19.6, 18.9, 15.1, 14.3, 10.1, 8.9; MS (ESI) m/z 908 (M+H)$^+$; Anal. Calcd for C$_{46}$H$_{70}$ClN$_3$O$_{13}$.0.15CHCl$_3$ (926.425): C, 59.83; H, 7.63; N, 4.54. Found: C, 59.65; H, 7.35; N, 4.44.

Example 7

11-Deoxy-11-[carboxy(4-chlorophenethyl)amino]-5-O-(3'-bis-N-desmethyl-3'-N-isopropyl)desosaminyl-3-O-[4-(s)-methyl-oxazolidin-2-one]carbamoyl-6-O-methyl-erythronolide A 11,12-(cyclic carbamate)

To a solution of 11-deoxy-11-[carboxy(4-chlorophenethyl)amino]-5-O-(3'-N-desmethyl-3'-N-isopropyl)desosaminyl-3-O-[4-(s)-methyl-oxazolidin-2-one]carbamoyl-6-O-methyl-erythronolide A 11,12-(cyclic carbamate) (Example 6) (100 mg, 0.11 mmol) in MeOH (2 mL) was added NaOAc.3H$_2$O (75 mg, 0.55 mmol) and I$_2$ (34 mg, 0.13 mmol). The reaction vessel was equipped with a reflux condenser, and the dark reaction mixture was placed under a 500 W lamp for 15 min, after which time the dark color had dissipated and TLC (9:1 CHCl$_3$:MeOH) indicated the reaction was complete. Solvents were removed in vacuo, and the residue was partitioned between 0.5 M Na$_2$S$_2$O$_3$ (20 mL) and CHCl$_3$ (3×20 mL). The combined organic layers were dried over Na$_2$SO$_4$, then filtered and concentrated to give a crude product which was purified by silica gel column chromatography (97:3 CHCl$_3$:MeOH) to give a colorless, amorphous solid: R$_f$0.30 (9:1 CHCl$_3$:MeOH); IR (KBr) υ 3440, 2970, 1820, 1800, 1755, 1735, 1460, 1380, 1350, 1305, 1170, 1105, 1065, 1040 cm$^{-1}$; $^{13}$C NMR (75 MHz, CDCl$_3$) δ 215.6, 174.0, 157.0, 151.4, 151.1, 137.2, 131.9, 130.3, 128.5, 102.4, 82.7, 81.4, 79.9, 78.5, 76.9, 74.5, 69.4, 68.6, 60.6, 56.8, 51.5, 50.2, 45.7, 45.0, 42.9, 38.9, 38.7, 38.6, 36.2, 32.8, 29.7, 24.3, 22.3, 22.0, 21.0, 19.6, 19.5, 18.9, 15.0, 14.3, 10.1, 9.1; MS (ESI) m/z 894 (M+H)$^+$; Anal. Calcd for C$_{45}$H$_{68}$ClN$_3$O$_{13}$ (894.493): C, 60.42; H, 7.66; N, 4.69. Found: C, 60.59; H, 7.88; N, 4.43.

Example 8

11-Deoxy-11-[carboxy(4-chlorophenethyl)amino]-5-O-(3'-N-desmethyl-3'-N-isopropyl)desosaminyl-3-O-[4-(R)-methyl-oxazolidine]carbamoyl-6-O-methyl-erythronolide A 11,12-(cyclic carbamate)

To a solution of 11-deoxy-11-[carboxy(4-chlorophenethyl)amino]-3-O-[2-(R)-amino-1-propanol]carbamoyl-5-O-(2'-O-acetyl-3'-N-desmethyl-3'-N-isopropyl)desosaminyl-6-O-methyl-erythronolide A 11,12-(cyclic carbamate) (Compound 15) (200 mg, 0.22 mmol) in benzene (4 mL) under dry N$_2$ was added paraformaldehyde (30 mg, 0.99 mmol CH$_2$O) and (±)-camphorsulfonic acid (60 mg, 0.26 mmol). The reaction vessel was equipped with a Dean-Stark apparatus, and the reaction mixture was stirred at reflux 8 h, after which time TLC (19:1 CHCl$_3$:MeOH) indicated near complete conversion to a less polar product (9:1 CHCl$_3$:MeOH). The mixture was partitioned between saturated aq. NaHCO$_3$ (50 mL) and CHCl$_3$ (3×30 mL), and the combined organic layers were dried over Na$_2$SO$_4$. The drying agent was filtered off, and solvent was removed in vacuo to give a crude product which was purified by column chromatography on silica gel (1:2 EtOAc:hexanes) to give the 2'-O-acetate of example 8 as a colorless, amorphous solid [(85 mg, 42%), R$_f$=0.40 (19:1 CHCl$_3$:MeOH), MS (APCI) m/z 936 (M+H)$^+$]. A solution of this compound (80 mg, 85 μmol) in MeOH (3 mL) was stirred at rt 16 h, after which time TLC (9:1 CHCl$_3$:MeOH) indicated the reaction was complete. The solvent was removed in vacuo to give a crystalline compound which was recrystallized from aq. MeOH to give colorless prisms (44 mg, 58%): 153–155° C.; R$_f$=0.45 (9:1 CHCl$_3$:MeOH); IR (KBr) υ 3440, 2970, 1765, 1730, 1710, 1460, 1410, 1375, 1170, 1105, 1070 cm$^{-1}$; $^{13}$C NMR (75 MHz, CDCl$_3$) δ 215.7, 174.2, 157.1, 153.5, 137.2, 132.0, 130.3, 128.5, 103.9, 103.6, 82.8, 81.9, 79.1, 79.0, 78.4, 76.6, 74.3, 73.5, 69.9, 69.6, 64.0, 63.2, 60.7, 52.5, 51.8, 51.3, 50.1, 45.7, 45.1, 43.2, 38.9, 38.6, 35.9, 32.8, 31.1, 30.6, 22.1, 21.2, 20.9, 20.6, 19.5, 18.9, 18.6, 15.2, 14.3 (2C), 10.1, 9.1;

MS (FAB) m/z 894 (M+H)$^+$; Anal. Calcd for C$_{46}$H$_{72}$ClN$_3$O$_{12}$.0.5H$_2$O (903.545): C, 61.15; H, 8.14; N, 4.65. Found: C, 60.99; H, 8.18; N, 4.51.

Example 9

11-Deoxy-11-[carboxy(4-chlorophenethyl)amino]-5-O-(3'-N-desmethyl-3'-N-isopropyl)desosaminyl-3-O-(tetrahydro-3-furoyl)-6-O-methyl-erythronolide A 11 12-(cyclic carbamate)

To a solution of tetrahydro-2-furoic acid (0.12 mL, 1.25 mmol) in anhydrous CH$_2$Cl$_2$ (5 mL) at 0° C. under dry N$_2$ was added trimethylacetyl chloride (0.16 mL, 1.30 mmol) and triethylamine (0.18 mL, 1.30 mmol), and the resulting solution was stirred at 0° C. 1 h. This mixture was transferred via canula to a flask containing a solution of 11-deoxy-11-[carboxy(4-chlorophenethyl)amino]-5-O-(2'-O-acetyl-3'-N-desmethyl-3'-N-isopropyl)desosaminyl-6-O-methyl-erythronolide A 11,12-(cyclic carbamate) (Compound 14) (250 mg, 0.30 mmol) in anhydrous CH$_2$Cl$_2$ (2 mL) at 0° C. under dry N$_2$. The reaction mixture was allowed to warm to rt and stir 16 h, after which time TLC (19:1 CHCl$_3$:MeOH) indicated the reaction was complete. The mixture was diluted with CH$_2$Cl$_2$ (50 mL), washed with saturated aq. NH$_4$Cl (20 mL), saturated aq. NaHCO$_3$ (20 mL), and brine (20 mL), and dried over Na$_2$SO$_4$. The drying agent was filtered off, and solvent was removed in vacuo to give a crude product which was purified by column chromatography on silica gel (98:2 CHCl$_3$:MeOH) to give the 2'-O-acetate of example 9 as a colorless, amorphous solid [(245 mg, 89%), R$_f$=0.60 (19:1 CHCl$_3$:MeOH), MS (FAB) m/z 921 (M+H)$^+$]. A solution of this compound (233 mg, 0.25 mmol) in MeOH (10 mL) was stirred at rt 16 h, after which time TLC (9:1 CHCl$_3$:MeOH) indicated the reaction was complete. The solvent was removed in vacuo, and the crude product was purified by column chromatography on silica gel (97:3 CHCl$_3$:MeOH) to give a colorless, amorphous solid (110 mg, 50%): R$_f$=0.35 (19:1 CHCl$_3$:MeOH); IR (KBr) υ 3445, 2980, 1760, 1740, 1715, 1460, 1380, 1235, 1170, 1105, 1070 cm$^{-1}$; $^{13}$C NMR (75 MHz, CDCl$_3$) δ 215.8, 174.2, 173.6, 173.4, 157.1, 137.3, 131.9, 130.3, 128.5, 103.7, 82.7, 81.1, 78.6, 78.2, 76.8, 70.4, 70.1, 70.0, 68.2, 68.0, 63.1, 62.6, 60.7, 52.8, 50.2, 45.6, 45.0, 44.3, 44.2, 43.2, 43.1, 38.9, 38.6, 36.5, 33.0, 32.9, 32.8, 31.0, 22.1, 21.2, 19.7, 18.9, 15.3, 14.3 (2C), 10.1, 8.9; MS (APCI) m/z 879 (M+H)$^+$; Anal. Calcd for C$_{46}$H$_{71}$ClN$_2$O$_{12}$ (879.520): C, 62.82; H, 8.14; N, 3.19. Found: C, 62.53; H, 8.11; N, 3.11.

Example 10

11-Deoxy-11-[carboxy(4-chlorophenethyl)amino]-5-O-(3'-bis-N-desmethyl-3'-N-isopropyl)desosaminyl-3-O-(tetrahydro-3-furoyl)-6-O-methyl-erythronolide A 11,12-(cyclic carbamate)

To a solution of 11-deoxy-11-[carboxy(4-chlorophenethyl)amino]-5-O-(3'-N-desmethyl-3'-N-isopropyl)desosaminyl-3-O-(tetrahydro-2-furoyl)-6-O-methyl-erythronolide A 11,12-(cyclic carbamate) (Example 9) (243 mg, 0.28 mmol) in MeOH (2.5 mL) was added NaOAc.3H$_2$O (194 mg, 1.42 mmol) and I$_2$ (78 mg, 0.31 mmol). The reaction vessel was equipped with a reflux condenser, and the resulting dark reaction mixture was placed under a 500 W lamp for 2 h, after which time the dark color had dissipated and TLC (19:1 CHCl$_3$:MeOH) indicated the reaction was complete. Solvents were removed in vacuo, and the residue was dissolved in CHCl$_3$ (50 mL) and washed with 0.5 M Na$_2$S$_2$O$_3$ (30 mL), H$_2$O (30 mL) and brine (30 mL), and dried over Na$_2$SO4. The drying agent was filtered off, and solvent was removed in vacuo to give a crude product which was purified by silica gel column chromatography (97:3 CHCl$_3$:MeOH) to give a colorless, amorphous solid (170 mg, 71%): R$_f$=0.15 (19:1 CHCl$_3$:MeOH); IR (KBr) υ 3450, 2975, 1760, 1740, 1715, 1460, 1380, 1235, 1170, 1070 cm$^{-1}$; $^{13}$C NMR (75 MHz, CDCl$_3$) δ 215.7, 174.1, 173.6, 157.1, 137.3, 132.0, 130.3, 128.5, 103.0, 82.7, 80.9, 78.5, 78.0, 76.8, 74.8, 70.4, 70.1, 70.0, 69.3, 68.1, 60.7, 56.5, 50.2, 45.6, 45.4, 45.0, 44.3, 43.2, 43.1, 38.9, 38.8, 38.6, 36.4, 32.8, 29.5, 28.9, 24.6, 22.5, 22.1, 21.0, 19.6, 18.9, 15.3, 14.3 (2C), 10.1, 9.1; MS (APCI) m/z 865 (M+H)$^+$; Anal. Calcd for C$_{45}$H$_{69}$ClN$_2$O$_{12}$ (865.493): C, 62.45; H, 8.04; N, 3.24. Found: C, 62.28; H, 7.87; N, 2.99.

Example 11

11-Deoxy-11-[carboxy(3,4-dichlorophenethyl)amino]-3-O-[4-(s)-methyl-oxazolidin-2-one]carbamoyl-5-O-desosaminyl-6-O-methyl-erythronolide A 11,12-(cyclic carbamate) (Compound 21, Scheme 3)

Step 1: 2'-O-Acetyl-4"-O-trimethylsilyl-6-O-methyl-erythromycin A (Compound 18, Scheme 3)

To a solution of 2'-O-acetyl-6-O-methyl-erythromycin A (Compound 17) (45 g, 57 mmol) in anhydrous CH$_2$Cl$_2$ (450 mL) at 0° C. under a drying tube was added pyridine (13.8 mL, 171 mmol), followed by the dropwise addition of chlorotrimethylsilane (14.5 mL, 114 mmol) over 15 min. The reaction mixture was stirred at 0° C. for 1 h, after which time TLC (9:1 CH$_2$Cl$_2$:MeOH) indicated the reaction was complete. The mixture was washed with 0.5 M NaH$_2$PO$_4$ (500 mL), H$_2$O (300 mL), saturated aq. NaHCO$_3$ (300 mL), H$_2$O (300 mL), and brine (100 mL) and dried over Na$_2$SO$_4$. The drying agent was filtered off, and solvent was removed in vacuo to give a crude product which crystallized from CH$_3$CN to give compound 18 (48 g, 98%): mp=235–237° C.; R$_f$=0.50 (9:1 CH$_2$Cl$_2$:MeOH); $^{13}$C NMR (75 MHz, CDCl$_3$) δ 221.0, 175.6, 169.9, 100.0, 96.0, 80.5, 80.3, 78.3, 77.8, 76.4, 74.1, 73.2, 72.0, 69.0, 67.1, 65.2, 62.7, 50.3, 49.4, 45.1, 44.9, 40.5, 38.7, 38.6, 37.1, 35.6, 30.9, 22.1, 21.5, 21.4, 20.9, 19.7, 19.2, 17.8, 15.9, 15.8, 12.1, 10.4, 8.9, 0.8; MS (ESI) m/z 862 (M+H)$^+$.

Step 2: 2'-O-Acetyl-4"-O-trimethylsilyl-11-deoxy-11-[carboxy(3,4-dichloro-phenethyl)amino]-6-O-methyl-erythromycin A 11,12-(cyclic carbamate) (Compound 19, Scheme 3)

To a solution of 2'-O-acetyl-4"-O-trimethylsilyl-6-O-methyl-erythromycin A (Compound 18) (20.40 g, 24.2 mmol) in anhydrous THF (20 mL) and anhydrous DMF (200 mL) at 0° C. under dry N$_2$ was added 1,1'-carbonyldiimidazole (19.6 g, 120.9 mmol), followed by the portionwise addition of NaH (60% suspension in mineral oil, 1.16 g, 29.0 mmol). The reaction mixture was allowed to warm to rt and stir 1 h, after which time TLC (17:3 EtOAc:i-PrOH) indicated the reaction was complete. The reaction was carefully quenched with H$_2$O, partitioned between H$_2$O (500 mL) and EtOAc (3×300 mL), and the combined organic layers dried over Na$_2$SO$_4$. The drying agent was filtered off, and solvent was removed in vacuo to give the crude acylimidazolide [R$_f$=0.40 (17:3 EtOAc:i-PrOH), MS (FAB) m/z 938 (M+H)$^+$]. To a solution of this compound (10.00 g, 10.7 mmol) in CH$_3$CN (30 mL) was added 3,4-dichlorophenethylamine (8.00 g, 42.1 mmol), and the reaction mixture was stirred at rt for 72 h, during which time the product slowly precipitated. TLC (17:3 EtOAc:i-PrOH) indicated only a trace of unreacted compound remained. The solvent was removed in vacuo, the residue was partitioned between H$_2$O (200 mL) and EtOAc (3×200 mL), and the combined organic layers were dried over Na$_2$SO$_4$. The drying agent was filtered off, and solvent was removed in vacuo to give a crude product which crystallized from hot CH$_3$CN to give compound 19 (6.5 g). The filtrate was concentrated and purified by column chromatography on silica gel (23:2 EtOAc:i-PrOH) to give additional compound 19 as a colorless, amorphous solid (3.7 g, total yield=10.2 g, 90%): mp=169–173° C.; R$_f$=0.60 (17:3 EtOAc:i-PrOH; $^{13}$C NMR (75 MHz, CDCl$_3$) δ 216.4, 176.3, 170.0, 157.2, 139.3, 132.2, 131.0, 130.2, 130.1, 128.4, 100.1, 96.3, 82.8, 80.6, 79.8, 78.9, 76.2, 73.2, 71.8, 67.3, 65.3, 62.8, 60.3, 50.5, 49.6, 45.5, 45.3, 44.8, 40.6, 39.0, 38.7, 38.5, 35.7, 32.6, 31.1, 22.2, 21.9, 21.6, 20.2, 19.3, 18.8, 16.1, 14.3, 14.1, 10.2, 9.1, 0.9; MS (ESI) m/z 1059 (M+H)$^+$.

Step 3: 11-Deoxy-11-[carboxy(3,4-dichlorophenethyl)amino]-3-O-[carboxy(1-imidazole)]-5-O-(2'-O-acetyl)desosaminyl-6-O-methyl-erythronolide A 11,12-(cyclic carbamate) (Compound 20, Scheme 3).

A solution of 2'-O-acetyl-4"-O-trimethylsilyl-11-deoxy-11-[carboxy(3,4-dichlorophenethyl)amino]-6-O-methyl-erythromycin A 11,12-(cyclic carbamate) (Compound 19) (9.40 g, 8.87 mmol) in 1:1 N HCl:EtOH (600 mL) was stirred at rt 16 h, after which time TLC (19:1 CHCl$_3$:MeOH) indicated the reaction was complete. 2 N NaOH was carefully added to adjust to pH 5, and the resulting solution was extracted with CHCl$_3$ (3×300 mL). The combined organic layers were dried over Na$_2$SO$_4$, then filtered and concentrated to give a crude product which was purified by column chromatography on silica gel (19:1 CHCl$_3$:MeOH) to give a colorless, amorphous solid [(6.97 g, 95%), R$_f$=0.25 (19:1 CHCl$_3$:MeOH), MS (APCI) m/z 829 (M+H)$^+$]. To a solution of this compound in anhydrous CH$_2$Cl$_2$ (50 mL) under dry N$_2$ was added 1,1'-carbonyldiimidazole (2.00 g, 12.33 mmol) and 4-dimethylaminopyridine (0.75 g, 6.14 mmol). The reaction mixture was stirred at rt 3 days, after which time TLC (9:1 CHCl$_3$:MeOH) indicated the reaction was complete. The mixture was partitioned between 0.5 M NaH$_2$PO$_4$ (200 mL) and CHCl$_3$ (3×200 mL), and the combined organic layers were dried over Na$_2$SO$_4$. The drying agent was filtered off, and solvent was removed in vacuo to give a crude product which was purified by column chromatography on silica gel (9:1 CHCl$_3$:i-PrOH) to give compound 20 as a colorless, amorphous solid (7.00 g, 85% from 19): R$_f$=0.50 (9:1 CHCl$_3$:MeOH); 13C NMR (75 MHz, CDCl$_3$) δ 215.5, 173.5, 169.6, 157.0, 148.6, 139.1, 136.9, 132.3, 131.4, 131.0, 130.3, 128.3, 116.9, 100.3, 82.7, 82.6, 78.5, 78.0, 77.2, 71.2, 69.3, 63.1, 60.8, 50.3, 45.7, 44.9, 42.7, 40.5, 39.0, 38.2, 36.1, 32.6, 30.4, 22.0, 21.3, 20.9, 19.3, 18.9, 14.9, 14.3, 10.1, 8.7; MS (APCI) m/z 923 (M+H)$^+$.

Step 4: 11-Deoxy-11-[carboxy(3,4-dichlorophenethyl) amino]-3-O-[4-(s)-methyl-oxazolidin-2-one]carbamoyl-5-O-desosaminyl-6-O-methyl-erythronolide A 11,12-(cyclic carbamate) (Compound 21, Scheme 3)

To a solution of 11-deoxy-11-[carboxy(3,4-dichlorophenethyl)amino]-3-O-[carboxy(1-imidazole)]-5-O-(2'-O-acetyl)desosaminyl-6-O-methyl-erythronolide A 11,12-(cyclic carbamate) (Compound 20) (1.00 g, 1.08 mmol) and 4-(s)-methyl-oxazolidin-2-one (0.33 g, 3.25 mmol) in anhydrous THF (20 mL) at −78° C. under dry N$_2$ was added a solution of lithium bis(trimethylsilyl)amide (1.0 M in hexanes, 1.10 mL) dropwise. The mixture was stirred at −78° C. 30 min, then anhydrous DMF (10 mL) was slowly added over ca. 5 min. The reaction mixture was allowed to warm to −40° C. and stir 8 h, after which time TLC (1:1 CHCl$_3$:acetone) indicated the reaction was complete. The reaction was quenched cold with saturated aq. NH$_4$Cl (2 mL) and partitioned between H$_2$O (100 mL) and EtOAc (3×100 mL). The combined organic layers were dried over Na$_2$SO$_4$, then filtered and concentrated to give a crude product which was purified by column chromatography on silica gel (7:3 CHCl$_3$:acetone) to give the 2'-O-acetate of compound 21 as a colorless, amorphous solid [(0.77 g, 74%), R$_f$=0.30 (1:1 CHCl$_3$:acetone), MS (ESI) m/z 956 (M+H)$^+$]. This compound was dissolved in MeOH (20 mL) and AcOH (75 μL) and stirred at rt 24 h, after which time TLC (4:1 CH$_2$Cl$_2$:i-PrOH) indicated the reaction was complete. The solvent was removed in vacuo to give a crude product which was purified by column chromatography on silica gel (9:1 CH$_2$Cl$_2$:i-PrOH) to give compound 21 as a colorless, amorphous solid (0.69 g, 70% from 20): R$_f$=0.30 (9:1 CHCl$_3$:MeOH); IR (KBr) υ 3440, 2965, 2945, 1820, 1800, 1755, 1735, 1455, 1380, 1350, 1305, 1165, 1105, 1065, 1050 cm$^{-1}$; $^{13}$C NMR (75 MHz, CDCl$_3$) δ 215.8, 174.1, 157.1, 151.4, 151.1, 139.2, 132.2, 131.0, 130.3, 130.2, 128.4, 103.0, 82.8, 81.3, 79.5, 78.6, 76.8, 70.5, 69.7, 68.6, 65.8, 60.7, 51.5, 50.3, 45.7, 44.9, 42.9, 40.3, 38.9, 38.6, 36.4, 32.6, 28.7, 22.0, 21.2, 19.6, 19.5, 18.9, 15.0, 14.3, 14.2, 10.1, 8.8; MS (APCI) m/z 914 (M+H)$^+$; Anal. Calcd for C$_{44}$H$_{65}$Cl$_2$N$_3$O$_{13}$ (914.908): C, 57.76; H, 7.16; N, 4.59. Found: C, 57.67; H, 7.16; N, 4.45.

Example 12

Step 5: 11-Deoxy-11-[carboxy(3,4-dichlorophenethyl) amino]-3-O-[4-(s)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate) (Compound 22, Scheme 3)

To a solution of 11-deoxy-11-[carboxy(3,4-dichlorophenethyl)amino]-3-O-[4-(s)-methyl-oxazolidin-2-one]carbamoyl-5-O-desosaminyl-6-O-methyl-erythronolide A 11,12-(cyclic carbamate) (Compound 21) (1.00 g, 1.10 mmol) in i-PrOH (50 mL) was added I$_2$ (0.31 g, 1.20 mmol) and NaOAc.3H$_2$O (0.75 g, 5.51 mmol). The reaction vessel was equipped with a reflux condenser, and the dark colored mixture was stirred under a 500 W lamp 1 h, after which time the dark color was dissipated and TLC (9:1 CHCl$_3$:MeOH) indicated the reaction was complete. The cooled mixture was partitioned between 0.5 M Na$_2$S$_2$O$_3$ (100 mL) and CHCl$_3$ (3×100 mL), and the combined organic layers were washed with H$_2$O (100 mL) and brine (100 mL) and dried over Na$_2$SO$_4$. The drying agent was filtered off, and solvent was removed in vacuo to give a crude product which was precipitated from Et$_2$O to give the 3'-N-desmethyl derivative of compound 21 as an off white powder [(0.95 g, 96%), R$_f$=0.15 (9:1 CHCl$_3$:MeOH), MS (APCI) m/z 900 (M+H)$^+$]. To a solution of this compound (202 mg, 224 μmol) in i-PrOH (7 mL) was added cyclopropanecarboxaldehyde (0.17 mL, 2.24 mmol), AcOH (25 μL) and NaCNBH$_3$ (28 mg, 448 μmol). The reaction mixture was stirred at rt 16 h, after which time TLC (9:1 EtOAc:MeOH) indicated the reaction was complete. The mixture was diluted with EtOAc (100 mL), washed with saturated NH$_4$Cl (50 mL), saturated aq. NaHCO$_3$ (2×50 mL), H$_2$O (2×50 mL) and brine, and the organic phase was dried over Na$_2$SO$_4$. The drying agent was filtered off, and solvent was removed in vacuo to give a crude product which was purified by column chromatography on silica gel (EtOAc) to give compound 22 as a colorless, amorphous solid (140 mg, 66%): R$_f$=0.35 (9:1 EtOAc:i-PrOH); IR (microscope) υ 3445, 2980, 2945, 1825, 1800, 1760, 1740, 1460, 1380, 1350, 1310, 1235, 1170, 1110, 1070, 1055 cm$^{-1}$; $^{13}$C NMR (75 MHz, CDCl$_3$) δ 215.8, 174.1, 157.1, 151.4, 151.2, 139.2, 132.2, 131.0, 130.3, 130.2, 128.4, 102.9, 82.8, 81.2, 79.1, 78.5, 76.8, 70.1, 69.7, 68.6, 64.4, 60.6, 58.5, 51.5, 50.3, 45.7, 44.9, 42.9, 38.9, 38.5, 36.9, 36.4, 32.6, 29.3, 22.0, 21.2, 19.7, 19.6, 18.9, 15.1, 14.3, 14.2, 10.1, 8.9, 4.4, 3.6; MS (APCI) m/z 954 (M+H)$^+$; Anal. Calcd for C$_{47}$H$_{69}$Cl$_2$N$_3$O$_{13}$ (954.98): C, 59.11; H, 7.28; N, 4.40. Found: C, 59.39; H, 7.17; N, 4.13.

Example 13

11-Deoxy-11-[carboxy(3,4-dichlorophenethyl)amino]-3-O-[4-(s)-methyl-oxazolidin-2-one]carbamoyl-5-O-(3'-N-desmethyl-3'-N-cyclobutyl)desosaminyl-6-O-methyl-erythronolide A 11,12-(cyclic carbamate)

The title compound was prepared following the procedure described in Scheme 3, substituting cyclobutanone for cyclopropanecarboxaldehyde. The crude product was purified by silica gel column chromatography (19:1 EtOAc:i-PrOH) to give a colorless, amorphous solid: R$_f$=0.50 (17:3 EtOAc:i-PrOH); IR (KBr) υ 3440, 2975, 2940, 1820, 1800, 1760, 1740, 1460, 1380, 1350, 1305, 1170, 1105, 1065 cm$^{-1}$; $^{13}$C NMR (75 MHz, CDCl$_3$) δ 215.8, 174.0, 157.1, 151.3, 151.1, 139.2, 132.2, 131.0, 130.3, 130.2, 128.4, 103.1, 82.8, 81.4, 81.3, 79.7, 78.5, 76.8, 69.8, 69.7, 68.6, 60.7, 60.4, 56.9, 51.5, 50.2, 45.7, 45.6, 44.9, 43.0, 38.9, 38.5, 36.4, 32.6, 31.2, 29.7 (2C), 28.5 (2C), 28.1, 22.0, 21.2, 19.8, 19.5, 18.9, 15.1, 14.3, 14.2, 14.1, 10.1, 8.9; MS (ESI) m/z 954 (M+H)$^+$; Anal. Calcd for C$_{47}$H$_{69}$Cl$_2$N$_3$O$_{13}$ (954.98): C, 59.11; H, 7.28; N, 4.40. Found: C, 58.81; H, 7.44; N, 4.25.

Example 14

11-Deoxy-11-[carboxy(3,4-dichlorophenethyl)amino]-3-O-[4-(s)-methyl-oxazolidin-2-one]carbamoyl-5-O-(3'-N-desmethyl-3'-N-cyclopentyl)desosaminyl-6-O-methyl-erythronolide A 11,12-(cyclic carbamate)

The title compound was prepared following the procedure described in Scheme 3, substituting cyclopentanone for cyclopropanecarboxaldehyde. The crude product was purified by silica gel column chromatography (19:1 EtOAc:i-PrOH) to give a colorless, amorphous solid: R$_f$=0.35 (9:1 EtOAc:i-PrOH); IR (KBr) υ 3440, 2970, 1820, 1800, 1755, 1735, 1460, 1380, 1350, 1305, 1230, 1170, 1105, 1060 cm$^{-1}$; $^{13}$C NMR (75 MHz, CDCl$_3$) δ 215.8, 174.0, 157.1, 151.4, 151.2, 139.2, 132.2, 131.0, 130.3, 130.2, 128.4, 103.0, 82.8, 81.3, 79.7, 78.5, 76.8, 69.8, 69.7, 68.6, 64.1, 63.3, 60.7, 51.5, 50.2, 45.7, 44.9, 43.0, 38.9, 38.5, 36.4, 33.4, 32.6, 31.4, 30.9, 30.3, 29.7, 23.7, 23.2, 22.0, 21.2, 19.7, 19.5, 18.9, 15.1, 14.3, 14.2, 10.1, 8.9; MS (APCI) m/z 968 (M+H)$^+$; Anal. Calcd for $C_{48}H_{71}Cl_2N_3O_{13}$ (969.01): C, 59.49; H, 7.38; N, 4.33. Found: C, 59.88; H, 7.44; N, 4.31.

Example 15

11-Deoxy-11-[carboxy(3,4-dichlorophenethyl)amino]-3-O-[4-(s)-methyl-oxazolidin-2-one]carbamoyl-5-O-(3'-N-desmethyl-3'-N-cyclohexyl)desosaminyl-6-O-methyl-erythronolide A 11,12-(cyclic carbamate)

The title compound was prepared following the procedure described in Scheme 3, substituting cyclohexanone for cyclopropanecarboxaldehyde. The crude product was purified by silica gel column chromatography (19:1 EtOAc:i-PrOH) to give a colorless, amorphous solid: $R_f$=0.45 (9:1 EtOAc:i-PrOH); IR (KBr) υ 3440, 2930, 1820, 1800, 1755, 1735, 1455, 1380, 1350, 1305, 1170, 1100, 1065 cm$^{-1}$; $^{13}$C NMR (75 MHz, CDCl$_3$) δ 215.9, 174.0, 157.1, 151.4, 139.2, 132.2, 131.1, 130.3, 130.2, 128.4, 103.1, 82.9, 81.4, 78.6, 76.8, 69.9, 69.8, 69.5, 68.7, 63.0 (2C), 60.7, 51.5, 50.2, 45.7, 44.9, 43.0, 42.0, 38.9, 38.5, 37.9, 36.5, 33.6, 32.6, 29.7, 27.0, 25.8, 24.5, 22.5, 22.0, 21.2, 19.7, 19.6, 18.9, 15.1, 14.3, 14.2, 10.1, 8.9; MS (ESI) m/z 982 (M+H)$^+$; Anal. Calcd for $C_{49}H_{73}Cl_2N_3O_{13}$ (983.04): C, 59.86; H, 7.48; N, 4.27. Found: C, 60.21; H, 7.51; N, 4.13.

Example 16

11-Deoxy-11-[carboxy(3,4-dichlorophenethyl)amino]-3-O-[4-(s)-methyl-oxazolidin-2-one]carbamoyl-5-O-(3'-N-desmethyl-3'-N-n-propyl)desosaminyl-6-O-methyl-erythronolide A 11,12-(cyclic carbamate)

The title compound was prepared following the procedure described in Scheme 3, substituting propionaldehyde for cyclopropanecarboxaldehyde. The crude product was purified by silica gel column chromatography (19:1 EtOAc:i-PrOH) to give a colorless, amorphous solid: $R_f$=0.30 (9:1 EtOAc:i-PrOH); IR (KBr) υ 3445, 2970, 2935, 1820, 1800, 1755, 1735, 1460, 1380, 1350, 1305, 1170, 1105, 1065 cm$^{-1}$; $^{13}$C NMR (75 MHz, CDCl$_3$) δ 215.9, 174.1, 157.1, 151.4, 151.2, 139.2, 132.2, 131.0, 130.3, 130.2, 128.4, 103.0, 82.8, 81.2, 79.5, 78.5, 76.8, 70.2, 69.8, 68.6, 65.7, 60.6, 55.2, 51.5, 50.3, 45.7, 44.9, 42.9, 38.9, 38.5, 36.8, 36.4, 32.6, 29.7, 29.5, 22.0, 21.3, 21.2, 19.7, 19.6, 18.9, 15.1, 14.3, 14.2, 11.5, 10.1, 8.9; MS (APCI) m/z 942 (M+H)$^+$; Anal. Calcd for $C_{46}H_{69}Cl_2N_3O_{13}$ (942.97): C, 58.59; H, 7.37; N, 4.45. Found: C, 59.17; H, 7.52; N, 4.25.

Example 17

11-Deoxy-11-[carboxy(3,4-dichlorophenethyl)amino]-3-O-[4-(s)-methyl-oxazolidin-2-one]carbamoyl-5-O-(3'-N-desmethyl-3'-N-isobutyl)desosaminyl-6-O-methyl-erythronolide A 11,12-(cyclic carbamate)

The title compound was prepared following the procedure described in Scheme 3, substituting isobutyraldehyde for cyclopropanecarboxaldehyde. The crude product was purified by silica gel column chromatography (49:1 EtOAc:acetone) to give a colorless, amorphous solid: $R_f$=0.75 (9:1 CHCl$_3$:MeOH); IR (KBr) υ 3445, 2965, 2950, 1820, 1800, 1755, 1735, 1460, 1380, 1350, 1305, 1170, 1110, 1065, 1050 cm$^{-1}$; $^{13}$C NMR (75 MHz, CDCl$_3$) δ 215.9, 174.1, 157.1, 151.4, 151.1, 139.2, 132.2, 131.0, 130.3, 128.4, 103.0, 82.8, 81.2, 79.4, 78.5, 76.8, 70.3, 69.8, 68.6, 66.5, 61.4, 60.6, 51.5, 50.3, 45.7, 44.9, 42.9, 38.9, 38.5, 37.3, 36.4, 32.6, 29.4, 26.1, 22.0, 21.2, 20.6, 20.4, 19.7, 19.6, 18.9, 15.1, 14.3, 14.2, 10.1, 8.9; MS (APCI) m/z 956 (M+H)$^+$; Anal. Calcd for $C_{47}H_{71}Cl_2N_3O_{13}$ (956.989): C, 58.98; H, 7.47; N, 4.39. Found: C, 59.05; H, 7.43; N, 4.06.

Example 18

11-Deoxy-11-[carboxy(3,4-dichlorophenethyl)amino]-3-O-[4-(s)-methyl-oxazolidin-2-one]carbamoyl-5-O-(3'-N-desmethyl-3'-N-cyclobutylmethyl)desosaminyl-6-O-methyl-erythronolide A 11,12-(cyclic carbamate)

The title compound was prepared following the procedure described in Scheme 3, substituting cyclobutanecarboxaldehyde for cyclopropanecarboxaldehyde. The crude product was purified by silica gel column chromatography (7:3 EtOAc:hexane) to give a colorless, amorphous solid: $R_f$=0.35 (EtOAc); IR (microscope) υ 3450, 2975, 2940, 1825, 1800, 1760, 1740, 1460, 1380, 1350, 1305, 1170, 1110, 1065 cm$^{-1}$; MS (APCI) m/z 968 (M+H)$^+$.

Example 19

11-Deoxy-11-[carboxy(3,4-dichlorophenethyl)amino]-3-O-[4-(s)-methyl-oxazolidin-2-one]carbamoyl-5-O-(3'-N-desmethyl-3'-N-isopropyl)desosaminyl-6-O-methyl-erythronolide A 11,12-(cyclic carbamate)

The title compound was prepared following the procedure described in Scheme 3, substituting acetone for cyclopropanecarboxaldehyde. The crude product was purified by silica gel column chromatography (19:1 EtOAc:i-PrOH) to give a colorless, amorphous solid: $R_f$=0.55 (9:1 CHCl$_3$:MeOH); IR (microscope) υ 3440, 2970, 2940, 1820, 1800, 1755, 1735, 1460, 1380, 1350, 1305, 1170, 1105, 1065, 1045 cm$^{-1}$; $^{13}$C NMR (75 MHz, CDCl$_3$) δ 215.8, 174.1, 157.1, 151.4, 151.1, 139.2, 132.2, 131.0, 130.3, 130.2, 128.4, 125.0, 103.0, 82.8, 81.3, 79.7, 79.6, 78.6, 76.8, 70.0, 69.7, 68.6, 62.9, 60.7, 51.5, 50.3, 45.7, 44.9, 43.0, 38.9, 38.5, 36.4, 33.1, 32.6, 30.9 (2C), 29.7, 22.0, 21.2, 21.0, 20.9, 20.4, 19.7, 19.6, 18.9, 15.1, 14.3, 14.2, 10.1, 8.9; MS (ESI) m/z 942 (M+H)$^+$; Anal. Calcd for $C_{46}H_{69}Cl_2N_3O_{13}$ (942.97): C, 58.59; H, 7.37; N, 4.45. Found: C, 58.73; H, 7.17; N, 4.21.

Example 20

11-Deoxy-11-[carboxy(3,4-dichlorophenethyl)amino]-3-O-[4-(s)-methyl-oxazolidin-2-one]carbamoyl-5-O-(3'-bis-N-desmethyl-3'-N-ethyl-3'-N-isopropyl)desosaminyl-6-O-methyl-erythronolide A 11,12-(cyclic carbamate)

To a solution of 11-deoxy-11-[carboxy(3,4-dichlorophenethyl)amino]-3-O-[4-(s)-methyl-oxazolidin-2-one]carbamoyl-5-O-(3'-N-desmethyl-3'-N-isopropyl)desosaminyl-6-O-methyl-erythronolide A 11,12-(cyclic carbamate) (Example 19) (904 mg, 0.96 mmol) in i-PrOH (25 mL) was added NaOAc.3H$_2$O (653 mg, 4.80 mmol) and I$_2$ (269 mg, 1.06 mmol). The reaction vessel was equipped with a reflux condenser, and the dark colored mixture was stirred under a 500 W lamp 90 min, during which time the dark color dissipated. TLC (9:1 CHCl$_3$:MeOH) indicated partial conversion to a more polar product. The cooled mixture was partitioned between 0.5 M Na$_2$S$_2$O$_3$ (200 mL) and CHCl$_3$ (3×100 mL), and the combined organic layers were washed with H$_2$O (100 mL) and brine, then dried over MgSO$_4$. The drying agent was filtered off, and solvent was removed in vacuo to give a crude product which was purified by column chromatography on silica gel (9:1 EtOAc:i-PrOH) to give the 3'-N-desmethyl derivative of example 19 as an amorphous solid [(365 mg, 41%), $R_f$=0.20 (19:1 CHCl$_3$:MeOH), MS (APCI) m/z 928 (M+H)$^+$]. To a solution of this compound (75 mg, 81 μmol) in i-PrOH (2 mL) was added acetaldehyde (45 μL, 0.81 mmol), AcOH (10 μL) and NaCNBH$_3$ (11 mg, 162 μmol). The reaction mixture was stirred at rt 16 h, after which time TLC (19:1 CHCl$_3$:MeOH) indicated the reaction was complete. The mixture was diluted with EtOAc (100 mL), washed with saturated NH$_4$Cl (50 mL), saturated aq. NaHCO$_3$ (50 mL), H$_2$O (50 mL) and brine, and dried over MgSO$_4$. The drying agent was filtered off, and solvent was removed in vacuo to give a crude product which was purified by column chromatography on silica gel (EtOAc) to give a slightly impure product. To a solution of this compound in EtOAc (1 mL) was added 1 N HCl in Et$_2$O (0.1 mL). The resulting precipitate was collected and dried to provide the pure HCl salt (55 mg, 69%), which was dissolved in EtOAc, washed with saturated aq. NaHCO$_3$, dried over MgSO$_4$, filtered and concentrated to give a colorless amorphous solid: R$_f$=0.45 (19:1 CHCl$_3$:MeOH); IR (microscope) υ 3436, 2972, 2938, 1824, 1801, 1758, 1738, 1459, 1380, 1349, 1306, 1169, 1105, 1066, 1049 cm$^{-1}$; $^{13}$C NMR (125 MHz, CDCl$_3$) δ 215.8, 174.0, 157.1, 151.3, 151.1, 139.2, 132.2, 131.0, 130.3, 130.2, 128.3, 102.9, 82.8, 81.2, 79.3, 78.5, 76.7, 70.1, 69.9, 68.6, 60.6, 59.8, 51.4, 50.2, 48.1, 45.7, 44.8, 42.9, 38.9, 38.5, 38.4, 36.4, 34.5, 32.5, 29.6, 22.9, 21.9, 21.2, 19.8, 19.5, 18.9 (2C), 15.6, 15.1, 14.3, 14.1, 10.1, 8.9; MS (ESI) m/z 956 (M+H)$^+$; Anal. Calcd for C$_{47}$H$_{71}$Cl$_2$N$_3$O$_{13}$ (956.989): C, 58.98; H, 7.47; N, 4.39. Found: C, 59.13; H, 7.42; N, 4.23.

Example 21

11-Deoxy-11-[carboxy(3,4-dichlorophenethyl)amino]-3-O-[4-(s)-methyl-oxazolidin-2-one]carbamoyl-5-O-(3'-bis-N-desmethyl-3'-N-n-propyl-3'-N-isopropyl)desosaminyl-6-O-methyl-erythronolide A 11,12-(cyclic carbamate)

The title compound was prepared following the procedure described for Example 20, substituting propionaldehyde for acetaldehyde. The crude product was purified by silica gel column chromatography (1:1 EtOAc:hexanes) to give a colorless, amorphous solid: R$_f$=0.45 (4:1 EtOAc:hexanes); IR (microscope) υ 3442, 2968, 2936, 1824, 1801, 1758, 1738, 1459, 1380, 1349, 1306, 1272, 1169, 1105, 1066 cm$^{-1}$; MS (ESI) m/z 970 (M+H)$^+$.

Example 22

11-Deoxy-11-[carboxy(3,4-dichlorophenethyl)amino]-3-O-[4-(s)-methyl-oxazolidin-2-one]carbamoyl-5-O-(3'-bis-N-desmethyl-3'-N-cyclopropylmethyl-3'-N-isopropyl)desosaminyl-6-O-methyl-erythronolide A 11,12-(cyclic carbamate)

The title compound was prepared following the procedure described for Example 20, substituting cyclopropanecarboxaldehyde for acetaldehyde. The crude product was purified by silica gel column chromatography (1:1 EtOAc:hexanes) to give a colorless, amorphous solid: R$_f$=0.20 (1:1 EtOAc:hexanes); IR (KBr) υ 3437, 2971, 2938, 1824, 1801, 1758, 1738, 1459, 1380, 1349, 1306, 1169, 1105, 1066, 1045 cm$^{-1}$; $^{13}$C NMR (125 MHz, CDCl$_3$) δ 215.9, 174.1, 157.1, 151.3, 151.0, 139.2, 132.2, 131.0, 130.3, 130.1, 128.3, 102.8, 82.8, 81.1, 78.9, 78.5, 76.7, 70.1, 69.9, 68.5, 60.5, 59.6, 51.4, 50.2, 49.4, 47.8, 45.7, 44.8, 42.9, 38.8, 38.5, 36.3, 34.5, 32.5, 22.9, 21.9, 21.2, 19.7, 19.5, 18.9, 18.7, 15.0, 14.3, 14.1, 11.1, 10.1, 8.9, 5.5, 2.7; MS (APCI) m/z 982 (M+H)$^+$; Anal. Calcd for C$_{49}$H$_{73}$Cl$_2$N$_3$O$_{13}$ (983.04): C, 59.86; H, 7.48; N, 4.27. Found: C, 59.87; H, 7.34; N, 4.00.

Example 23

11-Deoxy-11-[carboxy(4-chlorophenethyl)amino]-3-O-[4-(s)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate)

The title compound was prepared following the procedure described in Scheme 3, substituting 4-chlorophenethylamine for 3,4-dichlorophenethylamine. The crude product was purified by silica gel column chromatography (19:1 EtOAc:i-PrOH) to give a colorless, amorphous solid: R$_f$=0.25 (9:1 EtOAc:i-PrOH); IR (KBr) υ 3430, 3175, 3125, 1820, 1795, 1755, 1735, 1460, 1380, 1350, 1305, 1165, 1100, 1060 cm$^{-1}$; $^{13}$C NMR (75 MHz, CDCl$_3$) δ 215.7, 174.0, 157.1, 151.4, 151.3, 137.3, 130.3, 128.5, 102.8, 82.7, 81.4, 78.5, 76.9, 70.0, 69.4, 68.7, 64.7, 60.6, 59.2, 51.5, 50.3, 45.7, 45.0, 43.0, 38.9, 38.5, 36.8, 36.3, 32.8, 30.1, 29.7, 22.0, 21.1, 19.7, 19.6, 18.9, 15.1, 14.3, 10.1, 9.0, 4.5, 3.9; MS (APCI) m/z 920 (M+H)$^+$; Anal. Calcd for C$_{47}$H$_{70}$ClN$_3$O$_{13}$ (920.531): C, 61.33; H, 7.67; N, 4.57. Found: C, 62.22; H, 7.74; N, 4.01.

Example 24

11-Deoxy-11-[carboxy(4-chlorophenethyl)amino]-3-O-[4-(s)-methyl-oxazolidin-2-one]carbamoyl-5-O-(3'-N-desmethyl-3'-N-cyclobutyl)desosaminyl-6-O-methyl-erythronolide A 11,12-(cyclic carbamate)

The title compound was prepared following the procedure described for Example 13, substituting 4-chlorophenethylamine for 3,4-dichlorophenethylamine. The crude product was purified by silica gel column chromatography (19:1 CH$_2$Cl$_2$:i-PrOH) to give a colorless, amorphous solid: R$_f$=0.65 (9:1 CHCl$_3$:MeOH); IR (microscope) υ 3445, 2975, 2940, 1820, 1800, 1760, 1735, 1460, 1380, 1350, 1305, 1170, 1105, 1060, 1045 cm$^{-1}$; $^{13}$C NMR (75 MHz, CDCl$_3$) δ 215.7, 174.0, 157.1, 151.3, 151.2, 137.3, 132.0, 130.3, 128.5, 103.1, 82.7, 81.4, 80.0, 78.5, 76.9, 69.7, 69.6, 68.6, 60.7, 60.6 (2C), 57.0, 51.5, 50.2, 45.7, 45.0, 43.0, 38.9, 38.5, 36.4, 32.8, 31.6, 31.3, 29.9, 28.4, 28.3, 28.0, 22.6, 22.1, 21.2, 19.8, 19.6, 18.9, 15.1, 14.3, 14.1, 10.1, 9.0; MS (ESI) m/z 920 (M+H)$^+$; Anal. Calcd for C$_{47}$H$_{70}$ClN$_3$O$_{13}$ (920.531): C, 61.33; H, 7.67; N, 4.57. Found: C, 61.43; H, 7.85; N, 4.36.

Example 25

11-Deoxy-11-[carboxy(4-chlorophenethyl)amino]-3-O-[4-(s)-methyl-oxazolidin-2-one]carbamoyl-5-O-(3'-N-desmethyl-3'-N-cyclopentyl)desosaminyl-6-O-methyl-erythronolide A 11,12-(cyclic carbamate)

The title compound was prepared following the procedure described for Example 14, substituting 4-chlorophenethylamine for 3,4-dichlorophenethylamine. The crude product was purified by silica gel column chromatography (9:1 EtOAc:i-PrOH) to give a colorless, amorphous solid: R$_f$=0.55 (19:1 CHCl$_3$:MeOH); IR (KBr) υ 3445, 2970, 1825, 1800, 1760, 1740, 1460, 1385, 1350, 1310, 1170, 1110, 1065 cm$^{-1}$; $^{13}$C NMR (75 MHz, CDCl$_3$) δ 215.7, 174.0, 157.1, 151.4, 151.1, 137.3, 132.0, 130.3, 128.5, 103.1, 82.7, 81.4, 79.6, 78.5, 76.9, 69.9, 69.8, 68.6, 63.7, 63.2, 60.6, 51.4, 50.2, 45.7, 45.0, 43.0, 38.9, 38.5, 36.4, 33.2, 32.8, 31.6, 31.0, 30.7, 30.2, 23.7, 22.1, 21.2, 19.8, 19.5, 18.9, 15.1, 14.3, 14.2, 10.1, 8.9; MS (APCI) m/z 934 (M+H)$^+$; Anal. Calcd for C$_{48}$H$_{72}$ClN$_3$O$_{13}$·H$_2$O (952.572): C, 60.52; H, 7.82; N, 4.41. Found: C, 60.50; H, 7.55; N, 4.21.

Example 26

11-Deoxy-11-[carboxy(4-chlorophenethyl)amino]-3-O-[4-(s)-methyl-oxazolidin-2-one]carbamoyl-5-O-(3'-N-desmethyl-3'-N-cyclohexyl)desosaminyl-6-O-methyl-erythronolide A 11,12-(cyclic carbamate)

The title compound was prepared following the procedure described for Example 15, substituting 4-chlorophenethylamine for 3,4-dichlorophenethylamine. The crude product was purified by silica gel column chromatography (19:1 EtOAc:i-PrOH) to give a colorless, amorphous solid: R$_f$=0.55 (9:1 EtOAc:i-PrOH); IR (microscope) υ 3440, 2970, 2935, 1820, 1800, 1760, 1735, 1455, 1380, 1350, 1305, 1270, 1170, 1105, 1060 cm$^{-1}$; $^{13}$C NMR (75 MHz, CDCl$_3$) δ 215.8, 174.0, 157.1, 151.4, 151.1, 137.3, 132.0, 130.3, 128.5, 103.1, 82.8, 81.5, 78.6, 76.9, 69.9 (2C), 68.6, 63.0, 60.7, 51.5, 50.2, 45.7, 45.0, 43.0, 38.9, 38.6, 36.4, 33.6, 32.8, 32.0, 29.7, 25.9, 22.1, 21.2, 19.8, 19.6, 18.9, 15.1, 14.3, 10.1, 9.0; MS (ESI) m/z 948 (M+H)$^+$; Anal. Calcd for $C_{49}H_{74}ClN_3O_{13}$ (948.585): C, 62.04; H, 7.86; N, 4.43. Found: C, 61.92; H, 7.93; N, 4.18.

Example 27
11-Deoxy-11-carboxy(4-chlorophenethyl)amino]-3-O-[4-(s)-methyl-oxazolidin-2-one]carbamoyl-5-O-(3'-N-desmethyl-3'-N-n-propyl)desosaminyl-6-O-methyl-erythronolide A 11,12-(cyclic carbamate)

The title compound was prepared following the procedure described for Example 16, substituting 4-chlorophenethylamine for 3,4-dichlorophenethylamine. The crude product was purified by silica gel column chromatography (19:1 EtOAc:i-PrOH) to give a colorless, amorphous solid: $R_f$=0.35 (9:1 EtOAc:i-PrOH); IR (KBr) υ 3440, 2965, 2935, 1820, 1800, 1755, 1740, 1460, 1380, 1350, 1310, 1170, 1110, 1065 cm$^{-1}$; $^{13}$C NMR (125 MHz, CDCl$_3$) δ 215.8, 174.0, 157.1, 151.4, 151.1, 137.3, 132.0, 130.3, 128.5, 103.0, 82.7, 81.3, 79.7, 78.5, 76.9, 70.2, 69.8, 68.6, 65.7, 60.6, 55.3, 51.5, 50.3, 45.7, 45.0, 43.0, 38.9, 38.6, 36.8, 36.4, 32.8, 29.6, 22.1, 21.2, 19.7, 19.6, 18.9, 15.1, 14.3 (2C), 11.5, 10.1, 8.9; MS (ESI) m/z 908 (M+H)$^+$; Anal. Calcd for $C_{46}H_{70}ClN_3O_{13}$·0.5H$_2$O (917.527): C, 60.22; H, 7.80; N, 4.58. Found: C, 60.37; H, 7.90; N, 4.37.

Example 28
11-Deoxy-11-[carboxy(4-fluorophenethyl)amino]-3-O-[4-(s)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate)

The title compound was prepared following the procedure described in Scheme 3, substituting 4-fluorophenethylamine for 3,4-dichlorophenethylamine. The crude product was purified by silica gel column chromatography (49:1 CH$_2$Cl$_2$:i-PrOH) to give a colorless, amorphous solid: $R_f$=0.30 (19:1 CH$_2$Cl$_2$:i-PrOH); IR (microscope) υ 3448, 2975, 2940, 1824, 1801, 1759, 1739, 1511, 1459, 1381, 1350, 1307, 1169, 1107, 1065 cm$^{-1}$; $^{13}$C NMR (75 MHz, CDCl$_3$) δ 215.8, 174.0, 161.5 (d, J=244 Hz), 157.1, 151.4, 151.1, 134.4 (d, J=2 Hz), 130.3 (d, J=7 Hz), 115.1 (d, J=21 Hz), 102.9, 82.7, 81.3, 79.4, 78.5, 76.8, 70.1, 69.8, 68.6, 64.8, 60.5, 58.8, 51.5, 50.3, 45.7, 45.2, 42.9, 38.9, 38.5, 36.9, 36.3, 32.6, 29.7, 29.6, 22.0, 21.2, 19.7, 19.6, 19.0, 15.1, 14.3 (2C), 10.1, 9.9, 8.9, 4.3, 3.5; MS (ESI) m/z 904 (M+H)$^+$; Anal. Calcd for $C_{47}H_{70}FN_3O_{13}$ (904.08): C, 62.44; H, 7.80; N, 4.64. Found: C, 62.34; H, 8.02; N, 4.49.

Example 29
11-Deoxy-11-[carboxy(4-fluorophenethyl)amino]-3-O-[4-(s)-methyl-oxazolidin-2-one]carbamoyl-5-O-(3'-N-desmethyl-3'-N-cyclobutyl)desosaminyl-6-O-methyl-erythronolide A 11,12-(cyclic carbamate)

The title compound was prepared following the procedure described for Example 13, substituting 4-fluorophenethylamine for 3,4-dichlorophenethylamine. The crude product was purified by silica gel column chromatography (49:1 CH$_2$Cl$_2$:i-PrOH) to give a colorless, amorphous solid: $R_f$=0.35 (19:1 CH$_2$Cl$_2$:i-PrOH); IR (microscope) υ 3457, 2974, 2940, 1824, 1802, 1758, 1739, 1511, 1459, 1380, 1351, 1307, 1233, 1169, 1106, 1064 cm$^{-1}$; $^{13}$C NMR (75 MHz, CDCl$_3$) δ 215.8, 174.0, 161.5 (d, J=243 Hz), 157.1, 151.3, 151.1, 134.4 (d, J=2 Hz), 130.3 (d, J=7 Hz), 115.1 (d, J=22 Hz), 103.1, 82.7, 81.3, 79.8, 78.5, 76.8, 69.8, 69.6, 68.6, 60.6, 60.3, 56.9, 51.5, 50.2, 45.7, 45.2, 43.0, 38.9, 38.5, 36.3, 32.6, 31.2, 29.7, 28.5, 28.1, 22.0, 21.2, 19.8, 19.6, 18.9, 15.1, 14.3, 14.1, 10.1, 9.0; MS (ESI) m/z 904 (M+H)$^+$; Anal. Calcd for $C_{47}H_{70}FN_3O_{13}$ (904.08): C, 62.44; H, 7.80; N, 4.64. Found: C, 62.29; H, 7.85; N, 4.55.

Example 30
11-Deoxy-11-[carboxy(4-fluorophenethyl)amino]-3-O-[4-(s)-methyl-oxazolidin-2-one]carbamoyl-5-O-(3'-N-desmethyl-3'-N-cyclopentyl)desosaminyl-6-O-methyl-erythronolide A 11,12-(cyclic carbamate)

The title compound was prepared following the procedure described for Example 14, substituting 4-fluorophenethylamine for 3,4-dichlorophenethylamine. The crude product was purified by silica gel column chromatography (49:1 CH$_2$Cl$_2$:i-PrOH) to give a colorless, amorphous solid: $R_f$=0.30 (19:1 CH$_2$Cl$_2$:i-PrOH); IR (microscope) υ 3447, 2971, 2943, 1824, 1801, 1756, 1738, 1511, 1458, 1380, 1350, 1307, 1233, 1169, 1106, 1064 cm$^{-1}$; $^{13}$C NMR (75 MHz, CDCl$_3$) δ 215.8, 174.0, 161.5 (d, J=244 Hz), 157.1, 151.3, 151.1, 134.4, 130.3 (d, J=8 Hz), 115.1 (d, J=21 Hz), 103.1, 82.7, 81.4, 79.7, 78.5, 76.9, 69.9, 69.8, 68.6, 63.8, 63.2, 60.6, 51.5, 50.2, 45.7, 45.2, 43.0, 38.9, 38.5, 36.4, 33.3, 32.6, 31.6, 31.0, 30.2, 23.7, 22.1, 21.2, 19.8, 19.6, 18.9, 15.1, 14.3, 10.1, 8.9; MS (ESI) m/z 918 (M+H)$^+$; Anal. Calcd for $C_{48}H_{72}FN_3O_{13}$ (918.11): C, 62.80; H, 7.90; N, 4.57. Found: C, 62.76; H, 7.99; N, 4.42.

Example 31
11-Deoxy-11-[carboxy(4-fluorophenethyl)amino]-3-O-[4-(s)-methyl-oxazolidin-2-one]carbamoyl-5-O-(3'-N-desmethyl-3'-N-n-propyl)desosaminyl-6-O-methyl-erythronolide A 11,12-(cyclic carbamate)

The title compound was prepared following the procedure described for Example 16, substituting 4-fluorophenethylamine for 3,4-dichlorophenethylamine. The crude product was purified by silica gel column chromatography (97:3 CH$_2$Cl$_2$:i-PrOH) to give a colorless, amorphous solid: $R_f$=0.30 (19:1 CH$_2$Cl$_2$:i-PrOH); IR (microscope) υ 3453, 2972, 2939, 1824, 1801, 1759, 1739, 1511, 1459, 1381, 1350, 1307, 1169, 1107, 1064 cm$^{-1}$; $^{13}$C NMR (125 MHz, CDCl$_3$) δ 215.7, 174.0, 161.5 (d, J=243 Hz), 157.1, 151.3, 151.1, 134.4 (d, J=4 Hz), 130.3 (d, J=8 Hz), 115.1 (d, J=22 Hz), 103.0, 82.7, 81.3, 79.6, 78.5, 76.8, 70.2, 69.7, 68.6, 65.7, 60.6, 55.2, 51.4, 50.2, 45.7, 45.2, 42.9, 38.9, 38.5, 36.8, 36.3, 32.6, 29.5, 22.0, 21.2 (2C), 19.7, 19.5, 18.9, 15.0, 14.2 (2C), 11.5, 10.1, 8.8; MS (ESI) m/z 892 (M+H)$^+$; Anal. Calcd for $C_{46}H_{70}FN_3O_{13}$ (892.07): C, 61.94; H, 7.91; N, 4.71. Found: C, 62.06; H, 7.81; N, 4.42.

Example 32
11-Deoxy-11-[carboxy(4-fluorophenethyl)amino]-3-O-[4-(s)-methyl-oxazolidin-2-one]carbamoyl-5-O-(3'-N-desmethyl-3'-N-isopropyl)desosaminyl-6-O-methyl-erythronolide A 11,12-(cyclic carbamate)

The title compound was prepared following the procedure described for Example 19, substituting 4-fluorophenethylamine for 3,4-dichlorophenethylamine. The crude product was purified by silica gel column chromatography (97:3 CH$_2$Cl$_2$:i-PrOH) to give a colorless, amorphous solid: $R_f$=0.30 (19:1 CH$_2$Cl$_2$:i-PrOH); IR (microscope) υ 3444, 2973, 2939, 1824, 1801, 1759, 1739, 1511, 1459, 1380, 1350, 1307, 1232, 1169, 1106, 1065, 1048 cm$^{-1}$; $^{13}$C NMR (125 MHz, CDCl$_3$) δ 215.7, 174.0, 161.5 (d, J=243 Hz), 157.1, 151.3, 151.1, 134.4 (d, J=3 Hz), 130.3 (d, J=8 Hz), 115.1 (d, J=22 Hz), 103.0, 82.7, 81.3, 79.7, 78.5, 76.8, 69.9, 69.6, 68.6, 62.8, 60.6, 52.9, 51.4, 50.2, 45.7, 45.2, 42.9, 38.9, 38.5, 36.3, 33.1, 32.6, 30.9, 22.0, 21.2, 20.9, 20.3, 19.7, 19.5, 18.9, 15.1, 14.2, 10.1, 8.9; MS (ESI) m/z 892 (M+H)$^+$; Anal. Calcd for $C_{46}H_{70}FN_3O_{13}$ (892.07): C, 61.94; H, 7.91; N, 4.71. Found: C, 62.12; H, 7.83; N, 4.52.

Example 33
11-Deoxy-11-[carboxy(3-chloro-4-fluorophenethyl)amino]-3-O-[4-(s)-methyl-oxazolidin-2-one]carbamoyl-5-O-(3'-N- desmethyl-3'-N-cyclopropylmethyl)desosaminyl-6-O-methyl-erythronolide A 11,12-(cyclic carbamate)

The title compound was prepared following the procedure described in Scheme 3, substituting 3-chloro-4-fluorophenethylamine for 3,4-dichlorophenethylamine. The crude product was purified by silica gel column chromatography (3:2 EtOAc:CH$_3$CN) to give a colorless, amorphous solid: R$_f$=0.50 (9:1 CHCl$_3$:MeOH); IR (microscope) υ 3449, 2975, 2941, 1824, 1801, 1758, 1738, 1502, 1458, 1380, 1350, 1307, 1271, 1169, 1106, 1063 cm$^{-1}$; $^{13}$C NMR (125 MHz, CDCl$_3$) δ 215.8, 174.1, 157.1, 156.8 (d, J=247 Hz), 151.3, 151.0, 135.9 (d, J=4 Hz), 131.0, 128.5 (d, J=7 Hz), 120.5 (d, J=17 Hz), 116.3 (d, J=21 Hz), 102.9, 82.8, 81.2, 79.3, 78.5, 76.7, 70.1, 69.8, 68.6, 64.8, 60.5, 58.7, 51.4, 50.3, 45.7, 45.0, 42.9, 38.9, 38.5, 36.9, 36.3, 32.4, 29.5, 21.9, 21.2, 19.7, 19.5, 18.9, 15.0, 14.3, 14.2, 10.1, 9.9, 8.8, 4.3, 3.4; MS (ESI) m/z 938 (M+H)$^+$; Anal. Calcd for C$_{47}$H$_{69}$ClFN$_3$O$_{13}$ (938.523): C, 60.15; H, 7.41; N, 4.48. Found: C, 59.88; H, 7.29; N, 4.28.

Example 34
11-Deoxy-11-[carboxy(3-chloro-fluorophenethyl)amino]-3-O-[4-(S)-methyl-oxazolidin-2-one]carbamoyl-5-O-(3'-N-desmethyl-3'-N-cyclobutyl)desosaminyl-6-O-methyl-erythronolide A 11,12-(cyclic carbamate)

The title compound was prepared following the procedure described for Example 13, substituting 3-chloro-4-fluorophenethylamine for 3,4-dichlorophenethylamine. The crude product was purified by silica gel column chromatography (2:3 acetone:hexanes) to give a colorless, amorphous solid: R$_f$=0.50 (1:1 acetone:hexanes); IR (microscope) υ 3454, 2975, 2940, 1824, 1801, 1758, 1739, 1502, 1458, 1380, 1350, 1307, 1169, 1106, 1063 cm$^{-1}$; $^{13}$C NMR (75 MHz, CDCl$_3$) δ 215.8, 174.0, 157.1, 156.9 (d, J=242 Hz), 151.3, 151.1, 135.9 (d, J=5 Hz), 131.0, 128.5 (d, J=7 Hz), 120.6 (d, J=19 Hz), 116.4 (d, J=21 Hz), 103.1, 82.8, 81.3, 79.7, 78.5, 76.8, 69.8, 69.6, 68.6, 60.6, 60.3, 56.9, 51.5, 50.2, 45.7, 45.1, 42.9, 38.9, 38.5, 36.4, 32.4, 31.1, 29.6, 28.5, 28.1, 22.0, 21.2, 19.8, 19.5, 18.9, 15.1, 14.3, 14.2, 14.1, 10.1, 8.9; MS (ESI) m/z 938 (M+H)$^+$; Anal. Calcd for C$_{47}$H$_{69}$ClFN$_3$O$_{13}$ (938.523): C, 60.15; H, 7.41; N, 4.48. Found: C, 59.86; H, 7.43; N, 4.27.

Example 35
11-Deoxy-11-[carboxy(3-chloro-4-fluorophenethyl)amino]-3-O-[4-(S)-methyl-oxazolidin-2-one]carbamoyl-5-O-(3'-N-desmethyl-3'-N-cyclopentyl)desosaminyl-6-O-methyl-erythronolide A 11,12-(cyclic carbamate)

The title compound was prepared following the procedure described for Example 14, substituting 3-chloro-4fluorophenethylamine for 3,4-dichlorophenethylamine. The crude product was purified by silica gel column chromatography (2:3 acetone:hexanes) to give a colorless, amorphous solid: R$_f$=0.50 (1:1 acetone:hexanes); IR (microscope) υ 3448, 2970, 2944, 1824, 1801, 1758, 1738, 1501, 1458, 1380, 1350, 1306, 1169, 1106, 1062 cm$^{-1}$; $^{13}$C NMR (75 MHz, CDCl$_3$) δ 215.8, 174.1, 157.1, 156.8 (d, J=244 Hz), 151.3, 151.1, 135.9 (d, J=4 Hz), 131.0, 128.5 (d, J=7 Hz), 120.6 (d, J=18 Hz), 116.4 (d, J=21 Hz), 103.1, 82.8, 81.3, 79.6, 78.5, 76.8, 69.8, 68.6, 63.7, 63.1, 60.6, 51.4, 50.3, 45.7, 45.1, 42.9, 38.9, 38.5, 36.4, 33.3, 32.4, 31.6, 31.0, 30.1, 23.7, 22.0, 21.3, 19.8, 19.6, 18.9, 15.0, 14.3, 14.2, 10.1, 8.9; MS (ESI) m/z 952 (M+H)$^+$; Anal. Calcd for C$_{48}$H$_{71}$ClFN$_3$O$_{13}$.0.25H$_2$O (957.054): C, 60.24; H, 7.53; N, 4.39. Found: C, 60.14; H, 7.50; N, 4.12.

Example 36
11-Deoxy-11-[carboxy(4-chloro-3-fluorophenethyl)amino]-3-O-[4-(S)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate)

The title compound was prepared following the procedure described in Scheme 3, substituting 4-chloro-3-fluorophenethylamine for 3,4-dichlorophenethylamine. The crude product was purified by silica gel column chromatography (97:3 CH$_2$Cl$_2$:i-PrOH) to give a colorless, amorphous solid: R$_f$=0.45 (23:2 CH$_2$Cl$_2$:i-PrOH); IR (microscope) υ 3456, 2975, 2940, 1824, 1801, 1759, 1738, 1459, 1424, 1381, 1350, 1307, 1169, 1107, 1066 cm$^{-1}$; $^{13}$C NMR (75 MHz, CDCl$_3$) δ 215.8, 174.1, 157.9 (d, J=248 Hz), 157.1, 151.3, 151.1, 139.9 (d, J=7 Hz), 130.3, 125.4 (d, J=4 Hz), 118.5 (d, J=18 Hz), 117.1 (d, J=21 Hz), 102.9, 82.8, 81.2, 79.3, 78.5, 76.7, 70.1, 69.7, 68.6, 64.8, 60.6, 58.7, 51.4, 50.2, 45.7, 44.8, 42.9, 38.9, 38.5, 36.9, 36.3, 32.7, 29.6, 22.0, 21.2, 19.6, 19.5, 18.9, 15.0, 14.3, 14.2, 10.0, 9.9, 8.8, 4.3, 3.5; MS (ESI) m/z 938 (M+H)$^+$; Anal. Calcd for C$_{47}$H$_{69}$ClFN$_3$O$_{13}$ (938.523): C, 60.15; H, 7.41; N, 4.48. Found: C, 60.37; H, 7.40; N, 4.41.

Example 37
11-Deoxy-11-[carboxy(3,4-dichlorophenethyl)amino]-3-O-[4-(R)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate)

The title compound was prepared following an analogous procedure to that described in Scheme 3, substituting 4-(R)-methyl-oxazolidin-2-one for 4-(S)-methyl-oxazolidin-2-one. The crude product was purified by silica gel column chromatography (9:1 EtOAc:acetone) to give a colorless, amorphous solid: R$_f$=0.45 (9:1 CHCl$_3$:MeOH); IR (microscope) υ 3446, 2975, 2941, 1823, 1758, 17370, 1714, 1459, 1381, 1352, 1169, 1105, 1066 cm$^{-1}$; $^{13}$C NMR (100 MHz, CDCl$_3$) δ 215.6, 173.8, 157.0, 152.0, 150.8, 139.0, 132.1, 130.9, 130.2, 130.1, 128.3, 104.5, 83.2, 82.7, 81.1, 78.5, 76.7, 69.4, 69.1, 68.6, 65.3, 60.7, 58.8, 51.0, 50.0, 45.5, 44.8, 43.0, 38.8, 38.6, 36.5, 36.3, 32.5, 29.5, 21.9, 21.0, 20.0, 19.6, 18.7, 15.3, 14.2 (2C), 10.0, 9.0, 8.9, 4.4, 3.7; MS (APCI) m/z 954 (M+H)$^+$; Anal. Calcd for C$_{47}$H$_{69}$Cl$_2$N$_3$O$_{13}$ (954.973): C, 59.11; H, 7.28; N, 4.40. Found: C, 58.97; H, 7.18; N, 4.22.

Example 38
11-Deoxy-11-[carboxy(3,4-dichlorophenethyl)amino]-3-O-[4-(S)-ethyl-oxazolidin-2-one]carbamoyl-5-O-(3'-N-desmethyl-3'-N-cyclopropylmethyl)desosaminyl-6-O-methyl-erythronolide A 11,12-(cyclic carbamate)

The title compound was prepared following an analogous procedure to that described in Scheme 3, substituting 4-(S)-ethyl-oxazolidin-2-one for 4-(S)-methyl-oxazolidin-2-one. The crude product was purified by silica gel column chromatography (9:1 EtOAc:acetone) to give a colorless, amorphous solid: R$_f$=0.40 (9:1 CHCl$_3$:MeOH); IR (microscope) υ 3448, 2974, 2940, 1822, 1796, 1757, 1737, 1459, 1381, 1363, 1309, 1234, 1169, 1109, 1067 cm$^{-1}$; $^{13}$C NMR (100 MHz, CDCl$_3$) δ 215.8, 174.1, 157.0, 151.5, 151.2, 139.1, 132.1, 130.9, 130.2, 130.1, 128.3, 102.8, 82.8, 81.1, 79.3, 78.5, 76.7, 69.9, 69.4, 66.2, 64.5, 60.5, 58.7, 56.0, 50.2, 45.6, 44.8, 42.8, 38.8, 38.4, 36.6, 36.3, 32.5, 29.8, 25.4, 21.9, 21.1, 19.5, 18.8, 15.0, 14.2, 14.1, 10.0, 9.3, 8.7, 7.9, 4.4, 3.5; MS (ESI) m/z 968 (M+H)$^+$; Anal. Calcd for C$_{48}$H$_{71}$Cl$_2$N$_3$O$_{13}$.H$_2$O (987.014): C, 58.41; H, 7.46; N, 4.26. Found: C, 58.29; H, 7.30; N, 4.13.

Example 39
11-Deoxy-11-[carboxy(3,4-dichlorophenethyl)amino]-3-O-[5-(R)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate)

The title compound was prepared following an analogous procedure to that described in Scheme 3, substituting 5-(R)-methyl-oxazolidin-2-one for 4-(S)-methyl-oxazolidin-2-one. The crude product was purified by silica gel column chromatography (9:1 EtOAc:acetone) to give a colorless, amorphous solid: $R_f$=0.40 (9:1 $CHCl_3$:MeOH); IR (KBr) υ 3442, 2975, 2940, 1826, 1758, 1738, 1714, 1458, 1384, 1299, 1169, 1105, 1067 $cm^{-1}$; $^{13}C$ NMR (75 MHz, $CDCl_3$) δ 215.7, 173.9, 157.1, 150.8, 139.1, 132.3, 131.0, 130.3 (2C), 128.4, 104.5, 82.8, 81.2, 78.6, 77.2, 76.9, 70.3, 69.8, 69.5, 65.5, 60.9, 58.9, 50.0, 45.7, 44.9, 43.0, 38.9, 38.6, 36.7, 36.4, 32.6, 29.7, 22.1, 21.1, 20.1, 19.6, 18.8, 15.2, 14.3 (2C), 10.1, 9.4, 8.9, 4.3, 3.8; MS (ESI) m/z 954 (M+H)$^+$; Anal. Calcd for $C_{47}H_{69}Cl_2N_3O_{13}$ (954.973): C, 59.11; H, 7.28; N, 4.40. Found: C, 59.01; H, 7.16; N, 4.04.

Example 40

11-Deoxy-11-[carboxy(3,4-dichlorophenethyl)amino]-3-O-[4-(S)-methyl-thiazolidin-2-one]carbamoyl-5-O-(3'-N-desmethyl-3'-N-cyclopropylmethyl)desosaminyl-6-O-methyl-erythronolide A 11,12-(cyclic carbamate)

The title compound was prepared following an analogous procedure to that described in Scheme 3, substituting 4-(S)-methyl-thiazolidin-2-one for 4-(S)-methyl-oxazolidin-2-one. The crude product was purified by silica gel column chromatography (9:1 EtOAc:acetone) to give a colorless, amorphous solid: $R_f$=0.40 (9:1 $CHCl_3$:MeOH); IR (KBr) υ 3446, 2974, 2940, 1759, 1735, 1717, 1457, 1280, 1234, 1168, 1066, 1050 $cm^{-1}$; $^{13}C$ NMR (75 MHz, $CDCl_3$) δ 215.8, 174.1, 157.1, 150.9, 139.2, 132.3, 131.0, 130.3, 130.2, 128.4, 102.9, 82.9, 81.2, 79.6, 78.5, 76.8, 70.0, 69.6, 64.8, 64.3, 60.7, 58.9, 55.0, 50.2, 45.7, 44.9, 43.0, 38.9, 38.5, 36.8, 36.3, 32.6, 29.9, 22.0, 21.2, 19.5, 19.2, 18.9, 15.1, 14.3, 14.2, 10.1, 9.5, 8.9, 4.4, 3.7; MS (ESI) m/z 970 (M+H)$^+$; Anal. Calcd for $C_{47}H_{69}Cl_2N_3O_{12}S$ (971.035): C, 58.13; H, 7.16; N, 4.33. Found: C, 57.95; H, 7.24; N, 4.23.

Example 41

11-Deoxy-11-[carboxy(3,4-dichlorophenethyl)amino]-3-O-[4-(S)-methyl-oxazolidin-2-thione]carbamoyl-5-O-(3'-N-desmethyl-3'-N-cyclopropylmethyl)desosaminyl-6-O-methyl-erythronolide A 11,12-(cyclic carbamate) (Compound 30)

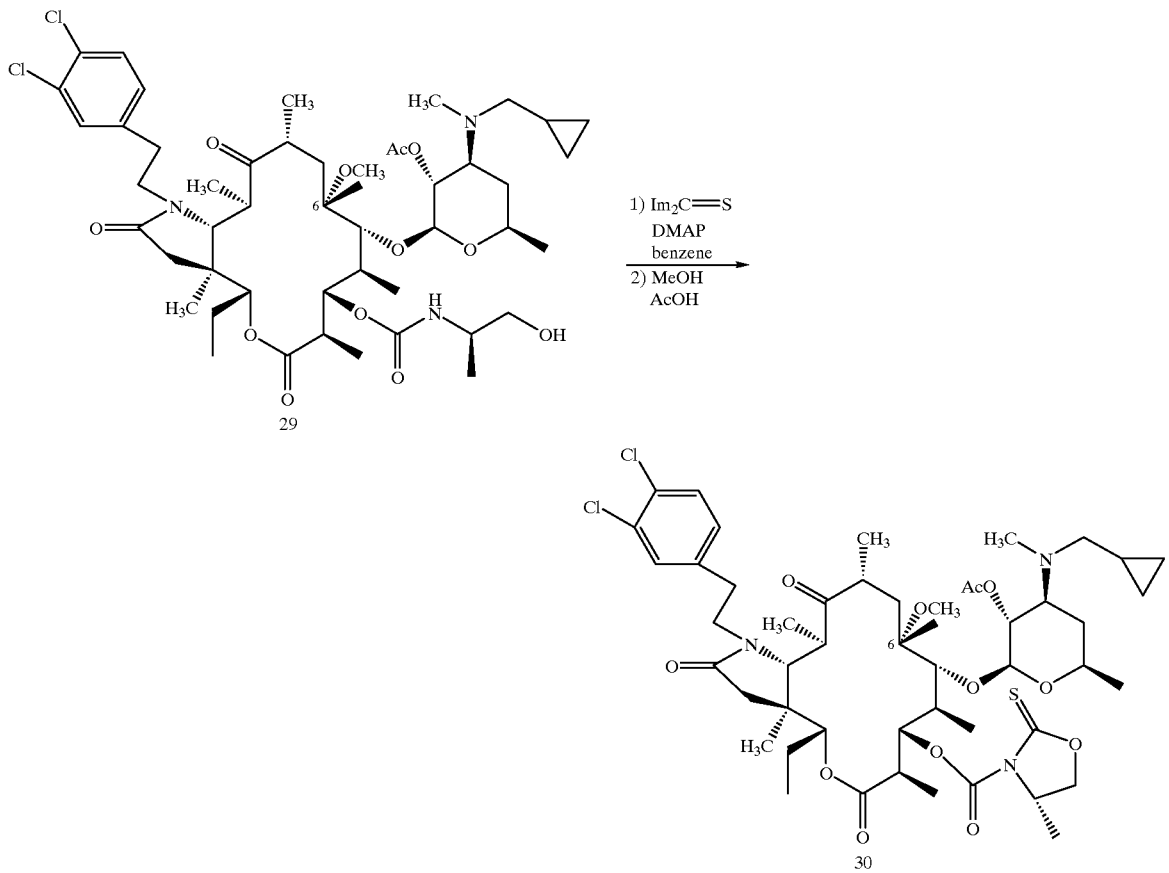

Example 41
Step 1: 11-Deoxy-11-[carboxy(3,4-dichlorophenethyl)amino]-3-O-[2-(S)-amino-1-propanol]carbamoyl-5-O-(2'-O-acetyl-3'-N-desmethyl-3'-N-cyclopropylmethyl)desosaminyl-6-O-methyl-erythronolide A 11,12-(cyclic carbamate) (Compound 29, Scheme 5)

The title compound was prepared following the procedure described in Scheme 2 for 11-deoxy-11-[carboxy(4-chlorophenethyl)amino]-3-O-[2-(R)-amino-1-propanol]carbamoyl-5-O-(2'-O-acetyl-3'-N-desmethyl-3'-N-isopropyl)desosaminyl-6-O-methyl-erythronolide A 11,12-(cyclic carbamate) (Compound 15), substituting cyclopropanecarboxaldehyde for acetone, substituting 3,4-dichlorophenethylamine for 4-chlorophenethylamine, and substituting L-alaninol for D-alaninol. The crude product was purified by silica gel column chromatography (2:1 EtOAc:hexanes) to give a colorless, amorphous solid: $R_f$=0.35 (9:1 CHCl$_3$:MeOH); $^{13}$C NMR (75 MHz, CDCl$_3$) δ 215.8, 174.3, 169.9, 157.1, 156.3, 139.1, 132.2, 131.0, 130.3, 130.2, 128.4, 100.6, 82.9, 80.0, 78.4, 77.9, 76.4, 71.6, 69.0, 66.2, 62.7, 60.7, 58.7, 50.2, 49.1, 45.7, 44.9, 43.3, 38.9, 38.3, 37.4, 35.6, 32.5, 31.8, 22.0, 21.4, 20.1, 19.5, 18.9, 17.3, 14.8, 14.3, 14.2, 10.1, 9.9, 8.8, 4.1, 3.5; MS (ESI) m/z 970 (M+H)$^+$.

Step 2: 11-Deoxy-11-[carboxy(3,4-dichlorophenethyl)amino]-3-O-[4-(S)-methyl-oxazolidin-2-thione]carbamoyl-5-O-(3'-N-desmethyl-3'-N-cyclopropylmethyl)desosaminyl-6-O-methyl-erythronolide A 11,12-(cyclic carbamate) (Compound 30, Scheme 5)

To a solution of 11-deoxy-11-[carboxy(3,4-dichlorophenethyl)amino]-3-O-[2-(S)-amino-1-propanol]carbamoyl-5-O-(2'-O-acetyl-3'-N-desmethyl-3'-N-cyclopropylmethyl)desosaminyl-6-O-methyl-erythronolide A 11,12-(cyclic carbamate) (Compound 29) (75 mg, 77 μmol) in anhydrous benzene (3 mL) was added 1,1'-thiocarbonyldiimidazole (25 mg, 126 μmol). The reaction mixture was stirred at reflux under dry N$_2$ for 3 h, after which time TLC (9:1 CHCl$_3$:MeOH) indicated the reaction was complete. The mixture was concentrated, and the residue was subjected to column chromatography on silica gel (2:1 EtOAc:hexanes) to give a slightly crude product [68 mg, $R_f$=0.50 (9:1 CHCl$_3$:MeOH), MS (ESI) m/z 1080 (M+H)$^+$]. To a solution of this compound in anhydrous benzene (3 mL) was added 4-dimethylaminopyridine (10 mg, 82 μmol), and the reaction mixture was stirred at reflux under dry N$_2$ for 4 h, after which time TLC (EtOAc) indicated the reaction was complete. The mixture was concentrated, and the residue was purified by column chromatography on silica gel (3:2 EtOAc:hexanes) to give the 2'-O-acetate of compound 30 as a colorless, amorphous solid [(53 mg, 68% from compound 29), $R_f$=0.35 (EtOAc), MS (APCI) m/z 1012 (M+H)$^+$]. A solution of this compound (30 mg, 30 μmol) in MeOH (2 mL) and AcOH (5 μL) was stirred at rt 36 h, concentrated and purified by column chromatography on silica gel (9:1 EtOAc:acetone) to give compound 30 as a colorless, amorphous solid (25 mg, 87%): $R_f$=0.30 (9:1 CHCl$_3$:MeOH); IR (microscope) υ 3455, 2974, 2939, 1757, 1714, 1458, 1378, 1352, 1248, 1170, 1104, 1067, 1051 cm$^{-1}$; $^{13}$C NMR (75 MHz, CDCl$_3$) δ 215.8, 173.9, 157.1, 151.6, 139.2, 131.0, 130.3, 130.2, 128.4, 102.8, 82.8, 82.5, 79.5, 78.6, 76.9, 73.2, 69.9, 69.5, 64.7, 60.7, 58.8, 55.8, 50.3, 45.7, 44.9, 43.0, 39.0, 38.5, 36.8, 36.3, 32.6, 29.7, 22.0, 21.2, 19.6, 19.4, 18.9, 15.3, 14.3, 14.2, 10.1, 9.3, 4.6, 3.7; MS (APCI) m/z 970 (M+H)$^+$; Anal. Calcd for C$_{47}$H$_{69}$Cl$_2$N$_3$O$_{12}$S (971.035): C, 58.13; H, 7.16; N, 4.33. Found: C, 58.00; H, 7.14; N, 4.14.

Example 42
11-Deoxy-11-[carboxy(3,4-dichlorophenethyl)amino]-3-O-[4-(S)-methyl-oxazolidin-2-one]carbamoyl-5-O-(3'-bis-N-desmethyl-3'-bis-N-cyclopropylmethyl)desosaminyl-6-O-methyl-erythronolide A 11,12-(cyclic carbamate) (Compound 27, Scheme 4)

Step 1: 11-Deoxy-11-[carboxy(3,4-dichlorophenethyl)amino]-6-O-methyl-erythromycin A 11,12-(cyclic carbamate) (Compound 23, Scheme 4).

A solution of 2'-O-acetyl-4"-O-trimethylsilyl-11-deoxy-11-[carboxy(3,4-dichlorophenethyl)amino]-6-O-methyl-erythromycin A 11,12-(cyclic carbamate) (Compound 19, Scheme 3) (5.74 g, 5.42 mmol) in MeOH (250 mL) was heated at 55° C. for 24 h, after which time TLC (9:1 CH$_2$Cl$_2$:MeOH) indicated the reaction was complete. The product crystallized upon cooling and addition of H$_2$O to give colorless crystals [(5.24 g, 95%), mp=112–114° C., $R_f$=0.65 (9:1 CH$_2$Cl$_2$:MeOH), MS (ESI) m/z 1017 (M+H)$^+$]. To a solution of this compound in THF (50 mL) was added a solution of tetrabutylammonium fluoride (1.0 M in THF, 5.4 mL), and the reaction mixture was stirred at rt for 2 h, after which time TLC (90:8:1 CHCl$_3$:MeOH:NH$_4$OH) indicated the reaction was complete. The mixture was partitioned between EtOAc (300 mL) and H$_2$O (300 mL), and the organic phase was washed with saturated aq. NaHCO$_3$ (200 mL), H$_2$O (200 mL) and brine (200 mL), and dried over Na$_2$SO$_4$. The drying agent was filtered off, and solvent was removed in vacuo to give a crude product which crystallized from CH$_3$CN to give compound 23 as colorless crystals (4.82 g, 94% from compound 20): mp=240–243° C.; $R_f$=0.45 (CHCl$_3$:MeOH:NH$_4$OH); $^{13}$C NMR (75 MHz, CDCl$_3$) δ 216.2, 176.4, 157.2, 139.3, 132.1, 131.0, 130.2, 130.1, 128.4, 102.9, 96.2, 82.8, 80.1, 78.9, 77.9, 77.8, 76.2, 72.6, 70.9, 68.9, 65.8, 65.6, 60.3, 50.6, 49.5, 45.5, 45.3, 44.8, 40.2 (2C), 39.0, 38.9, 34.8, 32.6, 28.5, 21.9, 21.5 (2C), 20.2, 18.9, 18.7, 16.0, 14.2, 14.1, 10.2, 9.0; MS (FAB) m/z 945 (M+H)$^+$.

Step 2: 3'-Bis-N-desmethyl-3'-bis-N-cyclopropylmethyl-11-deoxy-11-[carboxy(3,4-dichlorophenethyl)amino]-6-O-methyl-erythromycin A 11,12-(cyclic carbamate) (Compound 24, Scheme 4)

To a solution of 11-deoxy-11-[carboxy(3,4-dichlorophenethyl)amino]-6-O-methyl-erythromycin A 11,12-(cyclic carbamate) (Compound 23) (10.0 g, 10.57 mmol) in 10% aq. MeOH (500 mL) was added I$_2$ (5.40 g, 21.14 mmol) and 1 M K$_3$PO$_4$ (53.0 mL). The reaction vessel was equipped with a reflux condenser, and the dark colored mixture was placed under a 500 W lamp and stirred for 1 h (dark color slowly dissipated), after which time TLC (CHCl$_3$:MeOH) indicated the reaction to be complete. The mixture was partitioned between 0.5 M Na$_2$S$_2$O$_3$ (500 mL) and CHCl$_3$ (3×500 mL), and the combined organic layers were washed with H$_2$O (500 mL) and brine, then dried over MgSO$_4$. The drying agent was filtered off, solvent was removed in vacuo, and the crude product was purified by column chromatography on silica gel (9:1 CHCl$_3$:MeOH) to give the 3'-monomethyl derivative of compound 23 as an amorphous solid [(9.48 g, 96%), mp 136–142° C. (aq. CH$_3$CN), $R_f$=0.35 (90:10:1 CHCl$_3$:MeOH:NH$_4$OH), MS (FAB) m/z 931 (M+H)$^+$]. To a solution of this compound (2.07 g, 2.19 mmol) in MeOH (50 mL) was added a solution of K$_3$PO$_4$ (2.32 g in 5 mL H$_2$O, 11.0 mmol) and I$_2$ (1.11 g, 4.38 mmol). The reaction vessel was equipped with a reflux condenser, and the dark colored mixture was placed under a 500 W lamp and stirred for 45 min (dark color slowly dissipated), after which time TLC (90:10:1 CHCl$_3$:MeOH:NH$_4$OH) indicated partial conversion to a more polar product. The mixture was concentrated to ca. 10 mL and partitioned between EtOAc (400 mL) and saturated aq. NaHCO$_3$ (100 mL), and the organic phase was washed with H$_2$O (300 mL) and brine, then dried over Na$_2$SO$_4$. The drying agent was filtered off, solvent was removed in vacuo, and the residue was resubjected to the reaction conditions described above for 1 h, after which time TLC indicated the reaction was complete. The mixture was worked-up as before to give a crude product which crystallized from CH$_3$CN to give the 3'-bis-desmethyl derivative of compound 23 [(1.25 g, 62%), mp=223–225° C. (EtOAc), $R_f$=0.30 (90:10:1 CHCl$_3$:MeOH:NH$_4$OH), MS (FAB) m/z 917 (M+H)$^+$].

To a solution of the above compound (842 mg, 0.92 mmol) in MeOH (20 mL) was added cyclopropanecarboxaldehyde (685 μL, 9.17 mmol), AcOH (105 μL, 1.83 mmol), and NaCNBH$_3$ (115 mg, 1.83 mmol). The reaction mixture was stirred at rt 24 h, after which time TLC (9:1 EtOAc:MeOH) indicated the reaction was complete. The mixture was diluted with EtOAc (300 mL), washed with saturated NH$_4$Cl (200 μL), saturated aq. NaHCO$_3$ (200 mL), H$_2$O (200 mL) and brine, and the organic phase was dried over MgSO$_4$. The drying agent was filtered off, and solvent was removed in vacuo to give a crude product which was purified by column chromatography on silica gel (2:1 EtOAc:hexanes) to give compound 24 as a colorless, amorphous solid (780 mg, 83%): R$_f$=0.40 (9:1 CHCl$_3$:MeOH); $^{13}$C NMR (75 MHz, CDCl$_3$) δ 216.3, 176.3, 157.2, 139.3, 132.2, 131.0, 130.3, 130.1, 128.4, 103.1, 96.0, 82.8, 80.3, 78.9, 77.8, 76.2, 72.6, 70.4, 69.1, 65.8, 61.7, 60.4, 54.5, 50.6, 49.5, 45.6, 45.3, 44.8, 39.1, 39.0 (2C), 34.8, 32.6, 30.3, 21.9, 21.5 (2C), 20.2, 18.9, 18.6, 16.0, 14.2, 14.1, 10.4, 10.2, 9.0, 5.5, 2.7; MS (APCI) m/z 1025 (M+H)$^+$.

Step 3: 2'-O-Acetyl-3'-bis-N-desmethyl-3'-bis-N-cyclopropylmethyl-11-deoxy-11-[carboxy(3,4-dichlorophenethyl)amino]-6-O-methyl-erythromycin A 11,12-(cyclic carbamate) (Compound 25, Scheme 4)

To a solution of 3'-bis-N-desmethyl-3'-bis-N-cyclopropylmethyl-11-deoxy-11-[carboxy(3,4-dichlorophenethyl)amino]-6-O-methyl-erythromycin A 11,12-(cyclic carbamate) (Compound 24) (700 mg, 0.68 mmol) in anhydrous CH$_2$Cl$_2$ (7 mL) at 0° C. under dry N$_2$ was added triethylamine (100 μL, 0.72 mmol) and acetic anhydride (110 μL, 1.06 mmol). The reaction mixture was allowed to warm to rt and stir for 36 h, after which time TLC (9:1 CHCl$_3$:MeOH) indicated the reaction was complete. The mixture was partitioned between 0.5 M NaH$_2$PO$_4$ (100 mL) and CHCl$_3$ (3×50 mL), and the combined organic layers were dried over Na$_2$SO$_4$. The drying agent was filtered off, and solvent was removed in vacuo to give a crude product which crystallized from CH$_3$CN to give compound 25 as small colorless needles. The filtrate was concentrated in vacuo, and the residue was purified by column chromatography on silica gel (1:2 EtOAc:hexanes) to give additional compound 25 as a colorless, amorphous solid (combined yield=0.63 g, 86%): mp>260° C. (d); R$_f$=0.65 (9:1 CHCl$_3$:MeOH); $^{13}$C NMR (100 MHz, CDCl$_3$) δ 216.3, 176.1, 169.7, 157.1, 139.2, 132.1, 131.0, 130.2, 130.1, 128.3, 100.8, 95.8, 82.8, 80.0, 78.8, 77.8, 77.5, 76.2, 72.7, 71.5, 68.5, 65.8, 60.3, 59.4, 54.3, 50.4, 49.3, 45.5, 45.2, 44.8, 38.9, 38.7, 38.5, 34.8, 32.5, 31.7, 21.9, 21.5, 21.3, 21.2, 20.1, 18.7, 18.6, 16.0, 14.3, 14.1, 10.3, 10.2, 8.9, 5.3, 2.1; MS (ESI) m/z 1067 (M+H)$^+$.

Step 4: 11-Deoxy-11-[carboxy(3,4-dichlorophenethyl)amino]-5-O-(2'-O-acetyl-3'-bis-N-desmethyl-3'-bis-N-cyclopropylmethyl)desosaminyl-6-O-methyl-erythronolide A 11,12-(cyclic carbamate) (Compound 26, Scheme 4)

A solution of 2'-O-acetyl-3'-bis-N-desmethyl-3'-bis-N-cyclopropylmethyl-11-deoxy-11-[carboxy(3,4-dichlorophenethyl)amino]-6-O-methyl-erythromycin A 11,12-(cyclic carbamate) (Compound 25) (620 mg, 0.58 mmol) in 50% aq. EtOH (8 mL) and N HCl (2 mL) was stirred at rt 3 days, after which time TLC (1:2 EtOAc:hexanes) indicated the reaction was complete. The mixture was poured into saturated aq. NaHCO$_3$ (100 mL) and extracted with CHCl$_3$ (3×50 mL). The combined organic layers were dried over Na$_2$SO$_4$, then filtered and concentrated to give a crude product which was purified by column chromatography on silica gel (1:3 EtOAc:hexanes) to give compound 26 as a colorless, amorphous solid (490 mg, 93%): R$_f$=0.20 (1:2 EtOAc:hexanes); $^{13}$C NMR (100 MHz, CDCl$_3$) δ 215.8, 175.2, 169.7, 157.1, 139.1, 132.1, 130.9, 130.2, 130.1, 128.3, 100.1, 83.0, 80.4, 78.5, 77.4, 76.1, 71.4, 69.1, 60.8, 59.7, 54.6, 49.8, 45.7, 44.9, 44.2, 38.8, 38.3, 36.0, 32.5, 22.1, 21.2, 21.1, 19.3, 19.0, 18.8, 15.2, 14.3, 14.2, 10.3, 10.1, 7.6, 5.1, 2.5; MS (ESI) m/z 909 (M+H)$^+$.

Step 5: 11-Deoxy-11-[carboxy(3,4-dichlorophenethyl)amino]-3-O-[4-(s)-methyl-oxazolidin-2-one]carbamoyl-5-O-(3'-bis-N-desmethyl-3'-bis-N-cyclopropylmethyl)desosaminyl-6-O-methyl-erythronolide A 11,12-(cyclic carbamate) (Compound 27, Scheme 4)

To a solution of 11-deoxy-11-[carboxy(3,4-dichlorophenethyl)amino]-5-O-(2'-O-acetyl-3'-bis-N-desmethyl-3'-bis-N-cyclopropylmethyl)desosaminyl-6-O-methyl-erythronolide A 11,12-(cyclic carbamate) (Compound 26) (0.45 g, 0.49 mmol) in anhydrous CH$_2$Cl$_2$ (5 mL) under dry N$_2$ was added 1,1'-carbonyldiimidazole (160 mg, 0.99 mmol) and 4-dimethylaminopyridine (60 mg, 0.49 mmol). The reaction mixture was stirred at rt for 3 days, after which time TLC (EtOAc) indicated the reaction was complete. The mixture was partitioned between 0.5 M NaH$_2$PO$_4$ (50 mL) and CHCl$_3$ (3×40 mL), and the combined organic layers were dried over Na$_2$SO$_4$. The drying agent was filtered off, and solvent was removed in vacuo to give a crude product which was purified by column chromatography on silica gel (1:1 EtOAc:hexane) to give the 3-O-(acylimidazole)carbamate of compound 26 as a colorless, amorphous solid [(0.50 g, 100%), R$_f$=0.55 (EtOAc), MS (APCI) m/z 1003 (M+H)$^+$]. To a solution of this compound (0.50 g, 0.50 mmol) and 4-(s)-methyl-oxazolidin-2-one (150 mg, 1.48 mmol) in anhydrous THF (10 mL) at −78° C. under dry N$_2$ was added a solution of lithium bis(trimethylsilyl) amide (1.0 M in hexanes, 0.50 mL) dropwise. The mixture was stirred at −78° C. for 30 min, then anhydrous DMF (3 mL) was slowly added over ca. 5 min. The reaction mixture was allowed to warm to −35° C. and stir for 8 h, after which time TLC (1:1 EtOAc:hexanes) indicated the reaction was complete. The reaction was quenched cold with saturated aq. NH$_4$Cl (5 mL) and partitioned between H$_2$O (50 mL) and EtOAc (3×50 mL). The combined organic layers were dried over Na$_2$SO$_4$, then filtered and concentrated to give a crude product which was purified by column chromatography on silica gel (1:2 EtOAc:hexanes) to give the 2'-O-acetate of compound 27 as a colorless, amorphous solid [(0.40 g, 80%), R$_f$=0.25 (1:1 EtOAc:hexane), MS (APCI) m/z 1036 (M+H)$^+$]. This compound was dissolved in MeOH (10 mL) and AcOH (25 μL) and stirred at rt for 2 days, after which time TLC (EtOAc) indicated the reaction was complete. The solvent was removed in vacuo to give a crude product which was purified by column chromatography on silica gel (2:1 EtOAc:hexanes) to give compound 27 as a colorless, amorphous solid (0.37 g, 96%): R$_f$=0.25 (EtOAc); IR (microscope) υ 3448, 2975, 2939, 1824, 1801, 1759, 1738, 1460, 1380, 1350, 1307, 1169, 1107, 1066, 1047 cm$^{-1}$; $^{13}$C NMR (75 MHz, CDCl$_3$) δ 215.9, 174.1, 157.1, 151.3, 151.0, 139.2, 132.2, 131.0, 130.3, 130.2, 128.4, 102.8, 82.8, 81.1, 78.8, 78.5, 76.8, 70.1, 69.9, 68.6, 62.0, 60.5, 54.6, 51.4, 50.3, 45.7, 44.9, 42.9, 38.9, 38.5, 36.3, 32.6, 30.5, 22.0, 21.2, 19.7, 19.5, 19.0, 15.1, 14.3, 14.2, 10.3, 10.1, 8.9, 5.4, 2.8; MS (ESI) m/z 994 (M+H)$^+$; Anal. Calcd for C$_{50}$H$_{73}$Cl$_2$N$_3$O$_{13}$ (995.038): C, 60.35; H, 7.40; N, 4.22. Found: C, 60.36; H, 7.52; N, 3.99.

Example 43

11-Deoxy-11-[carboxy(3-chloro-4-fluorophenethyl)amino]-3-O-[4-(s)-methyl-oxazolidin-2-one]carbamoyl-5-O-(3'-bis-N-desmethyl-3'-bis-N-cyclopropylmethyl)desosaminyl-6-O-methyl-erythronolide A 11,12-(cyclic carbamate)

The title compound was prepared following the procedure described for Example 42, substituting 3-chloro-4-fluorophenethylamine for 3,4-dichlorophenethylamine. The crude product was purified by silica gel column chromatography (19:1 CHCl$_3$:acetone) to give a colorless, amorphous solid: R$_f$=0.30 (4:1 EtOAc:hexanes); IR (KBr) υ 3442, 2976, 2940, 1826, 1802, 1759, 1738, 1502, 1460, 1381, 1350, 1307, 1169, 1107, 1065 cm$^{-1}$; $^{13}$C NMR (100 MHz, CDCl$_3$) δ 215.8, 174.1, 157.0, 156.7 (d, J=246 Hz), 151.3, 151.0, 135.9 (d, J=4 Hz), 130.9, 128.5 (d, J=7 Hz), 120.5 (d, J=18 Hz), 116.3 (d, J=21 Hz), 102.7, 82.8, 81.0, 78.8, 78.5, 76.7, 70.0, 69.9, 68.5, 61.9, 60.5, 54.6, 51.4, 50.2, 45.7, 45.0, 42.8, 38.8, 38.4, 36.3, 32.4, 30.5, 21.9, 21.2, 19.6, 19.5, 18.9, 15.0, 14.2, 14.1, 10.2, 10.1, 8.8, 5.3, 2.8; MS (ESI) m/z 978 (M+H)$^+$; Anal. Calcd for C$_{50}$H$_{73}$ClFN$_3$O$_{13}$ (978.588): C, 61.37; H, 7.52; N, 4.29. Found: C, 61.28; H, 7.58; N, 4.08.

Example 44
11-Deoxy-11-[carboxy(4-chloro-3-fluorophenethyl)amino]-3-O-[4-(s)-methyl-oxazolidin-2-one]carbamoyl-5-O-(3'-bis-N-desmethyl-3'-bis-N-cyclopropylmethyl)desosaminyl-6-O-methyl-erythronolide A 11,12-(cyclic carbamate)

The title compound was prepared following the procedure described for Example 42, substituting 4-chloro-3-fluorophenethylamine for 3,4-dichlorophenethylamine. The crude product was purified by silica gel column chromatography (1:1 EtOAc:hexanes) to give a colorless, amorphous solid: R$_f$=0.25 (3:2 EtOAc:hexanes); IR (microscope) υ 3442, 2975, 2940, 1824, 1801, 1758, 1738, 1459, 1425, 1380, 1350, 1307, 1272, 1235, 1169, 1107, 1066, 1045 cm$^{-1}$; $^{13}$C NMR (100 MHz, CDCl$_3$) δ 215.8, 174.0, 157.8 (d, J=249 Hz), 157.0, 151.3, 151.0, 139.8 (d, J=6 Hz), 130.3, 125.3 (d, J=4 Hz), 118.5 (d, J=18 Hz), 117.1 (d, J=21 Hz), 102.7, 82.8, 81.0, 78.8, 78.5, 76.7, 70.0, 69.8, 68.5, 61.9, 60.5, 54.6, 51.4, 50.2, 45.7, 44.8, 42.8, 38.8, 38.4, 36.3, 32.7, 30.5, 21.9, 21.1, 19.6, 19.5, 18.9, 15.0, 14.2, 14.1, 10.2, 10.0, 8.8, 5.3, 2.8; MS (ESI) m/z 978 (M+H)$^+$; Anal. Calcd for C$_{50}$H$_{73}$ClFN$_3$O$_{13}$ (978.588): C, 61.37; H, 7.52; N, 4.29. Found: C, 61.76; H, 7.48; N, 3.90.

Example 45
11-Deoxy-11-[carboxy(3,4-dichlorophenethyl)amino]-3-O-[4-(s)-methyl-oxazolidin-2-one]carbamoyl-5-O-(3'-bis-N-desmethyl-3'-N-cyclopropylmethyl)desosaminyl-6-O-methyl-erythronolide A 11,12-(cyclic carbamate)

To a solution of 11-deoxy-11-[carboxy(3,4-dichlorophenethyl)amino]-3-O-[4-(s)-methyl-oxazolidin-2-one]carbamoyl-5-O-(3'-bis-N-desmethyl-3'-bis-N-cyclopropylmethyl)desosaminyl-6-O-methyl-erythronolide A 11,12-(cyclic carbamate) (Compound 27) (51 mg, 51 μmol) in i-PrOH (5 mL) was added NaOAc.3H$_2$O (35 mg, 0.26 mmol) and I$_2$ (16 mg, 62 μmol). The reaction vessel was equipped with a reflux condenser, and the dark colored mixture was stirred under a 500 W lamp 3 h, after which time TLC (EtOAc) indicated the reaction to be complete. The cooled mixture was partitioned between 0.5 M Na$_2$S$_2$O$_3$ (100 mL) and CHCl$_3$ (3×50 mL), and the combined organic layers were washed with saturated aq. NaHCO$_3$ (100 mL), H$_2$O (100 mL) and brine, then dried over MgSO$_4$. The drying agent was filtered off, and solvent was removed in vacuo to give a crude product which was purified by column chromatography on silica gel (19:1 CHCl$_3$:i-PrOH) to give an amorphous solid (18 mg, 37%): R$_f$=0.30 (23:2 CHCl$_3$:i-PrOH); IR (microscope) υ 3458, 2973, 2934, 1823, 1800, 1758, 1739, 1460, 1381, 1350, 1307, 1169, 1104, 1067, 1043 cm$^{-1}$; $^{13}$C NMR (100 MHz, CDCl$_3$) δ 215.6, 174.0, 157.1, 151.5, 151.2, 139.1, 132.2, 131.0, 130.3, 130.2, 128.4, 102.3, 82.8, 81.3, 79.7, 78.5, 76.8, 74.0, 69.3, 68.6, 60.7, 59.0, 51.5 (2C), 50.2, 45.6, 44.9, 42.9, 38.9, 38.6, 36.1, 32.6, 29.7, 22.0, 21.0, 19.5, 18.9, 15.0, 14.3 (2C), 10.9, 10.1, 9.1, 3.7, 3.4; MS (ESI) m/z 940 (M+H)$^+$.

Example 46
11-Deoxy-11-[carboxy(3,4-dichlorophenethyl)amino]-3-O-[4-(s)-methyl-oxazolidin-2-one]carbamoyl-5-O-[3'-N-desmethyl-3'-N-[3-(2-pyridyl)propyl]]desosaminyl-6-O-methyl-erythronolide A 11,12-(cyclic carbamate)

This compound was prepared following the procedure described in Scheme 3 for example 12, substituting 3-(2-pyridyl)propionaldehyde for cyclopropanecarboxaldehyde. The crude product was purified by silica gel column chromatography (9:1 EtOAc:acetone) to give a colorless amorphous solid: R$_f$=0.35 (9:1 CHCl$_3$:MeOH); IR (microscope) υ 3442, 2974, 2940, 1822, 1799, 1756, 1734, 1458, 1380, 1350, 1307, 1170, 1106, 1065 cm$^{-1}$; $^{13}$C NMR (100 MHz, CDCl$_3$) δ 215.7, 174.0, 161.6, 157.0, 151.4, 151.1, 148.9, 139.1, 136.4, 132.1, 130.9, 130.2, 130.1, 128.3, 122.8, 121.0, 103.3, 82.8, 81.1, 79.9, 78.5, 76.6, 70.1, 69.6, 68.5, 65.9, 60.5, 52.2, 51.4, 50.2, 45.6, 44.8, 42.8, 38.8, 38.4, 36.6, 36.3, 35.2, 32.5, 29.5, 28.1, 21.9, 21.1, 19.6, 19.5, 18.8, 15.0, 14.2, 14.1, 10.0, 8.8; MS (ESI) m/z 1019 (M+H)$^+$; Anal. Calcd for C$_{51}$H$_{72}$Cl$_2$N$_4$O$_{13}$ (1020.051): C, 60.05; H, 7.11; N, 5.49. Found: C, 60.18; H, 6.99; N, 5.56.

Example 47
11-Deoxy-11-[carboxy(3,4-dichlorophenethyl)amino]-3-O-[4-(s)-methyl-oxazolidin-2-one]carbamoyl-5-O-[3'-N-desmethyl-3'-N-[(6-methyl-2-pyridyl)methyl]]desosaminyl-6-O-methyl-erythronolide A 11,12-(cyclic carbamate)

This compound was prepared following the procedure described in Scheme 3 for Example 12, substituting 6-methyl-2-pyridinecarboxaldehyde for cyclopropanecarboxaldehyde. The crude product was purified by silica gel column chromatography (9:1 EtOAc:acetone) to give a colorless amorphous solid: R$_f$=0.40 (9:1 CHCl$_3$:MeOH); IR (microscope) υ 3450, 2975, 2940, 1820, 1800, 1760, 1740, 1460, 1380, 1350, 1310, 1180, 1110, 1060 cm$^{-1}$; $^{13}$C NMR (100 MHz, CDCl$_3$) δ 215.8, 174.0, 158.2, 157.9, 157.0, 151.3, 151.0, 139.1, 136.9, 132.1, 130.9, 130.2, 130.1, 128.3, 121.6, 119.3, 103.1, 82.8, 81.1, 79.6, 78.5, 76.6, 70.6, 69.5, 68.5, 65.1, 60.5, 58.9, 51.3, 50.1, 45.6, 44.8, 42.8, 38.8, 38.4, 37.3, 36.3, 32.5, 30.4, 24.1, 21.9, 21.1, 19.5 (2C), 18.8, 15.0, 14.2, 14.1, 10.0, 8.8; MS (ESI) m/z 1005 (M+H)$^+$; Anal. Calcd for C$_{50}$H$_{70}$Cl$_2$N$_4$O$_{13}$ (1006.024): C, 59.70; H, 7.01; N, 5.57. Found: C, 59.57; H, 6.96; N, 5.65.

Example 48
11-Deoxy-11-[carboxy(3,4-dichlorophenethyl)amino]-3-O-[4-(s)-methyl-oxazolidin-2-one]carbamoyl-5-O-[3'-desamino-3'-[1-(2,5-dimethyl)pyrrolidinyl]]desosaminyl-6-O-methyl-erythronolide A 11,12-(cyclic carbamate)

The title compound is prepared following the procedure described for Example 42, substituting acetonylacetone for cyclopropanecarboxaldehyde.

Example 49
11-Deoxy-11-[carboxy(3,4-dichlorophenethyl)amino]-3-O-[4-(s)-methyl-oxazolidin-2-one]carbamoyl-5-O-[3'-desamino-3'-(1-piperidinyl)]desosaminyl-6-O-methyl-erythronolide A 11,12-(cyclic carbamate)

The title compound is prepared following the procedure described for Example 42, substituting glutaraldehyde for cyclopropanecarboxaldehyde.

Example 50
11-Deoxy-11-[carboxy[2-(N-methyl-4-chloroanilino)ethyl]amino]-3-O-[4-(R)-methyl-oxazolidin-2-one]carbamoyl-5-

O-(3'-N-desmethyl-3'-N-isopropyl)desosaminyl-6-O-methyl-erythronolide A 11,12-(cyclic carbamate)

The title compound is prepared following the procedure described for Example 1, substituting N-(4-dichlorophenyl)-N-methylethylenediamine for 4-chlorophenethylamine.

Example 51

11-Deoxy-11-[carboxy[1-(4-chlorophenyl)cyclopropanemethyl]amino]-3-O-[4-(R)-methyl-oxazolidin-2-one]carbamoyl-5-O-(3'-N-desmethyl-3'-N-isopropyl)desosaminyl-6-O-methyl-erythronolide A 11,12-(cyclic carbamate)

The title compound is prepared following the procedure described for Example 1, substituting 1-(4-chlorophenyl)cyclopropanemethylamine for 4-chlorophenethylamine.

Example 52

11-Deoxy-11-[carboxy(3-chlorophenoxyethyl)amino]-3-O-[4-(R)-methyl-oxazolidin-2-one]carbamoyl-5-O-(3'-N-desmethyl-3'-N-isopropyl)desosaminyl-6-O-methyl-erythronolide A 11,12-(cyclic carbamate)

The title compound is prepared following the procedure described for Example 1, substituting 3-chlorophenoxyethylamine for 4-chlorophenethylamine.

Example 53

11-Deoxy-11-[carboxy(4-methoxyphenethyl)amino]-3-O-[4-(S)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate)

The title compound is prepared following the procedure described for Example 12, substituting 4-methoxyphenethylamine for 3,4-dichlorophenethylamine.

Example 54

11-Deoxy-11-[carboxy(3,4-dichlorophenethyl)amino]-3-O-[4-(S)-methyl-oxazolidin-2-one]carbamoyl-5-O-[3'-N-desmethyl-3'-N-(1-methyl-cyclopropyl)methyl]desosaminyl-6-O-methyl-erythronolide A 11,12-(cyclic carbamate).

The title compound was prepared following the procedure described in Scheme 3 for example 12, substituting 1-methyl-cyclopropanecarboxaldehyde for cyclopropanecarboxaldehyde. The crude product was purified by silica gel column chromatography (4:1 EtOAc:hexanes) to give a colorless amorphous solid: $R_f$=0.60 (9:1 CHCl$_3$:MeOH); IR (microscope) υ 3452, 2975, 2941, 1822, 1797, 1757, 1738, 1458, 1381, 1350, 1307, 1169, 1106, 1066 cm$^{-1}$; $^{13}$C NMR (75 MHz, CDCl$_3$) δ 215.8, 174.1, 157.1, 151.4, 151.1, 139.2, 132.2, 131.0, 130.3, 130.2, 128.4, 102.9, 82.8, 81.2, 79.3, 78.6, 76.6, 70.2, 69.7, 68.6, 65.7, 62.1, 60.6, 51.5, 50.3, 45.7, 44.9, 42.9, 38.9, 38.5, 37.0, 36.4, 32.6, 29.6, 22.0, 21.2, 21.1, 19.7, 19.6, 18.9, 15.1, 14.3, 14.2, 13.5, 12.3, 11.7, 10.1, 8.9; MS (ESI) m/z 968 (M+H)$^+$; Anal. Calcd for C$_{48}$H$_{71}$Cl$_2$N$_3$O$_{13}$ (969.000): C, 59.50; H, 7.39; N, 4.34. Found: C, 59.23; H, 7.36; N, 4.17.

Example 55

11-Deoxy-11-[carboxy(3-chloro-4-fluorophenethyl)amino]-3-O-[4-(S)-methyl-oxazolidin-2-one]carbamoyl-5-O-[3'-N-desmethyl-3'-N-(1-methyl-cyclopropyl)methyl]desosaminyl-6-O-methyl-erythronolide A 11,12-(cyclic carbamate).

The title compound was prepared following the procedure described in Scheme 3 for example 12, substituting 3-chloro-4-fluorophenethylamine for 3,4-dichlorophenethylamine, and substituting 1-methyl-cyclopropanecarboxaldehyde for cyclopropanecarboxaldehyde. The crude product was purified by silica gel column chromatography (4:1 EtOAc:hexanes) to give a colorless amorphous solid: $R_f$=0.70 (9:1 CHCl$_3$:MeOH); IR (microscope) υ 3440, 2975, 2940, 1820, 1755, 1735, 1715, 1460, 1380, 1355, 1305, 1170, 1105, 1065 cm$^{-1}$; $^{13}$C NMR (125 MHz, CDCl$_3$) δ 216.0, 174.0, 157.2, 156.7 (d, J=247 Hz), 151.2, 135.8 (d, J=4 Hz), 130.9, 128.5 (d, J=7 Hz), 120.5 (d, J=19 Hz), 116.3 (d, J=21 Hz), 102.7, 82.9, 81.1, 79.2, 78.5, 76.7, 70.0, 69.6, 68.6, 65.4, 61.9, 60.5, 51.4, 50.2, 45.6, 45.0, 42.8, 38.8, 38.4, 36.8, 36.3, 32.4, 29.3, 21.9, 21.1, 21.0, 19.7, 19.5, 18.9, 15.0, 14.2, 14.1, 12.3, 11.5, 10.1, 8.8; MS (ESI) m/z 952 (M+H)$^+$; Anal. Calcd for C$_{48}$H$_{71}$ClFN$_3$O$_{13}$ (952.550): C, 60.52; H, 7.51; N, 4.41. Found: C, 60.22; H, 7.44; N, 4.20.

Example 56

11-Deoxy-11-[carboxy(3-chloro-4-fluorophenethyl)amino]-3-O-[4-(S)-methyl-oxazolidin-2-one]carbamoyl-5-O-(3'-bis-N-desmethyl-3'-N-cyclopropylmethyl-3'-N-isopropyl)desosaminyl-6-O-methyl-erythronolide A 11,12-(cyclic carbamate).

This compound was prepared following the procedure described for example 20, substituting 3-chloro-4-fluorophenethylamine for 3,4-dichlorophenethylamine, and substituting cyclopropanecarboxaldehyde for acetaldehyde. The crude product was purified by silica gel column chromatography (1:1 EtOAc:hexanes) to give a colorless amorphous solid: $R_f$=0.60 (9:1 CHCl$_3$:MeOH); $^{13}$C NMR (100 MHz, CDCl$_3$) δ 215.9, 174.1, 157.1, 156.8 (d, J=247 Hz), 151.3, 151.0, 135.9 (d, J=4 Hz), 131.0, 128.5 (d, J=7 Hz), 120.5 (d, J=17 Hz), 116.3 (d, J=20 Hz), 102.8, 82.8, 81.1, 78.9, 78.5, 76.7, 70.2, 69.9, 68.5, 60.5, 59.6, 51.3, 50.2, 49.4, 47.8, 45.7, 45.0, 42.9, 38.8, 38.5, 36.3, 34.5, 32.4, 22.9, 21.9, 21.2, 19.7, 19.5, 18.9, 18.7, 15.0, 14.3, 14.1, 11.1, 10.1, 8.9, 5.5, 2.7; MS (APCI) m/z 966 (M+H)$^+$.

Example 57

11-Deoxy-11-[carboxy(3,4-dichlorophenethyl)amino]-3-O-[4(S)-methyl-oxazolidin-2-one]carbamoyl-5-O-(3'-bis-N-desmethyl-3'-N-cyclopropylmethyl-3'-N-ethyl)desosaminyl-6-O-methyl-erythronolide A 11,12-(cyclic carbamate) (Compound 34, Scheme 6).

Scheme 6
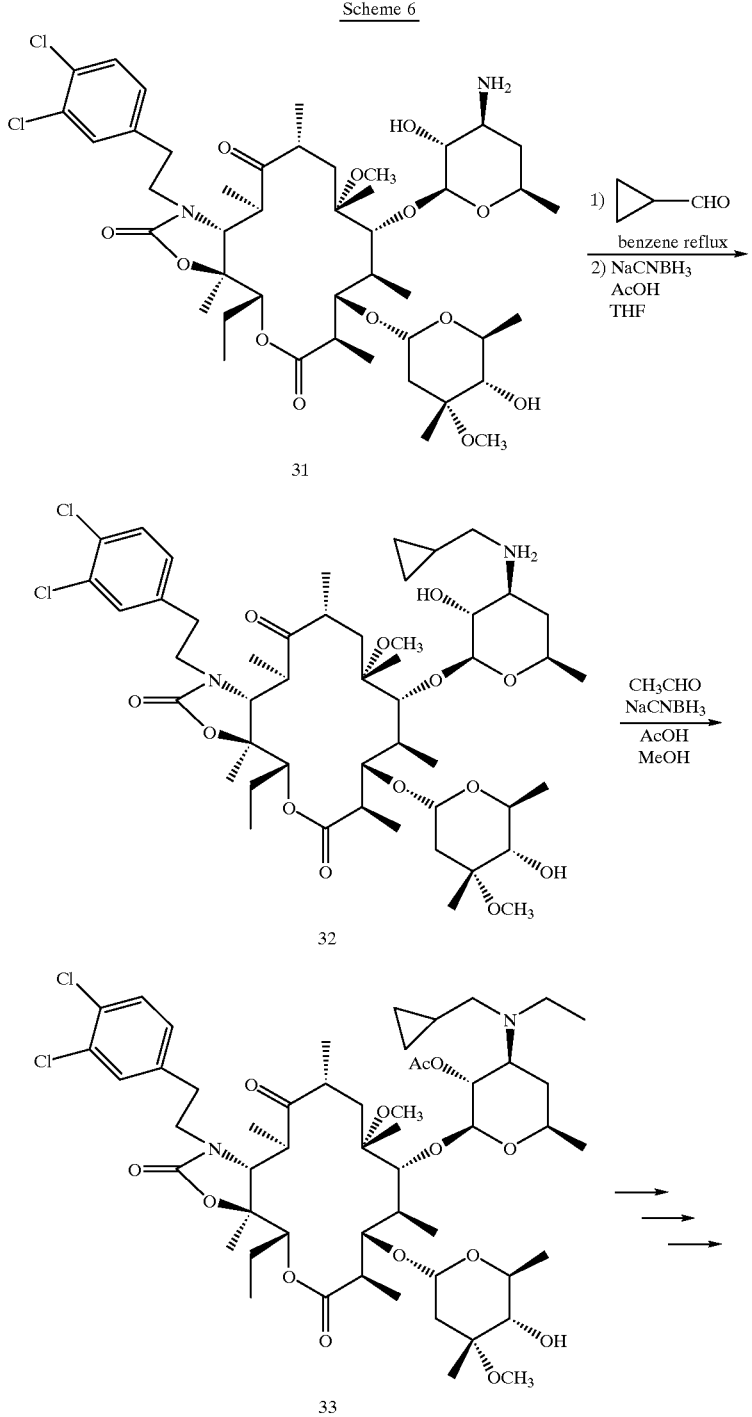

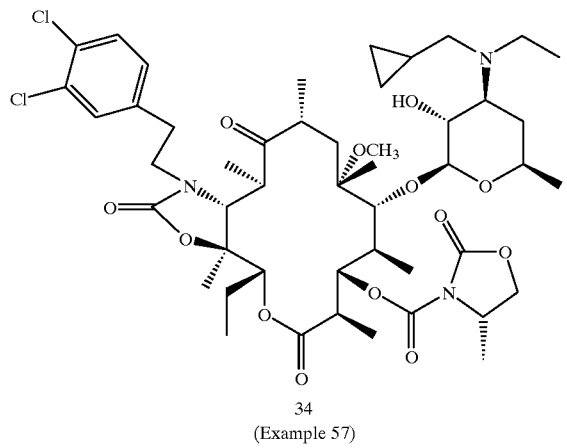

34
(Example 57)

Step 1: 3'-Bis-N-desmethyl-3'-N-cyclopropylmethyl-3'-N-ethyl-11-deoxy-11-[carboxy(3,4-dichlorophenethyl)amino]-6-O-methyl-erythromycin A 11,12-(cyclic carbamate) (Compound 33, Scheme 6).

A solution of 11-deoxy-11-[carboxy(3,4-dichlorophenethyl)amino]-3'-bis-N-desmethyl-6-O-methyl-erythromycin A 11,12-(cyclic carbamate) (Compound 31) (1.00 mg, 1.09 mmol), prepared as previously described from 11-deoxy-11-[carboxy(3,4-dichlorophenethyl)amino]-6-O-methyl-erythromycin A 11,12-(cyclic carbamate) (Compound 23, Scheme 4), in MeOH (10 mL) and cyclopropanecarboxaldehyde (0.50 mL) was stirred at rt 16 h. The solvent was evaporated, and the residue was dissolved in benzene (20 mL). The solution was warmed to 50° C. and evaporated to dryness using a dry $N_2$ stream. The azeotrope process was repeated to give the 3'-imine as a colorless solid, which was dried in vacuo. The 3'-imine was dissolved in anhydrous THF (10 mL) under dry $N_2$ and cooled to 0° C. before adding a solution of $NaCNBH_3$ (1.0 M in anhydrous THF, 1.50 mL) and AcOH (0.10 mL, 1.75 mmol). The reaction mixture was allowed to warm to rt, after which time TLC (90:10:1 $CHCl_3$:MeOH:$NH_4OH$) indicated the reaction was complete. The mixture was partitioned between $H_2O$ (150 mL) and EtOAc (3×100 mL), and the combined organic layers were dried over $Na_2SO_4$. The drying agent was filtered off, and the solvent was removed in vacuo to give a crude product which was purified by column chromatography on silica gel (9:1 $CHCl_3$:MeOH) to give 11-deoxy-11-[carboxy(3,4-dichlorophenethyl)amino]-3'-bis-N-desmethyl-3'-N-cyclopropylmethyl-6-O-methyl-erythromycin A 11,12-(cyclic carbamate) (Compound 32) as a colorless amorphous solid [(0.39 g, 37%), $R_f$=0.45 (90:10:1 $CHCl_3$:MeOH:$NH_4OH$), MS (APCI) m/z 971 (M+H)$^+$]. To a solution of compound 32 (0.26 g, 0.27 mmol) in MeOH (2.5 mL) at 0° C. was added AcOH (15 μL, 0.25 mmol) and acetaldehyde (0.15 mL, 2.69 mmol), followed by $NaCNBH_3$ (25 mg, 0.40 mmol). The mixture was stirred at 0° C. for 1 h, after which time TLC (9:1 $CHCl_3$:MeOH) indicated the reaction was complete. The mixture was partitioned between $H_2O$ (50 mL) and EtOAc (3×50 mL), and the combined organic layers were dried over $Na_2SO_4$. The drying agent was filtered off, and the solvent was removed in vacuo to give a crude product which was purified by column chromatography on silica gel (EtOAc) to give compound 33 as a colorless amorphous solid (182 mg, 68%): $R_f$=0.45 (9:1 $CHCl_3$:MeOH); IR (microscope) υ 3465, 2975, 2940, 1750, 1735, 1710, 1460, 1375, 1240, 1165, 1110, 1065, 1055, 1015, 1005 cm$^{-1}$; $^{13}C$ NMR (100 MHz, $CDCl_3$) δ 216.2, 176.3, 157.1, 139.2, 132.1, 130.9, 130.1, 130.0, 128.3, 103.0, 95.9, 82.8, 80.1, 78.8, 77.8, 77.7, 76.1, 72.6, 70.4, 69.0, 65.7, 61.9, 60.3, 54.3, 50.6, 49.4, 45.5, 45.2, 44.7, 43.2, 39.0, 38.9, 34.8, 32.5, 30.4, 21.8, 21.4 (2C), 20.1, 18.8, 18.6, 16.0, 14.4, 14.1, 14.0, 10.4, 10.2, 8.9, 5.3, 2.6; MS (ESI) m/z 999 (M+H)$^+$; Anal. Calcd for $C_{51}H_{80}Cl_2N_2O_{13}$ (1000.095): C, 61.25; H, 8.06; N, 2.80. Found: C, 60.95; H, 8.00; N, 2.70.

Step 2: 11-Deoxy-11-[carboxy(3,4-dichlorophenethyl)amino]-3-O-[4-(s)-methyl-oxazolidin-2-one]carbamoyl-5-O-(3'-bis-N-desmethyl-3'-N-cyclopropylmethyl-3'-N-ethyl)desosaminyl-6-O-methyl-erythronolide A 11,12-(cyclic carbamate) (Compound 34, Scheme 6).

This compound was prepared from 3'-bis-N-desmethyl-3'-N-cyclopropylmethyl-3'-N-ethyl-11-deoxy-11-[carboxy(3,4-dichlorophenethyl)amino]-6-O-methyl-erythromycin A 11,12-(cyclic carbamate) (Compound 33) following an analogous procedure to that described in Scheme 4 for the conversion of 3'-bis-N-desmethyl-3'-bis-N-cyclopropylmethyl-11-deoxy-11-[carboxy(3,4-dichlorophenethyl)amino]-6-O-methyl-erythromycin A 11,12-(cyclic carbamate) (Compound 24) to 11-deoxy-11-[carboxy(3,4-dichlorophenethyl)amino]-3-O-[4-(s)-methyl-oxazolidin-2-one]carbamoyl-5-O-(3'-bis-N-desmethyl-3'-bis-N-cyclopropylmethyl)desosaminyl-6-O-methyl-erythronolide A 11, 12-(cyclic carbamate) (Compound 27). The crude product was purified by silica gel column chromatography (EtOAc) to give a colorless amorphous solid: $R_f$=0.10 (EtOAc); IR (microscope) υ 3442, 2973, 2937, 1823, 1800, 1758, 1738, 1461, 1380, 1350, 1306, 1169, 1106, 1065 cm$^{-1}$; $^{13}C$ NMR (100 MHz, $CDCl_3$) δ 215.8, 174.0, 157.0, 151.2, 151.1, 139.1, 132.1, 130.9, 130.2, 130.1, 128.3, 102.8, 82.8, 81.1, 79.3, 78.5, 76.7, 70.0, 69.7, 68.6, 62.2, 60.5, 54.6, 51.4, 50.2, 45.6, 44.8, 42.9, 38.8, 38.4, 36.3, 32.5, 30.7, 29.6, 21.9, 21.1, 19.7, 19.5, 18.9, 15.0, 14.2, 14.1, 10.0, 8.9, 5.2, 3.0; MS (APCI) m/z 968 (M+H)$^+$.

Example 58

11-Deoxy-11-[carboxy(3-chloro-4-fluorophenethyl)amino]-3-O-[4-(s)-methyl-oxazolidin-2-one]carbamoyl-5-O-(3'-bis-N-desmethyl-3'-N-cyclopropylmethyl-3'-N-ethyl)desosaminyl-6-O-methyl-erythronolide A 11,12-(cyclic carbamate).

The title compound was prepared following the procedure described for example 57, substituting 3-chloro-4-fluorophenethylamine for 3,4-dichlorophenethylamine. The crude product was purified by silica gel column chromatography (1:1 EtOAc:hexanes) to give a colorless amorphous solid: $R_f$=0.40 (19:1 $CHCl_3$:MeOH); IR (microscope) υ 3450, 2970, 2930, 1820, 1800, 1760, 1740, 1460, 1380, 1350, 1305, 1170, 1105, 1065 $cm^{-1}$, $^{13}C$ NMR (75 MHz, $CDCl_3$) δ 215.9, 174.1, 157.1, 156.8 (d, J=247 Hz), 151.3, 151.1, 135.9 (d, J=4 Hz), 131.0, 128.5 (d, J=7 Hz), 120.6 (d, J=18 Hz), 116.4 (d, J=21 Hz), 102.9, 82.8, 81.2, 79.2, 78.6, 76.8, 70.1, 70.0, 68.6, 62.2, 60.6, 54.6, 51.4, 50.3, 45.7, 45.1, 43.4, 42.9, 38.9, 38.5, 36.4, 32.5, 30.6, 29.7, 22.0, 21.2, 21.0, 19.7, 19.5, 18.9, 15.1, 14.4, 14.3, 14.2, 10.4, 10.1, 8.9, 5.3, 2.9; MS (APCI) m/z 952 $(M+H)^+$.

We claim:

1. A compound represented by the formula:

I or a pharmaceutically acceptable salt or ester thereof, wherein

A is selected from the group consisting of:
(a) —C,
(b) —N, and
(c) —O, and
(d) cycloalkyl;

X and Y are independently selected at each occurrence from the group consisting of:
(a) hydrogen,
(b) halide,
(c) alkoxy,
(d) alkyl,
(e) aryl, and
(f) substituted aryl;

R and $R^1$ are independently at each occurrence
a) hydrogen,
b) alkyl,
c) cycloalkyl, d) $(CH_2)_r$—[pyridyl with $R^4$], wherein $R^4$ is independently at each occurrence a hydrogen or an alkyl, and r is 0, 1, 2, 3, or 4; or
e) taken together with the nitrogen to which they are attached R and $R^1$ form

[structure with $(CH_2)_m$, $R^4$, N, $R^4$]

wherein $R^4$ is as defined above, and m is 2, 3, or 4;

$R_2$ and $R_3$ are independently at each occurrence
(a) hydrogen,
(b) methyl, or $R_2$ and $R_3$ together form a cyclic moiety, when A is C;
$R_3$ is absent when A is N, and
n=1, 2 or 3; and
Z is

[structure with $R^5$, $R^6$, U, V, $R^4$, $R^4$, $R^4$]

wherein
U is —CH, —$CCH_3$ or —N;
V is $CH_2$, O, or S;
$R^4$ is as defined above; and
$R^5$ and $R^6$ are independently at each occurrence hydrogen or alkyl, or together they form —C=O or —C=S.

2. The compound of claim 1, wherein R and $R^1$ are independently at each occurrence hydrogen, alkyl or cycloalkyl, X and Y are halogens, A is —C, and $R^2$ and $R^3$ are both hydrogen.

3. The compound of claim 1 selected from the group consisting of:
11-Deoxy-11-[carboxy-(4-chlorophenethyl)amino]-3-O-[4-(R)-methyl-oxazolidin-2-one] carbamoyl-5-O-(3'-N-desmethyl-3'-N-isopropyl)desosaminyl-6-O-methyl-erythronolide A 11,12-(cyclic carbamate);
11-Deoxy-11-[carboxy-(4-chlorophenethyl)amino]-3-O-[oxazolidin-2-one]carbamoyl-5-O-(3'-N-desmethyl-3'-N-isopropyl)desosaminyl-6-O-methyl-erythronolide A 11,12-(cyclic carbamate);
11-Deoxy-11-[carboxy-(4-chlorophenethyl)amino]-3-O-[4-(S)-ethyl-oxazolidin-2-one] carbamoyl-5-O-(3'-N-desmethyl-3'-N-isopropyl)desosaminyl-6-O-methyl-erythronolide A 11,12-(cyclic carbamate);
11-Deoxy-11-[carboxy-(4-chlorophenethyl)amino]-3-O-[4,5-(S,R)-dimethyl-oxazolidin-2-one]carbamoyl-5-O-(3'-N-desmethyl-3'-N-isopropyl)desosaminyl-6-O-methyl-erythronolide A 11,12-(cyclic carbamate);
11-Deoxy-11-[carboxy-(4-chlorophenethyl)amino]-3-O-[4,4-dimethyl-oxazolidin-2-one]carbamoyl-5-O-(3'-N-desmethyl-3'-N-isopropyl)desosaminyl-6-O-methyl-erythronolide A 11,12-(cyclic carbamate);
11-Deoxy-11-[carboxy(4-chlorophenethyl)amino]-5-O-(3'-N-desmethyl-3'-N-isopropyl)desosaminyl-3-O-[4-(s)-methyl-oxazolidin-2-one]carbamoyl-6-O-methyl-erythronolide A 11,12-(cyclic carbamate);
11-Deoxy-11-[carboxy(4-chlorophenethyl)amino]-5-O-(3'-bis-N-desmethyl-3'-N-isopropyl)desosaminyl-3-O-[4-(s)-methyl-oxazolidin-2-one]carbamoyl-6-O-methyl-erythronolide A 11,12-(cyclic carbamate);

11-Deoxy-11-[carboxy(4-chlorophenethyl)amino]-5-O-(3'-N-desmethyl-3'-N-isopropyl)desosaminyl-3-O-[4-(R)-methyl-oxazolidine]carbamoyl-6-O-methyl-erythronolide A 11,12-(cyclic carbamate);

11-Deoxy-11-[carboxy(4-chlorophenethyl)amino]-5-O-(3'-N-desmethyl-3'-N-isopropyl)desosaminyl-3-O-(tetrahydro-2-furoyl)-6-O-methyl-erythronolide A 11,12-(cyclic carbamate);

11-Deoxy-11-[carboxy(4-chlorophenethyl)amino]-5-O-(3'-bis-N-desmethyl-3'-N-isopropyl)desosaminyl-3-O-(tetrahydro-2-furoyl)-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-N-desmethyl-3'-N-cyclobutyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-N-desmethyl-3'-N-cyclopentyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-N-desmethyl-3'-N-cyclohexyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-N-desmethyl-3'-N-n-propyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-N-desmethyl-3'-N-isobutyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-N-desmethyl-3'-N-cyclobutylmethyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-N-desmethyl-3'-N-isopropyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-bis-N-desmethyl-3'-N-ethyl-3'-N-isopropyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-bis-N-desmethyl-3'-N-n-propyl-3'-N-isopropyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-bis-N-desmethyl-3'-N-cyclopropylmethyl-3'-N-isopropyl)desosaminyl-6-O-methyl-erythronolide A 11,12-(cyclic carbamate);

11-Deoxy-11-[carboxy(4-chlorophenethyl)amino]-3-O-[4-(s)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate);

11-Deoxy-11-[carboxy(4-chlorophenethyl)amino]-3-O-[4-(s)-methyl-oxazolidin-2-one]carbamoyl-5-O-(3'-N-desmethyl-3'-N-cyclobutyl)desosaminyl-6-O-methyl-erythronolide A 11,12-(cyclic carbamate);

11-Deoxy-11-[carboxy(4-chlorophenethyl)amino]-3-O-[4-(s)-methyl-oxazolidin-2-one]carbamoyl-5-O-(3'-N-desmethyl-3'-N-cyclopentyl)desosaminyl-6-O-methyl-erythronolide A 11,12-(cyclic carbamate);

11-Deoxy-11-[carboxy(4-chlorophenethyl)amino]-3-O-[4-(s)-methyl-oxazolidin-2-one]carbamoyl-5-O-(3'-N-desmethyl-3'-N-cyclohexyl)desosaminyl-6-O-methyl-erythronolide A 11,12-(cyclic carbamate);

11-Deoxy-11-[carboxy(4-chlorophenethyl)amino]-3-O-[4-(s)-methyl-oxazolidin-2-one]carbamoyl-5-O-(3'-N-desmethyl-3'-N-n-propyl)desosaminyl-6-O-methyl-erythronolide A 11,12-(cyclic carbamate);

11-Deoxy-11-[carboxy(4-fluorophenethyl)amino]-3-O-[4-(s)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate);

11-Deoxy-11-[carboxy(4-fluorophenethyl)amino]-3-O-[4-(s)-methyl-oxazolidin-2-one]carbamoyl-5-O-(3'-N-desmethyl-3'-N-cyclobutyl)desosaminyl-6-O-methyl-erythronolide A 11,12-(cyclic carbamate);

11-Deoxy-11-[carboxy(4-fluorophenethyl)amino]-3-O-[4-(s)-methyl-oxazolidin-2-one]carbamoyl-5-O-(3'-N-desmethyl-3'-N-cyclopentyl)desosaminyl-6-O-methyl-erythronolide A 11,12-(cyclic carbamate);

11-Deoxy-11-[carboxy(4-fluorophenethyl)amino]-3-O-[4-(s)-methyl-oxazolidin-2-one]carbamoyl-5-O-(3'-N-desmethyl-3'-N-n-propyl)desosaminyl-6-O-methyl-erythronolide A 11,12-(cyclic carbamate);

11-Deoxy-11-[carboxy(4-fluorophenethyl)amino]-3-O-[4-(s)-methyl-oxazolidin-2-one]carbamoyl-5-O-(3'-N-desmethyl-3'-N-isopropyl)desosaminyl-6-O-methyl-erythronolide A 11,12-(cyclic carbamate);

11-Deoxy-11-[carboxy(3-chloro-4-fluorophenethyl)amino]-3-O-[4-(s)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate);

11-Deoxy-11-[carboxy(3-chloro-4-fluorophenethyl)amino]-3-O-[4-(s)-methyl-oxazolidin-2-one]carbamoyl-5-O-(3'-N-desmethyl-3'-N-cyclobutyl)desosaminyl-6-O-methyl-erythronolide A 11,12-(cyclic carbamate);

11-Deoxy-11-[carboxy(3-chloro-4-fluorophenethyl)amino]-3-O-[4-(s)-methyl-oxazolidin-2-one]carbamoyl-5-O-(3'-N-desmethyl-3'-N-cyclopentyl)desosaminyl-6-O-methyl-erythronolide A 11,12-(cyclic carbamate);

11-Deoxy-11-[carboxy(4-chloro-3-fluorophenethyl)amino]-3-O-[4-(s)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate);

11-Deoxy-11-[carboxy(3,4-dichlorophenethyl)amino]-3-O-[4-(R)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate);

11-Deoxy-11-[carboxy(3,4-dichlorophenethyl)amino]-3-O-[4-(s)-ethyl-oxazolidin-2-one]carbamoyl-5-O-(3'-N- desmethyl-3'-N-cyclopropylmethyl)desosaminyl-6-O-methyl-erythronolide A 11,12-(cyclic carbamate);

11-Deoxy-11-[carboxy(3,4-dichlorophenethyl)amino]-3-O-[5-(R)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate);

11-Deoxy-11-[carboxy(3,4-dichlorophenethyl)amino]-3-O-[4-(s)-methyl-thiazolidin-2-one]carbamoyl-5-O-(3'-N-desmethyl-3'-N-cyclopropylmethyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-thione]carbamoyl-5-O-(3'-N-desmethyl-3'-N-cyclopropylmethyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-bis-N-desmethyl-3'-bis-N-cyclopropylmethyl)desosaminyl-6-O-methyl-erythronolide A 11,12-(cyclic carbamate);

11-Deoxy-11-[carboxy(3-chloro-4-fluorophenethyl)amino]-3-O-[4-(s)-methyl-oxazolidin-2-one]carbamoyl-5-O-(3'-bis-N-desmethyl-3'-bis-N-cyclopropylmethyl)desosaminyl-6-O-methyl-erythronolide A 11,12-(cyclic carbamate);

11-Deoxy-11-[carboxy(4-chloro-3-fluorophenethyl)amino]-3-O-[4-(s)-methyl-oxazolidin-2-one]carbamoyl-5-O-(3'-bis-N-desmethyl-3'-bis-N-cyclopropylmethyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-(3'-bis-N-desmethyl-3'-N-cyclopropylmethyl)desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-[3'-N-desmethyl-3'-N-[3-(2-pyridyl)propyl]]desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-[3'-N-desmethyl-3'-N-[(6-methyl-2-pyridyl)methyl]]desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-[3'-bis-N-desmethyl-3'-[1-(2,5-dimethyl)pyrrolidinyl]]desosaminyl-6-O-methyl-erythronolide A 11,12-(cyclic carbamate);

11-Deoxy-11-[carboxy(3,4-dichlorophenethyl)amino]-3-O-[4-(s)-methyl-oxazolidin-2-one]carbamoyl-5-O-[3'-bis-N-desmethyl-3'-(1-piperidinyl)]desosaminyl-6-O-methyl-erythronolide A 11,12-(cyclic carbamate);

11-Deoxy-11-[carboxy[2-(N-methyl-4-chloroanilino)ethyl]amino]-3-O-[4-(R)-methyl-oxazolidin-2-one]carbamoyl-5-O-(3'-N-desmethyl-3'-N-isopropyl)desosaminyl-6-O-methyl-erythronolide A 11,12-(cyclic carbamate);

11-Deoxy-11-[carboxy(3-chlorophenoxyethyl)amino]-3-O-[4-(R)-methyl-oxazolidin-2-one]carbamoyl-5-O-(3'-N-desmethyl-3'-N-isopropyl)desosaminyl-6-O-methyl-erythronolide A 11,12-(cyclic carbamate); and 11-Deoxy-11-[carboxy(4-methoxyphenethyl)amino]-3-O-[4-(s)-methyl-oxazolidin-2-one]carbamoyl-5-O-(3'-N-desmethyl-3'-N-cyclopropylmethyl)desosaminyl-6-O-methyl-erythronolide A 11,12-(cyclic carbamate).

4. A pharmaceutical composition for inhibiting the release of LH (luteinizing hormone) comprising a therapeutically effective amount of a compound according to claim 1 in combination with a pharmaceutically acceptable carrier.

5. A process for preparing the compound according to claim 1 comprising the steps of:

(a) demethylating 3'-amino of a compound of formula:

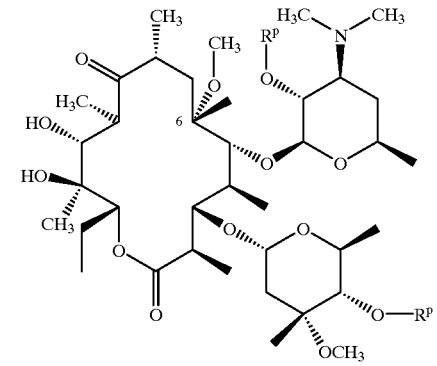

with iodine in presence of a base, followed by alkylation to afford a compound of the formula:

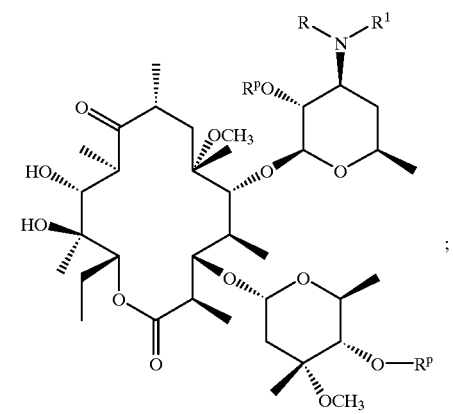

wherein RP is a hydroxy-protecting group;

(b) protecting the 2'- and 4"-hydroxy groups;

(c) reacting the compound obtained in steps (a) and (b) with sodium bis(trimethylsilyl)amide and carbonyldiimidazole, followed by reaction with an amino compound of the formula:

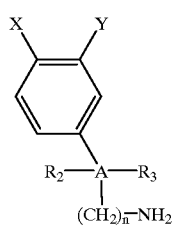

to afford a compound of the formula:

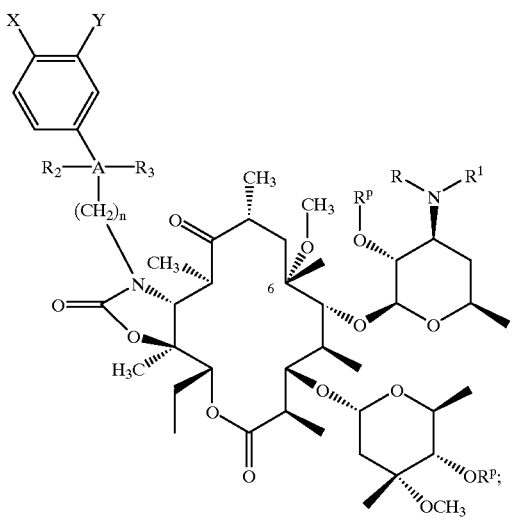

(d) hydrolyzing the compound obtained in step (c) with an acid to afford a compound of the formula:

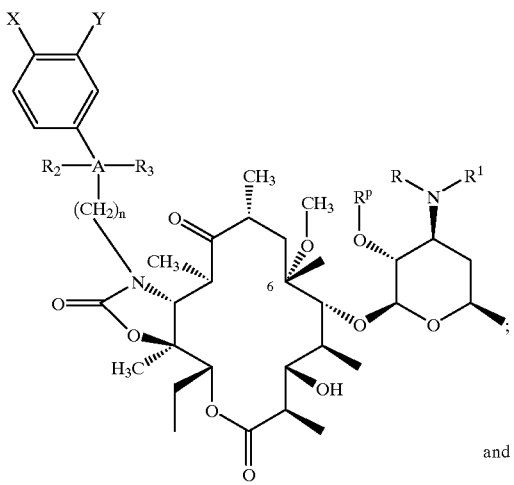

and (e) derivatizating the 3-hydroxy followed by deprotection of the 2'-hydroxy group.

6. The process according to claim 5, wherein the reaction in step (b) is carried out without solvent or in acetonitrile at 25 to 80° C.

7. The process according to claim 5, wherein the desmethylation is carried out by reaction of the compound obtained in step (b) with iodine in the presence of a base and a light or heat source.

8. The process according to claim 5, wherein the desmethylation is carried out by reaction of the compound obtained in step (b) with a chloroformate selected from the group consisting of benzyl chloroformate, allyl chloroformate and vinyl chloroformate.

9. The process according to claim 5, wherein the alkylation in step (d) is achieved by reaction of the compound obtained in step (c) with an aldehyde or ketone in the presence of a hydride metal or in the presence of Pd/C catalyst in a protic or non-protic solvent under hydrogen.

10. The process according to claim 5, wherein the alkylation in step (d) is achieved by reaction of the compound obtained in step (c) with an alkyl halide in presence of a base.

11. The process of claim 5, wherein R is alkyl, alkenyl, cycloalkyl, heterocyclic, (heterocyclic)alkyl or alkylcycloalkyl; X and Y are independently at each occurrence chloro, fluoro, dioxalano, hydrogen, or alkoxy; A is —C; $R_2$ and $R_3$ are independently at each occurrence hydrogen or together they form cylopropyl moiety and n is 1.

12. The process of claim 5, wherein the alkylating agent is cyclopentanone and the alkylation is carried out in the presence of sodium cyanoborohydride in methanol.

* * * * *